US006933118B2

(12) United States Patent
Inoko et al.

(10) Patent No.: US 6,933,118 B2
(45) Date of Patent: Aug. 23, 2005

(54) METHOD OF TESTING FOR PSORIASIS VULGARIS

(75) Inventors: Hidetoshi Inoko, 1583-1-101, Funako, Atsugi-shi, Kanagawa 243-0034 (JP); Gen Tamiya, Kanagawa (JP)

(73) Assignee: Hidetoshi Inoko, Kanagawa (JP)

( * ) Notice: Subject to any disclaimer, the term of this patent is extended or adjusted under 35 U.S.C. 154(b) by 0 days.

(21) Appl. No.: 10/164,230

(22) Filed: Jun. 6, 2002

(65) Prior Publication Data

US 2003/0170652 A1 Sep. 11, 2003

Related U.S. Application Data

(63) Continuation-in-part of application No. PCT/JP00/08624, filed on Dec. 6, 2000.

(30) Foreign Application Priority Data

Dec. 6, 1999 (JP) .......................................... 11-346867

(51) Int. Cl.$^7$ ........................ C12Q 1/68; C12P 19/34; C07H 21/04
(52) U.S. Cl. ........................ 435/6; 435/91.1; 435/91.2; 536/23.1; 536/24.3; 536/24.33; 536/24.32
(58) Field of Search ............................. 435/6; 536/23.1, 536/24.31, 24.33, 24.3

(56) References Cited

U.S. PATENT DOCUMENTS 5,811,233 A * 9/1998 Bowcock et al. .............. 435/6

FOREIGN PATENT DOCUMENTS

| WO | WO 00/58506 | 10/2000 |
| WO | WO 02/44736 | 6/2002 |

OTHER PUBLICATIONS

Oka et al. Association analysis using refined microsatellite markers localizes a susceptibility locus for psoriasis vulgaris within a 111 kb segment telomeric to the HLA–C gene. Human Molecular Genetics, vol. 8, No. 12, pp. 2165–2170, 1999.*
Genback Accession No. AB029343 (1999).
Zhou et al., "Identification in the HLA class I region of a gene expressed late in keratinocyte differentiation", Proc. Natl. Acad. Sci., pp. 9470–9474, vol. 90(20), (1993).
Mahairas G.G. et al., "Sequence–tagged connectors: A sequence approach to mapping and scanning the human genome", Proc. Natl. Acad. Sci., pp. 9739–9744, vol. 96(17), (1999).
Shiina T. et al., "Molecular dynamics of MHC genesis unraveled by sequence analysis of the 1,796,938–bp HLS class I region", Proc. Natl. Acad. Sci., pp. 13282–13287, vol. 96(23), (1999).
Oka A. et al., "Association analysis using refined microsatellite markers localizes a susceptibility locus for psoriasis vulgaris within a 111 kb segment telomeric to the *HLA–C* gene", Human Molecular Genetics, pp. 2165–2170, vol. 8(12), (1999).

Hui J. et al., "Corneodesmosin DNA polymorphisms in MHC haplotypes and Japanese patients with *psoriasis*", Tissue Antigens, pp. 77–83, vol. 60(1), (2002).
Oka A. et al., Bio Clinica, pp. 169–175, vol. 17(2), (2002). (Concise explanation attached).
Teraoka Y. et al., "Genetic polymorphisms in the cell growth regulated gene, SC1 telomeric of the HLA–C gene and lack of association of psoriasis vulgaris", Tissue Antigens, pp. 206–211, vol. 55(3), (2000).
Tamiya G. et al., "New polymorphic microsatellite markers in the human MHC class I region", Tissue Antigens, pp. 221–228, vol. 54(3), (1999).
Shiina T. et al., "Genome sequencing analysis fo the 1.8 Mb entire human MHC class I region", Immunological Reviews, pp. 193–199, vol. 167, (1999).
Ozawa A. et al., "HLA Class I and II Alleles and Susceptibility to Generalized Pustular Psoriasis: Significant Associations with HLA–Cw1 and HLA–DQB1 *0303", The Journal of Dermatology, pp. 573–581, vol. 25(9), (1998).
Tamiya G. et al., "Twenty–six new polymorphic microsatellite markets around the HLA–B, –C and –E loci in the human MHC class I region", Tissue Antigens, pp. 337–346, vol. 51 (4 Pt 1), (1998).
Nakazawa A. et al., Nippon Hifuka Gakkai Zasshi, pp. 1797–1801, vol. 101(14), (1991). (English Abstract Attached).
Ozawa A. et al., "Specific Restriction Fragment Length Polymorphism on the HLA–C Region and Susceptibility to Psoriasis Vulgaris", The Journal of Investigative Dermatology, pp. 402–405, vol. 90(3), (1988).
Ahnini et al. "Novel genetic association between the corneodesmosin (*MHC S*) gene and susceptibility to psoriasis" Human Mol. Genet. 8(6):1135–1140 (1999).
Allen et al. "A non–HLA gene within the MHC in psoriasis" Lancet 353:1589–1590 (1999).
Genebank Accession No. AB023060 : Homo sapiens genomic DNA, chromosome 6p21.3, HLA class I region.
Genebank Accession No. AF030130 : Homo sapiens corneodesmosin mRNA, complete cds.

(Continued)

*Primary Examiner*—Kenneth R. Horlick
*Assistant Examiner*—Cynthia Wilder
(74) *Attorney, Agent, or Firm*—Fish & Richardson P.C.

(57) ABSTRACT

By a detailed analysis of the sequences of the MHC S gene, SEEK1 gene, and HCR gene of Japanese patients with psoriasis and healthy individuals, it was demonstrated that some of the examined polymorphisms significantly correlate with psoriasis in the group of Japanese patients. Based on these correlations, it was demonstrated that psoriasis vulgaris can be detected by analyzing these gene polymorphisms in patients with psoriasis.

16 Claims, 3 Drawing Sheets

OTHER PUBLICATIONS

Guerrin et al. "Expression Cloning of Human Corneodesmosin Proves Its Identity with the Product of the *S* Gene and Allows Improved Characterization of Its Processing during Keratinocyte Differentiation" *J. Biol. Chem.* 273(35):22640–22647 (1998).

Jenisch et al. "Corneodesmosin gene polymorphism demonstrates strong linkage disequilibrium with HLA and association with psoriasis vulgaris" *Tissue Antigens* 54:439–449 (1999).

EMBL Accession No. AP000510 : Homo sapiens genomic DNA, chromosome 6p21.3, HLA Class I region.

Geneback Accession No. AB031479 : Homo sapiens SEEK1 mRNA, complete cds.

Holm et al., "Polymorphisms in the *SEEK*1 and *SPR*1 genes on 6p21.3 associate with psoriasis in the Swedish population," *Experimental Dermatology*, 12(4):435–444 (2003).

Inoko H., 1998 nendo Kagaku Kenkyuhi Hojokin Tokutei Ryouiki Kenkyu (A) (I) Kenkyu Seika Houkokusho; Genome Science: Hito Genome Kaiseki ni motozuku Bioscience no Shin Tenkai, pp. 14–23 (1999).

Inoko H., Monbusho Kagaku Kenkyuhi Hojokin Tokutei Ryouiki Kenkyu Heisei 10 nendo Kenkyu Seika Houkokusho; Menekibyou no Bunshi Kikou to sono Shuufuku, pp. 94–95 (1999).

Morita E. et al., Nishi Nippon Hifuka, 58(6):991–993 (1996).

Ozawa A. et al., Kisho Nanjisei Hifu Shikkan Chosa Kenkyuhan, Heisei 7nendo Kenkyu Houkokusho, pp. 223–225 (1996).

Tamiya G. et al., Idenshi Igaku, 3(1):54–62 (1999).

* cited by examiner

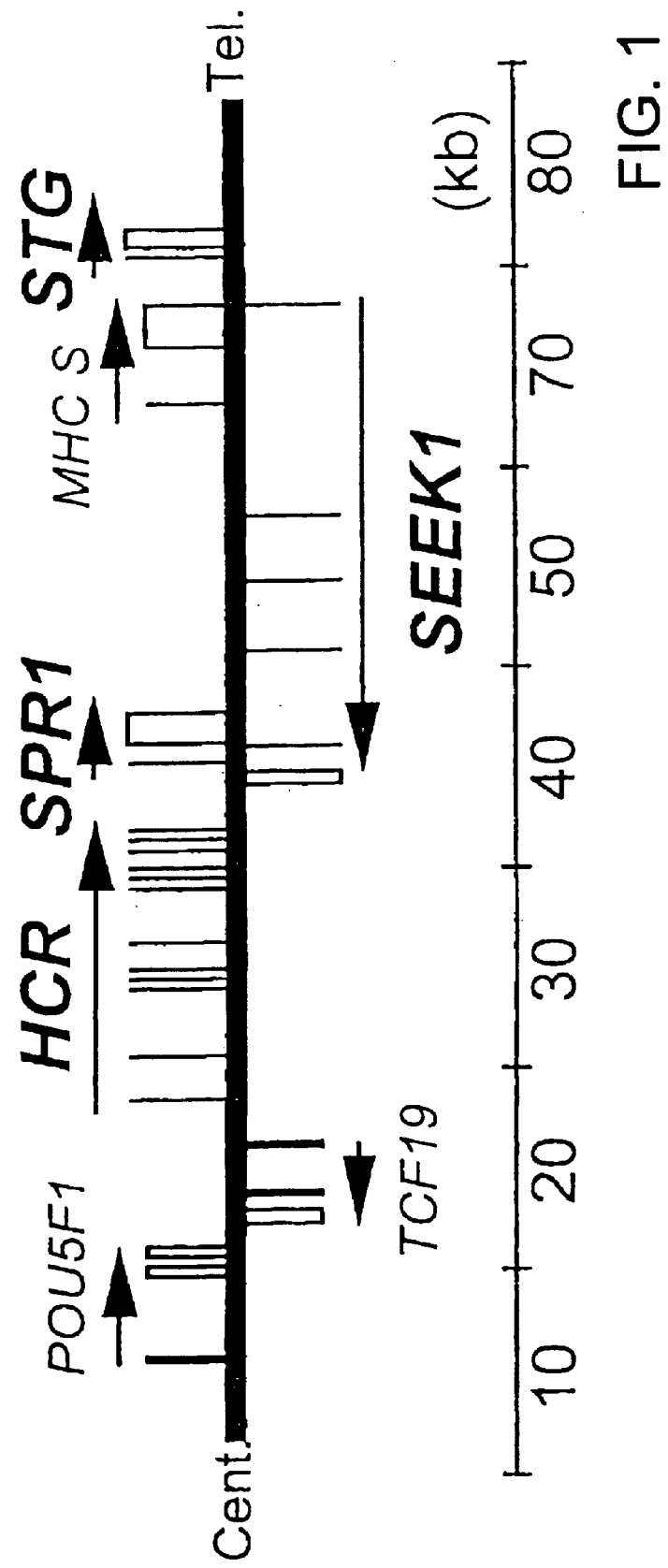

FIG. 2

```
ccgtgcagtccgagatgggctcgtctcgggcaccctggatggggcgtgtgggtgggcacg    60
                     M  G  S  S  R  A  P  W  M  G  R  V  G  G  H  G   (16)
ggatgatggcactgctgctggctggtctcctcctgccagggaccttggctaagagcattg   120
 M  M  A  L  L  L  A  G  L  L  L  P  G  T  L  A  K  S  I  G   (36)
gcaccttctcagacccctgtaaggaccccacgcgtatcacctcccctaacgacccctgcc   180
 T  F  S  D  P  C  K  D  P  T  R  I  T  S  P  N  D  P  C  L   (56)
tcactgggaagggtgactccagcggcttcagtagctacagtggctccagcagttctggca   240
 T  G  K  G  D  S  S  G  F  S  S  Y  S  G  S  S  S  S  G  S   (76)
gctccatttccagtgccagaagctctggtggtggctccagtggtagctccagcggatcca   300
 S  I  S  S  A  R  S  S  G  G  G  S  S  G  S  S  S  G  S  S   (96)
gcattgcccagggtggttctgcaggatcttttaagccaggaacggggtattcccaggtca   360
 I  A  Q  G  S  A  G  S  F  K  P  G  T  G  Y  S  Q  V  S     (116)
gctactcctccggatctggctctagtctacaaggtgcatccggttcctcccagctgggga   420
 Y  S  S  G  S  G  S  S  L  Q  G  A  S  G  S  S  Q  L  G  S   (136)
gcagcagctctcactcgggaaRcagcggctctcactcgggAAGcYgcagStctcattcga   480
 S  S  S  H  S  G  S(N)S  G  S  H  S  G  S(-)S(C)S(R)S  H  S  S   (156)
gcagcagcagcagctttcagttcagcagcagcagcttccaagtagggaatggctctgctc   540
 S  S  S  F  Q  F  S  S  S  F  Q  V  G  N  G  S  A  L       (176)
tgccaaccaatgacaactcttaccgcggaatactaaacccttcccagcctggacaaagct   600
 P  T  N  D  N  S  Y  R  G  I  L  N  P  S  Q  P  G  Q  S  S   (196)
cttcctcttcccaaaccTYtggggtatccagcagtggccaaagcgtcagctccaaccagc   660
 S  S  S  Q  T  S(F)G  V  S  S  S  G  Q  S  V  S  N  Q  R   (216)
gtccctgtagttcggacatccccgactctccctgcagtggagggcccatcgtctcgcact   720
 P  C  S  S  D  I  P  D  S  P  C  S  G  G  P  I  V  S  H  S   (236)
ctggcccctacatccccagctcccactctgtgtcaggggtcagaggcctgtggtggtgg   780
 G  P  Y  I  P  S  S  H  S  V  S  G  G  Q  R  P  V  V  V  V   (256)
tggtggaccagcacggttctggtgcccctggagtggttcaaggtccccctgtagcaatg   840
 V  D  Q  H  G  S  G  A  P  G  V  V  Q  G  P  P  C  S  N  G   (276)
gtggccttccaggcaagWcctgtcccccaatcacctctgtagacaaatcctatggtggct   900
 G  L  P  G  K  P(T)C  P  P  I  T  S  V  D  K  S  Y  G  G  Y   (296)
acgaggtggtgggtggctcctctgacagttatctggttccaggcatgacctacagtaagg   960
 E  V  V  G  S  S  D  Y  L  V  P  G  M  T  Y  S  K  G       (316)
gtaaaatctatcctgtgggctacttcaccaaagagaaccctgtgaaggctctccagggg  1020
 K  I  Y  P  V  G  Y  F  T  K  E  N  P  V  K  G  S  P  G  V   (336)
tcccttccttttgcagctgggccccccatctctgaggcaaatacttctccagcaaccca  1080
 P  S  F  A  A  G  P  P  I  S  E  G  K  Y  F  S  S  N  P  I   (356)
tcatccccagccagtcggcagcttcctcggccattgcgttccagccagtggggactggtg  1140
 I  P  S  Q  S  A  A  S  S  A  I  A  F  Q  P  V  G  T  G  G   (376)
gggtccagctctgtggaggcggctccacgggctccaagggaccctgctctcccctccagtt  1200
 V  Q  L  C  G  G  S  T  G  S  K  G  P  C  S  P  S  S     (396)
ctcgagtccccagcRgttctagcatttccagcagKcCgKtYaccctaccatccctgcg  1260
 R  V  P  S  S(G)S  S  I  S  S  S  A(S)G(V)S(L)P  Y  H  P  C  G   (416)
gcagtgcttcccagagcccctgctcccaccaggcaccggctccttcagcagcagctcca  1320
 S  A  S  Q  S  P  C  S  P  P  G  T  G  S  F  S  S  S  S   (436)
gttcccaatcgagtggcaaaatcatccttcagccttgtggcagcaagtccaRctcttctg  1380
 S  Q  S  S  G  K  I  I  L  Q  P  C  G  S  K  S  S(N)S  S  G   (456)
gtcaccttgcatgtctgtctcctccttgacactgactggggccccgatggctctcccc  1440
 H  P  C  M  S  V  S  S  L  T  L  T  G  G  P  D  G  S  P  H   (476)
atcctgatccctccgctggtgccaagccctgtggctccagcagtgctggaaagatccct  1500
 P  D  P  S  A  G  A  K  P  C  G  S  S  A  G  K  I  P  C   (496)
gccgctccatccgggatatcctagcccaagtgaagcctctggggcccagctagctgacc  1560
 R  S  I  R  D  I  L  A  Q  V  K  P  L  G  P  Q  L  A  D  P   (516)
ctgaagtttcctaccccaaggagagttactcRacagtccataagtcaactgttgtgtgt  1620
 E  V  F  L  P  Q  G  E  L  L  D(N)S  P  *                  (529)
gtgcatgccttgggcacaaacaagcacatacactatatcccatatgggagaaggccagtg  1680
cccaggcatagggttagctcagttttccctccttcccaaaagagtg               1730
```

FIG. 3

```
CGCCCTTTCAACTCTGCCAAGAATGGCTCCCACCTGGCTCTCAGACATTCCCTGGTCCA    60
            M  A  P  T  W  L  S  D  I  P  L  V  Q
ACCCCCAGGCCATCAAGATGTCTCAGAGAGGCGGCTAGACACCCAGAGACCTCAAGTGAC   120
  P  P  G  H  Q  D  V  S  E  R  R  L  D  T  Q  R  P  Q  V  T
CATGTGGGAACGGGATGTTTCCAGTGACAGGCAGGAGCCAGGGCGGAGAGGCAGGTCCTG   180
  M  W  E  R  D  V  S  S  D  R  Q  E  P  G  R  R  G  R  S  W
GGGGCTGGAGGGGTCACAGGCCCTGAGCCAGCAGGCTGAGGTGATCGTTCGGCAGCTGCA   240
  G  L  E  G  S  Q  A  L  S  Q  Q  A  E  V  I  V  R  Q  L  Q
AGAGCTGCRGTGGCTGGAGGAGGAGGTCTGGCTCCTGCGGGAGACCTCGCTGCAGCAGAA   300
  E  L  RQW  L  E  E  E  V  W  L  L  R  E  T  S  L  Q  Q  K
GATGAGGCTAGAGGCCCAGGCCATGGAGCTAGAGGCTCTGGCACGGGCGGAGAAGGCCGG   360
  M  R  L  E  A  Q  A  M  E  L  E  A  L  A  R  A  E  K  A  G
CCGAGCTGAGGCTGAGGGCCTGCGTGCTGCTTTGGCTGGGGCTGAGGTTGTCCGGAAGAA   420
  R  A  E  A  E  G  L  R  A  A  L  A  G  A  E  V  V  R  K  N
CTTGGAAGAGGGGAGSCAGCGGGAGCTGCAAGAGGTTCAGAGGCTGCACCAAGAGCAGCT   480
  L  E  G  RS Q  R  E  L  E  E  V  Q  R  L  H  Q  E  Q  L
GTCCTCTTTGACACAGGCTCACGAGGAGGCTCTTTCCAGTTTGACCAGCAAGGCTGAGGG   540
  S  S  L  T  Q  A  H  E  E  A  L  S  S  L  T  S  K  A  E  G
CTTGGAGAAGTCTCTGAGTAGTCTGGAAACCAGAAGAGCAGGGGAAGCCAAGGAGCTGGC   600
  L  E  K  S  L  S  S  L  E  T  R  R  A  G  E  A  K  E  L  A
CGAGGCTCAGAGGGAGGCCGAGCTGCTTCGGAAGCAGCTGAGCAAGACCCAGGAAGACTT   660
  E  A  Q  R  E  A  E  L  L  R  K  Q  L  S  K  T  Q  E  D  L
GGAGGCTCAGGTGACCCTGGTTGAGAATCTAAGAAAATATGTTGGGGAACAAGTCCCTTC   720
  E  A  Q  V  T  L  V  E  N  L  R  K  Y  V  G  E  Q  V  P  S
TGAGGTCCACAGCCAGACATGGGAACTGGAGCGACAGAAGCTTCTGGAMACCATGCAGCA   780
  E  V  H  S  Q  T  W  E  L  E  R  Q  K  L  L  EOT  M  Q  H
CTTGCAGGAGGACCGGGACAGCCTGCATGCCACCGCGGAGCTGCTGCAGGTGCGGGTGCA   840
  L  Q  E  D  R  D  S  L  H  A  T  A  E  L  L  Q  V  R  V  Q
GAGCCTCACACACATCCTCGCCCTGCAGGAGGAGGAGCTGACCAGGAAGGTTCAACCTTC   900
  S  L  T  H  I  L  A  L  Q  E  E  E  L  T  R  K  V  Q  P  S
AGATTCCCTGGAGCCTGAGTTTACCAGGAAGTGCCAGTCCCTGCTGAACCGCTGGCGGGA   960
  D  S  L  E  P  E  F  T  R  K  C  Q  S  L  L  N  R  W  R  E
GAAGGTGTTTGCCCTCATGGTGCAGCTAAAGGCCCAGGAGCTGGAACACAGTGACTCTGT  1020
  K  V  F  A  L  M  V  Q  L  K  A  Q  E  L  E  H  S  D  S  V
TAAGCAGCTGAAGGGACAGGTGGCCTCACTCCAGGAAAAAGTGACATCCCAGAGCCAGGA  1080
  K  Q  L  K  G  Q  V  A  S  L  Q  E  K  V  T  S  Q  S  Q  E
GCAGGCCATCCTGCAGCGATCCCTGCAGGACAAAGCCGCAGAGGTGGAGGTGGAGCGTAT  1140
  Q  A  I  L  Q  R  S  L  Q  D  K  A  A  E  V  E  V  E  R  M
GGGTGCCAAGGGCCTGCAGTTGGAGCTGAGCCGTGCTCAGGAGGCCAGGCGTYGGTGGCA  1200
  G  A  K  G  L  Q  L  E  L  S  R  A  Q  E  A  R  R  WRH  Q
GCAGCAGACAGCCTCAGCCGAGGAGCAGTTGAGGCTTGTGGTCAATGCTGTCAGCAGCTC  1260
  Q  Q  T  A  S  A  E  E  Q  L  R  L  V  V  N  A  V  S  S  S
TCAGATCTGGCTCGAGACCACCATGGCTAAGGTGGAAGGGGCTGCCGCCCAGCTTCCCAG  1320
  Q  I  W  L  E  T  T  M  A  K  V  E  G  A  A  A  Q  L  P  S
CCTCAACAACCGACTCAGCTATGCTGTCCGCAAGGTCCACACCATTCGGGGCCTGATTGC  1380
  L  N  N  R  L  S  Y  A  V  R  K  V  H  T  I  R  G  L  I  A
TCGAAAGCTTGCCCTTGCTCAGCTGCGCCAGGAGAGCTGTCCCCTACCACCACCGGTCAC  1440
  R  K  L  A  L  A  Q  L  R  Q  E  S  C  P  L  P  P  P  V  T
AGATGTGAGCCTTGAGTTGCAGCAGCTGCGGGAAGAACGGAACCGCCTGGATGCAGAACT  1500
  D  V  S  L  E  L  Q  Q  L  R  E  E  R  N  R  L  D  A  E  L
GCAGCTGAGTGCCCGCCTCATCCAGCAGGAGGTGGGCCGGGCTCGGGAGCAAGGGGAGGC  1560
  Q  L  S  A  R  L  I  Q  Q  E  V  G  R  A  R  E  Q  G  E  A
AGAGCGGCAGCAGCTGAGCAAGGTGGCCCAGCAGCTGGAGCAGGAGCTGCAGCAGACCCA  1620
  E  R  Q  Q  L  S  K  V  A  Q  Q  L  E  Q  E  L  Q  Q  T  Q
GGAGTCCCTGGCTAGCTTGGGGCTGCAGCTGGAGGTAGCACGCCAGTGCCAGCAGGAGAG  1680
  E  S  L  A  S  L  G  L  Q  L  E  V  A  R  Q  C  Q  Q  E  S
CACAGAGGAGGCTGCCAGTCTGCGGCAGGAGCTGACCCAGCAGCAGGAACTCTACGGGCA  1740
  T  E  E  A  A  S  L  R  Q  E  L  T  Q  Q  Q  E  L  Y  G  Q
AGCCCTGCAAGAAAAGGTGGCTGAAGTGGAAACTCGGCTGCGGGAACAACTCTCAGACAC  1800
  A  L  Q  E  K  V  A  E  V  E  T  R  L  R  E  Q  L  S  D  T
AGAGAGGAGGCTGAACGAGGCTCRGAGGGAGCATGCCAAGGCCCGTGGTCTCCTTRGCCA  1860
  E  R  R  L  N  E  A  RQR  E  H  A  K  A  V  V  S  LIR QY
KATTCAGCGCAGAGCCGCCCAGGAAAWGAGCGGAGCCAGGAACTCAGGVGTCTGCAGGA  1920
  I  Q  R  R  A  A  Q  E  KM  R  S  Q  E  L  R  RCL  Q  E
GGAGGCCCGGAAGGAGGAGGGGCAGCGACTGGCCCGGCGCTTGCAGGAGCTAGAGAGGGA  1980
  E  A  R  K  E  E  G  Q  R  L  A  R  R  L  Q  E  L  E  R  D
TAAGAACCTCATGCTGGCCACCTTGCAGCAGGAAGGTCTCCTCTCCCGTTACAAGCAGCA  2040
  K  N  L  M  L  A  T  L  Q  Q  E  G  L  L  S  R  Y  K  Q  Q
GCGACTGTTGACAGTTCTTCCTTCCCTGGATAAGAAGAAATCTGTGGTGTCCAGCCC    2100
  R  L  L  T  V  L  P  S  L  D  K  K  K  S  V  V  S  S  P
CAGGCCTCCAGAGTGTTCAGCATCTGCACCTGTAGCAGCAGCAGTGCCCACCAGGGAGTC  2160
  R  P  P  E  C  S  A  S  A  P  V  A  A  A  V  P  T  R  E  S
CATAAAAGGGTCCCTCTCTGTCCTGCTCGATGACCTGCAGGACCTGAGTGAAGCCATTTC  2220
  I  K  G  S  L  S  V  L  L  D  D  L  Q  D  L  S  E  A  I  S
CAAAGAGGAAGCTGTTTGTCAAGGAGACAACCTTGACAGATGCTCCAGCTSCAATCCCCA  2280
  K  E  E  A  V  C  Q  G  D  N  L  D  R  C  S  S  CSN  P  Q
GATGAGCAGCTAAGCAGCTGACAGTTGGAGGGAAAGCCAGCCTGGGGGCTGGGAGGATCC  2340
  M  S  S  *
TGGAGAAGTGGGTGGGGACAGACCCAGCCCTTCCCCCATCCTGGGGTTGCCCTGGGGATAC  2400
CAGCTGAGTCTGAATTCTGCTCTAAATAAAGACGACTACAGAAGGAAAAAAAAAAAAAA   2460
AAAAAAAAAAAAAAA                                                 2474
```

SEQUENCE LISTING

<160> NUMBER OF SEQ ID NOS: 63

<210> SEQ ID NO 1
<211> LENGTH: 5337
<212> TYPE: DNA
<213> ORGANISM: Homo sapiens
<220> FEATURE:
<221> NAME/KEY: exon
<222> LOCATION: (1)...(99)
<220> FEATURE:
<221> NAME/KEY: exon
<222> LOCATION: (2904)...(5337)

<400> SEQUENCE: 1

```
ccgtgcagcc cgagatgggc tcgtctcggg caccctggat ggggcgtgtg ggtgggcacg      60
ggatgatggc actgctgctg gctggtctcc tcctgccagg taggaggctg ggggccctgg     120
gaacaggagg gaggcgggag ggagactccg ggagaggacc cagcgaaggg gacgggcagg     180
ggctctggaa tctgcctttt gagtctgggg gttgctcctc actgtatggt cgcctcaggt     240
aagtttctta aacttcctga gccccagttt ctgaaattct gaagtgggt taatgacacc      300 tacctctagt ctgtgtgtct caaattaaat aatgtatgtg atatgtactt tggaaattct     360
agaggtttat ataaatggtg gtggtgattt ttattatggg agcactacaa gataatgatt     420
ggacatttaa tagtaataat atcattttta gagcctttt atatgctaga ctctgtttta      480
agcacatttg gattatatat tagaactttt atttttattt tttttgtgag atggagtccc     540
actctgtctc caaggctgga gtgcagtggc gtaatctcgg ctcactgcaa cttccacctc     600
tcaggttcaa gcgactctca tgcctcagcc tctagagtag ctgggacaac aggtgcccat     660
caccacacct ggctaatttt ctttttttg tattttagt agaaacaggg ttttaccatt      720
ttggtcaagc tggtcttgaa ctcctgactc aagtgatccg ctcgcctcgg cctcccaagg     780
tgctgggatt acaggcatga gccaccacac ccggcctata ttagcacttt tgatcattac     840
aagaacggta tgaaaagaga tttgctattt ccactctaca gatgaggaca ctgaggctcg     900
gagaggttag gaaactagct caaaatcatg cattagaagg cagcaaagcc aagatttcaa     960
ccccaggcca ggcaacccct ggacctgtgt tgttgaccac cgggtactta tagcccttga    1020
ggaatttctg cgaccttccc atggtctagt gggtggttgg tgtctgaggg aatagcgaaa    1080
gagagaggca atgcatggtg gattcgtgca gaggactgaa gggaattggc acagctgggg    1140
ttcggcgtgg aggtgcatgc agagaatttc tttctgagga gagaacaggg acatcacaga    1200
ggatggcagt ctggttgttg gtggagggat caggatgagt ggcagtaata attcataata    1260
tataatgctt tacactttct aaaacatctg gccgcacatg atagcttgtg cctgtaatcc    1320
caacacttca ggaggccaag gcaggtgaat cgcctgaggt caggagttca agaccagcct    1380
ggccaagatg gtgaaacccc ctctctacta aaaatacaaa aaattagctg ggtgtggtgg    1440
cgggcacctg tggtcccagc tacttgggag gctgaggcag gagaatcgct tgcaccaagg    1500
aggcagaggt tacagtgagc tgagaccgtg ttattgcact ttagcctggg caacaagaaa    1560
ctccatctca caaaaaaaa aaaaaaaaa aaaagaaga aaaacttcc aggtggatga       1620
```

```
tctcatttag ttttcttcat agtaatgctg tgggaaggca gggaaaattt ggcccctctg    1680
aatgtataaa ctaaagctca gagaggttca gtaacttgct agtatgtggc tctgtttgta    1740
acacgtggga cctggagggg ctagggaagg cagaaggaac gcaggtgaaa gagtcatgga    1800
ggaaccatgg ggtaagttgg gcctggggtt ttgagcaaag gaaaggaaag ataaggaaag    1860
atgtggctcc acatccctga gggaagtcaa ggcagcagaa gtcagatgag gggctggaca    1920
gaggcaggtg tgctcagaga gggaagctga ttgtggccag gagcctcgga ggttcgtggg    1980
gtttcgtcct ggttccctgg gctgggccag cgagagcagg gctggctcag ggtgcggtgt    2040
cctgacacac tggtaccagc aggttctgaa gcaacaggta gtgaccccac atcctggccc    2100
ccacccagct ttactggcat ggccagtgct gagataggaa atagggtttc cattcctgac    2160
cccagcctgg gctctcacga agaagctggt gaccaaatct tagtcctcga gtgcccttt c    2220 ctttatttca gcccctctgc ccccagcttt gtcttttt cc agtgtctcct tctatatgtg    2280
tctccacttc tcagccctcc attgttttgc cttttgtctt cttccctctg gtcccactgt    2340
ctggcccagg atttttcccc taagaattta cgcctggact cctcagagcc tcagtttccc    2400
caattctctg tctcttcagg gtcctttctt ttagacctat tgttcctgc ccttctcca      2460 ttccctcttc tttttaaaaa aaattttaat taaaaaacaa aatacagatg gggtctatgt    2520
tgcccaggct ggtcttgaac tctggggcgc atgcaatcct cccacctcag cctcccaaag    2580
tgctgggatt accggcgtga gccactgtgc ccagcccct cttatattca atgtattcct     2640
ttgaggtcac tcactttggc acgtaatttt ctatttttct ggttggtgtt tgcccaccct    2700
tcccaaacaa agaaatgcct ttattcggcc acctcaatat cctttagaga caatagccag    2760
ttcttcctcc tttctccatc cctaaactct ccctgcgctc tgcttgggag aaacccgaga    2820
ggccgattac tgagataagg cagaaaggtg agggaggaag ccaagcctct ttggccctta    2880
ctaaccactg ctttcctcca cagggacctt ggctaagagc attggcacct tctcagaccc    2940
ctgtaaggac cccacgcgta tcacctcccc taacgacccc tgcctcactg ggaagggtga    3000
ctccagcggc ttcagtagct acagtggctc cagcagttct ggcagctcca tttccagtgc    3060
cagaagctct ggtggtggct ccagtggtag ctccagcgga tccagcattg cccagggtgg    3120
ttctgcagga tcttttaagc caggaacggg gtattcccag gtcagctact cctccggatc    3180
tggctctagt ctacaaggtg catccggttc ctcccagctg gggagcagca gctctcactc    3240
gggaagcagc ggctctcact cgggaagcag cagctctcat cgagcagca gcagcagctt    3300 tcagttcagc agcagcagct tccaagtagg gaatggctct gctctgccaa ccaatgacaa    3360
ctcttaccgc ggaatactaa acccttccca gcctggacaa agctcttcct cttcccaaac    3420
ctctggggta tccagcagtg gccaaagcgt cagctccaac cagcgtccct gtagttcgga    3480
catccccgac tctccctgca gtggagggcc catcgtctcg cactctggcc cctacatccc    3540
cagctcccac tctgtgtcag ggggtcagag gcctgtggtg gtggtggtgg accagcacgg    3600
ttctggtgcc cctggagtgg ttcaaggtcc cccctgtagc aatggtggcc ttccaggcaa    3660
gccctgtccc ccaatcacct ctgtagacaa atcctatggt ggctacgagg tggtgggtgg    3720
ctcctctgac agttatctgg ttccaggcat gacctacagt aagggtaaaa tctatcctgt    3780
gggctacttc accaaagaga accctgtgaa aggctctcca ggggtccctt cctttgcagc    3840
tgggccccca atctctgagg gcaaatactt ctccagcaac cccatcatcc ccagccagtc    3900
ggcagcttcc tcggccattg cgttccagcc agtgggact ggtggggtcc agctctgtgg    3960
aggcggctcc acgggctcca agggaccctg ctctccctcc agttctcgag tccccagcag    4020
```

```
ttctagcatt tccagcagct ccggttcacc ctaccatccc tgcggcagtg cttcccagag      4080
cccctgctcc ccaccaggca ccggctcctt cagcagcagc tccagttccc aatcgagtgg      4140
caaaatcatc cttcagcctt gtggcagcaa gtccagctct tctggtcacc cttgcatgtc      4200
tgtctcctcc ttgacactga ctgggggccc cgatggctct ccccatcctg atccctccgc      4260
tggtgccaag ccctgtggct ccagcagtgc tggaaagatc ccctgccgct ccatccggga      4320
tatcctagcc caagtgaagc ctctggggcc ccagctagct gaccctgaag ttttcctacc      4380
ccaaggagag ttactcgaca gtccataagt caactgttgt gtgtgtgcat gccttgggca      4440
caaacaagca catacactat atcccatatg ggagaaggcc agtgcccagg catagggtta      4500
gctcagtttc cctccttccc aaaagagtgg ttctgctttc tctactaccc taaggttgca      4560
gactctctct tatcacccct tcctccttcc tcttctcaaa atggtagatt caaagctcct      4620
ctcttgattc tctcctactg tttaaattcc cattccacca cagtgcccct cagccagatc      4680
accacccctt acaattccct ctactgtgtt gaaatggtcc attgagtaac cccccatca      4740 ccttctcaac tgggaaaccc ctgaaatgct ctcagagcac ctctgacgcc tgaagaagtt      4800
ataccttcct cttcccctt accaaataaa gcaaagtcaa accatcatct ggaaacagtg      4860
gccacttttc actgacctct cttcgacatc tagtcaaccc acccaatatg ccactgggct      4920
ttcgctccca attccacccc acctccatt acagagctca ccacgccctc ctagatcacc      4980
gtccccaaca cacccattgc ctctcaaggc cttatctca gccccttcct gtggccattt      5040
ccctcagtgc ccagatgatt ccctgggtga gggagacact ggggcaccct cagaggttgg      5100
agcaggctcc ctgctgtccc tggatcctgg acagatggct cagtaaactg tggggactag      5160
gtgcagactt tttgccttct tggagtcctg ggtctcctct gagagtctgg gtggtgctct      5220
tcctacgcct ctagaggtct ctgtgtccct catttccctt caaaagcggg ctgtgtttct      5280
cttctacctt ccagctcctc ccacagagga ggaagacaat aaatatttgt tgaactg       5337

<210> SEQ ID NO 2
<211> LENGTH: 25235
<212> TYPE: DNA
<213> ORGANISM: Homo sapiens
<220> FEATURE:
<221> NAME/KEY: exon
<222> LOCATION: (1)...(420)
<220> FEATURE:
<221> NAME/KEY: exon
<222> LOCATION: (1282)...(1405)
<220> FEATURE:
<221> NAME/KEY: exon
<222> LOCATION: (1602)...(1702)
<220> FEATURE:
<221> NAME/KEY: exon
<222> LOCATION: (1602)...(1631)
<220> FEATURE:
<221> NAME/KEY: exon
<222> LOCATION: (2352)...(2364)
<220> FEATURE:
<221> NAME/KEY: exon
<222> LOCATION: (6287)...(6509)
<220> FEATURE:
<221> NAME/KEY: exon
<222> LOCATION: (10417)...(10493)
<220> FEATURE:
<221> NAME/KEY: exon
<222> LOCATION: (14244)...(14407)
<220> FEATURE:
<221> NAME/KEY: exon
<222> LOCATION: (14244)...(14344)
<220> FEATURE:
<221> NAME/KEY: exon
```

<222> LOCATION: (25190)...(25235)

<400> SEQUENCE: 2

| | | | | | |
|---|---|---|---|---|---|
| gcggaccagg | cagggaacaa | cctgggagga | atcaaatttt | attttggaca | tgttacttct | 60 |
| gaaaggctaa | cagacttcca | ggcagaaagg | tccttgaggg | aaacattcta | ggggtctctc | 120 |
| tgggaggctt | agatcaagga | gctgagacca | aaggagaat | gggagggagg | agacgagtac | 180 |
| aatagagttg | gagccaaggt | cctagaggcg | ataggtgga | ttcctgaggg | aggaggaagg | 240 |
| ggctgaggtt | gctggagcct | ggcagcttct | tccggagcca | ttggcaggac | tgatgcaaac | 300 |
| agctctgggt | gggaagaggg | aaccaggata | tcctcctgtg | tccttccttt | tctgcagtca | 360 |
| tcctgggtgg | ctgccagatg | gaattccttg | gatatcattg | cttggaggtc | ccctgcatgc | 420 |
| ctgaagaagg | acatggtgga | gagcaggatg | cctggatccc | atggggaag | ggaagtgccc | 480 |
| aggaaagcac | gaagcccag | ggggagcttt | cagtgcgggg | gtgagtgggg | aggctggggt | 540 |
| agtagctgac | actgtcccag | ctgcatccca | ggtttgaaag | gcacctcctc | ccccagcgca | 600 |
| ggcatcctgc | ctcccaaccc | tgtaattacg | gtgcttccca | acgcccatcg | tgtggtttgc | 660 |
| tcccattctt | tggcttccaa | tagttgcaag | ggatgaaggt | ggacatctct | gtgattacgg | 720 |
| agatgccaag | tgggtattga | ctgctccagg | gtgtggatgg | agggtgtgaa | aaccagggtg | 780 |
| gggtgacgca | ggctctgggt | catgataggg | agagcaggca | gctgggtcct | gggctggagg | 840 |
| actaaaataa | gggacgccac | cttcagggt | gacacatcag | cccaggcctt | cccaacgggt | 900 |
| ttgaccagtt | ctgttctgat | ggtattcctg | tgccactggg | ctggtccctc | ctccactcct | 960 |
| ccccctataaa | gcctcttggg | gttcccaggc | acccagactc | agcccacccc | agctttgggg | 1020 |
| gccagtacat | agccatgatc | ctcaactgga | agctcctggg | gatcctggtc | ctttgcctgc | 1080 |
| acaccagagg | tgaggtggga | acagaggcag | ggactgcagt | ttggggtgat | gagggatact | 1140 |
| caagatggcg | gaggtgaact | ggacgcatgg | ggttggggac | aggaattcag | gggacgcaga | 1200 |
| aggtgcatct | ggctcaccag | aaatggcttt | ctggacacat | tgggtggggg | acatggtgca | 1260 |
| gaaggtgcat | ttggctctca | ccagaaatgg | tttgctggct | ccatgtggca | aagtcggtca | 1320 |
| ggattaacgt | ggggggacg | agtttccttg | gagctgggat | ctgtgttaag | gagctggggt | 1380 |
| ccttgtaaag | ctgggtctg | tgtgcctggg | ggccaaggtg | taacccacct | tgggttgcag | 1440 |
| gttggcctga | ggacaaagct | agtggggtac | cccaaccagg | ggtggatgga | gcttatttgg | 1500 |
| agaagtctgg | tcagtttaaa | gtgggtcaag | tgaacggttc | agatccatcg | ggggtagggg | 1560 |
| ttcatgacat | tttaccatca | gttaagtatt | tacaaaccta | ccgagagctc | tttgagagtg | 1620 |
| acttttttgg | tctgtttgtg | ggtcagttca | ggctgcgtcc | gtccagacag | gctcctcctc | 1680 |
| ctggggctgg | ggctgggtgg | ggctggggag | agaagccctc | accacctctt | acctttctcc | 1740 |
| ttcctccttt | acaggcatct | caggcagcga | gggccacccc | tctcacccac | ccgcagagga | 1800 |
| ccgagaggag | gcaggctccc | caacattgcc | tcagggcccc | ccagtccccg | gtgacccttg | 1860 |
| gccaggggca | ccccctctct | ttgaagatcc | tccgcctacc | cgcccagtc | gtccctggag | 1920 |
| agacctgcct | gaaactggag | tctggccccc | tgaaccgcct | agaacggatc | ctcctcaacc | 1980 |
| tccccggcct | gacgacccttt | ggccggcagg | accccagccc | ccagaaaacc | cctggcctcc | 2040 |
| tgcccctgag | gtgacaacc | gacctcagga | ggagccagac | ctagacccac | cccgggaaga | 2100 |
| gtacagataa | tggagtcccc | tcagccgttc | tgttcccagg | catctccagg | cacccacgcc | 2160 |
| ctctccaccc | tctgattccc | cgtgaattct | tcccaattta | gcctatctcc | ttaaacctct | 2220 |
| tcctcattcc | ctcggttta | ttctgaaccc | gtaaggtggt | gttctcaata | tttcctgtcc | 2280 |

-continued

```
cctcctgaga tccatactta gtcctcacat cgcccgtttt ttcctctgac agcctaagcc   2340
tactctccta cctcgcctcc aggcctcggc cccacctacc tcccacccgg tcttcctgcc   2400
cgcgcgatcg ctggggcagg gctacggtac tgtgttccct tctgccacct ggtggccggc   2460
ggcaggaact atcagtagac agctgctgct tccatgaaac ggaaaaataa aaatcatgtt   2520
ttcttaactc tgaatctagg ctgctgcttt aactaaacact tagggtcttt ttcatttatt   2580
tttatttatt tgttttttc ttttttgag acgaagtctc gctctgtcgc ccaggctgga   2640
gtacagtggc acgatctcgg ctcactgcaa gctccgcctc ccgggttcac gctattctgc   2700
ctcagcctcc cgagtagctg ggactacagg cgcccgccac cacgccaggc taatttttg   2760 tatttttag tagaggcggg gtttcaccgt gttagccaga gtggtctcga tctcctgacc   2820
tcgtgatctg cccgcctggg cctcccaaag tgctgggatt acacgcgtga gccacagcgc   2880
ccggcttctt tcttcttttt ctttcttttt tttttagatg gagtctcact ctatgcccag   2940
gctggagtgc aatggcacga tctcggctca ctgcaacctc cggctcccgg gttcaagcca   3000
ttctcctgcc tcagccttct gagtagctgg gattacaggt gcgcaccacc atgcccggct   3060 aattttgta ttttagtaga gatggggttt caccatgttg gccaggctgg tctcgaactc   3120
ctgacatcgt gatctcccg cctcggcctc ccaaagggct gggattacag gcgtgagcca   3180
ccgtgcccgg ccaacactta tgttttgac tattaggatg ccctcttcac agtcctaaac   3240
ttacggagac ctggaagtaa cttgagttcc tatcttgccc atgtccagca tgtaaggctc   3300
tggggcttag caggaggagg gttggaaatg tcactatgca agtcacaata acattcaggc   3360
ccacatttct ccctttctga gaacactata ttaaagaatg ggaaggcaag tttcatctct   3420
gtttaatggc ctatgcttg gataccccta gtggtatatg caaaccttcc cagggggtgtg   3480 tcggcaggac cagttttaag ggaatcagtt tccagattaa tatgtgcccc ccgctagaat   3540
gaatctcctg cttgtcctgg gcctgaccag agtgcccttc ccagagccgc caaaggtcaa   3600
taggaaacaa atcaaccttt cccatctcat taagagattc attttctttc ttttcttttt   3660 ttttttttt tgagacgtat tatctctctg tcgcccaggc tggagtgcag tggcacgaca   3720
gatatcagct cactgcaagc ttcgcctcct ggattcaagt gattctcctg cctcaacctc   3780
ccgagtagct gggattacag gtgtgtgcca ccacacccag ataagttttc tattttagt   3840 agagatggga ttttgccatg ttggccaggc tggtctcgaa ttcctgatct catgggatct   3900
gcttgccttg gcctcccaaa gtgctaggat tacaggtgta aaccaccacg cctggccaag   3960
agatgcattt tcaataagtt acttttcatg tcttttgtg tgtttgtttg agacagggtc   4020
tccatctgtc atccaggctg gagtgcagtg gcacgatcat ggctcgtata gcttcaacct   4080
cctgggctca agcaatcctc ctatctcagc ctctggcgta gctgagacta caggtgcacc   4140 accccctgact aatttttgt atttgtttag tttagttttg tttcgttttt agagatgggg   4200
ttttaccgtg ttgcccgggc ttgtctcaaa ctccagagct caagtgatcg gcccatcttg   4260
gcctcccaaa gtgctgagat tacaggcacg agccaccgcg cctgaccaac ttttatgtt   4320 taatccttgt gaatattcct agttttggtt aactgcaata attgcaatac aaatagaata   4380
actgtttcta acacttgttc aagggcttgt tcacgtattt tttaaaagga tgctaacaga   4440
tatgaaagtt ctatggcatt atattcaatt tgctacactt agagtgacgt gcagtctccg   4500
acagactgag cacaacaaat tgtttttaat tttaaaaact gacatggcca ggcatggtgg   4560
ctcacgactg taatcccagc atttgggagg ctgaggtagg cagatcactt gaggtcagca   4620
```

-continued

```
attcaagacc agcctggaca atggtgaaac tctgtctcta ctaaaaatac aaaaaactta    4680
gctgggcatc ccagctactc gggaagctag ggcatgagga ttgcttgaac ctgggaggca    4740
gaggttgcag tgagccgaga tcgcaccact gcactccagc ctgggagaca gagtgagact    4800
ccatctcaaa aataataaat aaataaataa atacataaat agtgatgtga tttttaacat    4860
gtatttgcaa ttccctgaaa agcctaccct ttggaatgct attaaattat tacaaatgtt    4920
aaatgttgac ttaaaaatgt gcaaggggct gggcgaggtg gctcatgcct gtaataccag    4980
cacttcggga ggccgaatcg ggtggattgc ttgtggccag gagtttgaga ccagcctagg    5040
caacatggca aaactgtctc tacagaaaat ttaagaaatt agccagatgt ggtggcccgc    5100
acctgtagtc ccagctactc aggaggctga ggtgggaaga ttgcttgacc ctgggaggtt    5160
gaggctgtag tgagccaaga tggcaccact gcactccagt ctgggcaaca gagtgagacc    5220
gtgtctcaaa acaatacaaa tgtgcaaggg acatagtttt tcaaaatcct ttaaagaggc    5280
aatcaggtta gaaggacagg agctcagaga tcccaatggt ctactgtcaa tcaagtatcc    5340
gaccagggtt agggatgaag agggggttaaa agaaactgag gttgcataac cttaaatttc    5400
accacttaga acccagtttg cttatgtggt aactctcatt aaaaactaca tatgagaggc    5460
cgggcgcggt ggctcacgcc tgtaatccca gcacttcggg aggccaaggc gggcgaatca    5520
cgaggtcagg agatcgagac catcctggct aacatggtga aacccagtct ctactaaaaa    5580
atacaaaaaa aattagctgg gcatggtggc cggcgcctgt agtcccagct actcgggagg    5640
ctgagacagg agaatggcgt gaacctggga ggtggagctt gcagtgagcc gagattgtgc    5700
cactgcactc cagcctgggc gacagagcga gactccatct caaaaaaaca aacaaataaa    5760
aaaccaaaaa actacacatg agatcaggcg tggtggctca cacctgtaat cctagcactt    5820
tgggaggctg aggcgggtgg attacctgag gtcaggagtt cgagaccagc ctcaccaaca    5880
tggtgaatcc ctgtctctac taaaaataca aaaaaattag ctgggcatgg tggcgggcgc    5940
ctgtaatccc agcttctcag gaggctgagg caggagaatc cattgaacct gggaggcaga    6000
ggttgcggtg agccaagatc gtgccactgc actgcagcct gggcgacaga gcaagacccc    6060
gtctcagaaa acaaaaaaca aaaaaaaact acatgtggtc cgaatgaaac aaaactaagc    6120
ttagggttta ggaataatct gagaacacat aagaattgta ggttgagcct agtagaatta    6180
aataggcccc aagctggact ggattcaccc attcattcat tcattatctt acttcctcaa    6240
tgtgtccacg aatgccgggt gccatgggag aatataagaa tataaataat aaaaatatgt    6300
agtttctact cagaacttaa aattgagaga gacagaattt acaggcaagt ttaaataaca    6360
tcaaagacag taaaaatgca tatttcctaa taatgacatg agcgagcgcc aatgtaatag    6420
ccttggcagt aaacgccgtg agttcagaag agtcacggtg agctggacta gtcaggggag    6480
gcttctggga ggagggcccg gagcgggacc tgagagaaga acaggcagtg tgtctggagg    6540
atggaccagg aagggcagac ccggagcctc atacaggtgt caggtacaga agctgccccc    6600
aggtgatgag ctctcgtggc cagaaccacc agctctaggg accagccctt gcgcgtatgt    6660
gcatcagcct tcgtgtgtgc tgttccctat gtctggaatg gccgtcctct cccaaaccag    6720
ctgcatttct cctcagggat gcctctgcct acaccactcc ttcccgcacc ccacccgacc    6780
cccaacgccc ttcaccccag tcaccctatg gcaatgattt attcatgtct gtcttcccctt    6840 cccaggccat gaaccttgtg aggcagggac tgtgttctac gcatttcttc ttgaacccct    6900
ttaccatttt tgtgcctacg gactcccaga gtgctaaatc actcccaaca gccccgccta    6960
tgcctctgcc gggaccttttt ccaggggcag agagctggaa gcacttggaa attttttctct    7020
```

```
cccacatcct cacatgccac caccctccca ctcccccagc ccgccccag gccttaacca    7080
acggtggaca aatatgaagg tgtcagtacc ccagccctcc atgagactta gcttggttcc    7140
actcatgtgc ttgggtccca cttcccact ccctttccac tcctcccac cctcattact     7200
tttttttttt tttaagacag gtctcactc tgtcacccag gctaaagtgc agtggcacaa    7260
tcataactca ttgcagtctc aacctcctgg gctcaagtgg tcctcctgcc tcagccttct    7320
gagtagctgg tactatagat gcactccact cactgggcta atttttaat ttcttgcaga    7380
aatgatgtct tgccatgttg cccaggctgg tctggaactc ctggactcaa gcaatcttcc    7440
tgccttggcc tcccaaagca ctgggattac aggtgtgagc catcatgccc agtccctca    7500
ttactttat ttatttatt atttatttat tcaattttg agacggagtc tccctctcgt     7560
tgcccagact ggaatgcagt ggtgtgatct cagcccactg caatctccgc ctcctgagtt    7620
caagcgattc tcctgcctct gcttcctgag tagctgggat tacaggcatg cgccactatg    7680
cccagctaat ttttgtattt ttagtagaaa cagggtttca ccatgttggc caggctggtc    7740
tcaaactcct gacctcaggt gatctgcccg ccttggcctc ccaaagtgtc gagattacag    7800
gcatgagcca ctgtgcctgg cctatttatt tttgagacag ttctcactct gttgcccagg    7860
ctggagtaca gtggcacgat cacagctcac tgaagcctgg acctaagcga tcctcccacc    7920
taagcctccc aagtagctgg atcacaggcg catgccacca cgtctggcta atttttttg    7980
tagagattgg gtcttactat attgcccaac ctggtctcaa actcctgagc tcaagaaacc    8040
ctcctgcctc cgcctctcaa agtgttggga ttataggcgt gagccaccct gcccaacttc    8100
tcattagttt taaataaatc tcttttactt gaatctttgt ctcagggcct gcttctgggg    8160
aatccaacct aggatgcaaa gtatttgcta cacactattg caactacttt ctactgcgca    8220
tgtgccatag ggcactgttg gtaaatgctc tacagcttaa gctctcgttt aatttgcata    8280
acaatgctat catgatcatt tcacagaaga cagaaacagg cctagagagg tacagtgacc    8340
catgcaaggt cacacagggg acaaatggca gaactgggat ttcaatttag gtctgtgcta    8400
tgctaacaac actgatttta accactacat catcccagct cttttttttt tttttttttt    8460
tttttgagac ggagtcttgc tcttttcacc caggctagag tgcaatggca cgatcttggc    8520
tcactgcaac ctccgcctcc tgggttaaag caattctcct gcctcagcct cccacatggc    8580
tgggattaca ggcacccgcc accatacctg gctaatttt gtagtttttt tttagtagac    8640
acggggtttc accatgttgg ccaggctggt cttgaactcc cgacctcgtg atccaccagc    8700
cttggcttcc caaagtgctg ggattacaag cataagccac cgcgcctggc ccatcccagc    8760
tctttattca tctgtgtaac cctgacagag aatacagtgc ctgggccgtc atgcacactt    8820
aatgtgtgtt ttgtgaaagg ctaaattatt taatgaaggg cccaattaac aaagagtaga    8880
tcggaatgat tggagtaaaa taacccgaag aagagagaga catgttggag agacaggtcg    8940
ggggaaaatt agggaagatc ttggtgccaa gtgcaggagc tcatatctga aagtctctct    9000
cctctattag aactgtgcct gggcctgggc aacataacaa gaccctgtct ctgaacaaac    9060
aaaataagtt agctgaacat ggtagggcgc acctgtaatc ccagctattc cagaggctga    9120
ggtggaagat tgcttgagct caggaggtca agccagcct gggcaacaca gcaagacccc     9180
atctctaaaa aaaaaaaaaa ttaaaattaa aaagggcca ggcacagtgg ctcacacctg     9240
taatcctagc actttgggag gccaaggcag gaggatcgct tgagctcagg agtttgatac    9300
cagtgtgggc aacatagtgt gacctcacct ctacaaaaaa aatgtttaac atttggccag    9360
```

```
gttgccaggc gcagtggctc acgcttgtaa tcccagcact tgggaggcc gaggtgggcg     9420
gatcgcgagg tcaggagatc gagaccacgg tgaaacccg tctctactaa aaatacaaaa     9480
aaaattagcc gggagaggtg gcgggcgcct gtagtcccag ctactcggga ggctgaggta     9540
ggagaatggc gtgaacccgg gaggcggacg ttgcagtgag ccgaggtcgc accactgcac     9600
tccagcctgg acgacagagt gagactccat ctcaaaaaaa aaaacaaaca attagccagg     9660
ccatggtagt gcatgcctgt agtcccagct actcagcagg aagatcacct gagcatgaga     9720
ggttgaagct ggagtgagat atgattgcac cactgcactc cagcttggat gacagagctg     9780
tctcagaaaa aaaaaaaaaa ttgtgcctag ggtggggaga aacacataca tctctgggta     9840
tactgtggca ggaagctaag gatagaaagg aagaaggagg tctggacccc tcaaactgac     9900
cctcaagcca ataacgtgga attagttagg aggaaaaaaa attaattaat taattaattt     9960
tttattttt gagacaggtt cttgctctgt cgcccaggct ggacagtgca gaggtgcagt    10020
tacagctcac tgcagccttg acctcctggg ctcaagggat cctcctacca cagcgtcctg    10080
agtagctggg accacaggca tgtgccacca tgtccagcta agagaaattc ttaaagaaga    10140
gagaaaggag ggaaaggaac tgagcccctg atgttgtcta gggaaaaagc tggggctctt    10200
tacagcatgc tgccttcttt aattccacag cactatgtgg gtttccatgc ctttatttcc    10260
ttggaaagta tgagcttctt gaagacagca actgtgcctt gtctttcttt gtatcccttc    10320
cttctctcct agtacccagc ctagaaggca ctcaataaag caaatgatta gccccatttc    10380
acagacgagg aaccaacact gagagaggta actcacctgt gcaagtcata tcacaagtgc    10440
caaagtcaag actggatgga ggactgcctg gctgcaaacc aattcttccc aggctgacat    10500
ggcaggtagg tgagtgggaa agagaagggg gaggcataag gcaattggag attttagtac    10560
ctattaatag gcagtggatt ttggcactca acaggctgt cttcattagc tggggaggag    10620
actgagtggg cctggatggt atggaggtat ttgcacaggg aaacccattg tgctggctta    10680
tccattcaga ttagacaatg ctggttcctc tctacctgcc ttggctaagc tcacctagga    10740
gtaaatgccc cagggacacc gtcacgtcta tgtcaacaca gagtcacgga attaaataac    10800
agaataggat cacagattta cagaacaata gcccagaacc ttggacatga cagatagtta    10860
ttaaatgctt ggccaatgaa aaaaaaagaa cctagaacta gtatcacggt aaaatctaat    10920
tatacaagct aagttacctt gagaaagcac caggcacagc cctgagcctt gggcagcgaa    10980
tgatgtcttt ggactagaca gaagagatgg ttgtctgccc tgctttgaag ctctctggcc    11040
agggaaactc caaaccattc atttgttcat ccatttgccc acacaatcaa cattcattga    11100
gcatctgctc tgtggggtgc tatgtgatgg tgacagtccc aggaagcagt ttcagtcctc    11160
cctgccctca aggggctctg tgtttaggga ggacaaacat atacatcatg acaataaaat    11220
ttgataaaaa gttaaattag agaggggca aaccctgacg taggagccca ggagggactc    11280
ctaacttctc tgccaatttc atgtttcaaa attattagac ccaagactcg ctttggtata    11340
aacttaagct ctcttactgt acatttttct tctcctgcta atctttaatt aagtgcccac    11400
caggtgcctg gcactgaatc aaaactcaaa aaacttgctg aattaagcca aatgcacctc    11460
ctgtgggttt ttccccctaa tatcctcaga ggcagtaatc aattccctcc ccaaattccc    11520
cagtccccac cccatcccca cctttccttt gcagtataa tctcaactcc tgtgatgggg    11580
gcaggcagga tagcatggta gtgagatcaa cagactgtga cttgggttct tgtcgctact    11640
tagccattca ttctgtatgt gaccttggga tgggacttta gggggatttc tttaataacc    11700
tctaaactcc cgtgcaatgc tgagagccaa ggtagcggct ctcaggtctt gttccaagaa    11760
```

```
ctgccaccag agggcagcct agagactcct ctcaggtgtt ttcctccaga gcctttgctc    11820
tttccctcac taatgtcatc cactccctgg gtccaccatc aaggcacaca ggtgtccctt    11880
tagccgtcaa ggtgaccgtt ctaaggtgag ccaggcatgt gaggcgaggc gagacaggct    11940
ctgaagccct caggaaaatt caggcacagg ctgcttgtcc aagtggacct cacgatcatc    12000
atttacacat tctctccctg attatttcat gagccagcgg tctacaggag aggataccac    12060
agccagtcaa agggatcagg gccctgccct cagggagctg ccttccagtg agggaggaga    12120
gagatacaca gatgcttaca aggtatctgt agtaggatgt caccctagtga tgaatggtgt    12180 gacgcagctt aggcagagcg aggaaatagg gatggtccca aacgtgtgtg tgtatgtgtg    12240 ttttttttgag acagagtttc gctcttgtcg cccaggctgg agtgcagtgg tgcgatctca    12300
gctcactgca acctctacct cccgggttca agtgattctc ctgtctcagc ctcccgggta    12360
gctgggatta caagtgttca ccaccacacc cggctaattt ttgtattttt agtagagatg    12420
gggtttcatc atgttggcca ggctgggcta cgagcgaaac tccatctcaa aataataata    12480
ataataataa taataataat aataataata ataataataa ttcctgtctc ctagggtcat    12540
tgagagaatg gagatcagtc ctgcacgggc agacctcggc accgagctga atgttacaca    12600
ctgccaagga gtcggcgccg gtctctggtg aagatgttct agtcccaggg cccaagagaa    12660
cagagcggga cacgagatgc ctctctaaca ggagtctgtg tttcctggtc acctctgtgt    12720
gctgggtgat gcctcaggtg ccagggagac actgggcagt aggagaagct ccctcctgtg    12780
aggactctca cccagaggca ctcagacagc ccagaacaca ggagggaaga tgggccacca    12840
cagtcccatt cctaggcgct ccaagggcca gcccagccta gaagtccctc ctggtacaag    12900
tctttccggc ctctcctctc ccgagagcac gttcagactg caccctggcg ctctctttca    12960
ccctgtcgag gaagctgtga ctctaattct gggtgaccag taacaataaa aaccactaat    13020
agccctagtg gaaagaatga ctatttaaca ggtgcacata atgagcagac aaggagagct    13080
cttttccctc acactcactc cgcaggacag agagggaac agtcttgcta ctgtgacagc    13140
taatcacagc ctctgtgtgc ctccctcctc gcaagataag aggggtggcc tcagggtgtg    13200
acggaaacag ccaggaaggc ttcggccagg gagcgactgc cctacagctg actccctgct    13260
gcttttggga agtgggggtg aagggaaaag actcaggggga gcgggggaa gaaagcttgg    13320 tgggcagaac cccacttgcc aaattcctcc tctttcagga ttcagtggcc aaaggtgagc    13380
ctggctctgg ccccagtctt cactcccaag tgccggctgc agtgccctgg gcccgtcgga    13440
ggctggcagg gctgctggga gggtgaggac aggcatggga agagtggaaa gtggggctg    13500 acccagccaa gctccaggag gccattccat agaggagaga gccattggac caggagccaa    13560
gcagggaaga aggaaggaaa ggtagagccg agcaccgccc acaccaggaa taatctcagg    13620
aagaggatgg tgtggacagg ccccaggaca gggcttctca gctagggca actcgttatg    13680 ctgcagtggg ggcacctaac agaaccccct agggtttttt taaagtatac agcacggtcc    13740
tgcccaccac tggcatcaga tgaatgccat gtccagggga aacccagta cgtcctcatc    13800 acagccatgt gaacactgct gtttgttcat aaaaatgtgt tgcatcccta gggggaaata    13860
aaaggagcta atccaataga gagaagagtg gctcagggga gacagtcacc cgcgaggaat    13920
gagggcagga cacacaggcc caggccgaga ttgcacaggg tgttgcatga gtggctgtgt    13980
cagagccaag tgcacatgcc cactgccacc tccgccaagg ccatcagtga atccctccag    14040
cacctacagg ggctttgcac ataagagctg tgcttgcagg gggtgggggg tgggcacagg    14100
```

-continued

```
gcaggaaacc agagaggagg gcaccatgtc cctgagtaag gtagaaaggg aagcacagc    14160
ctggacacat tcttccattc ttttatttca aaatatcacc aagtgcctgc cacagctatg    14220
tgctgggaac tcagtgaacg cacctgtgct tgcccactg gcatggagcc cacggtccgg    14280
gggtgatggt ttctgttgca tttcaaagcc actgggcgc tgcatagatg gctggctgca    14340
gagtctattt gagacgaagg caagaagtca gggcccatgg actgtagatt ccacccttga    14400
tcgtctacta caggaaagaa gccacagaag tgaggggta ttcccaacag gaaggcagag    14460
aaggagagat taaaactgag tcaagaagtg tagccagtcc catgggagca cctgggctga    14520
ggagggtcag tccccgcaga gatgttcgga acacctgatt ggggatgtgc cctctccttc    14580
tatgttcttg gtcaccagag gaaccaggtg aagagtgtgg atgactcagt ccacccctcc    14640
ccgcacagga aaacaactc agaggacatc ccctactggg agtgggccag gagcgctggc    14700
ttccacgcca aggagaggag ggtgttgctg tggctgcaga ggtgagtcca cagggaagcg    14760
tgggtgtcat ggagaaagag agaggagagg aaatggcctc tcgctggagc caagcagaga    14820
ggaacaaagg aggggaggag cccacaggcc ctggagcccc agagcagctc tgggtggccc    14880
cttttccttct ctcctcagca caaaataagc tgcttttcca ggcttttct cttcctcgtg    14940
ctcactccat tttccttctt ccaagcctaa gccctggtct accaaggacc cctatgtgaa    15000
acacttgtgc tagaacttct gtcctgactc tcaggccccc agaggaggaa agctgtggag    15060
gagggacctc atgagccagt aaccttcact taggaactct tcactttttt tttttgaga    15120
cggagtctca ctctgtcacc caggctggag tgcagtggca tgaaatcggc tcactgcagc    15180
ctccgcctcg ctggttcaaa tgattctcct gcctcagcct cctgagtagc tgggattaca    15240
ggtgcctgcc cccgcacccg ctaatttttt gtatttttag tagagatggt tttgccatgt    15300
tggccaggct ggtctcaaac tcctgagctc aagtgatcca cctgccttgg cctcccagag    15360
tgctgggatt acaggcgtga gccaccatac ctggccagct tgacagcag aaatcttctc    15420
tctagaaata ttcatataca taaggaattt tgcacacatc cttacagggt ttagggagcc    15480
tcttaagcct gtccatgaac ctctgccatt catttatagc atggtgtcag ctgcagagta    15540
ataggatcta tgtgggcctg gaagtccaac aggcctgggt ttgaatcttt ttcaaacatt    15600
tttgcttgtt agcagctggt ttggacaaat aatttcaact tagttttctc atctgtgaaa    15660
caggggaaa aagcacttac cctgtagggc tgttgtgaag attgaacaag acaactcatg    15720
ttaaatacc aggcaccgtg tccgcctgca gcaggcagtc agtacatggt ggatctcgtg    15780
ccccaagcct cctctttatg gagtccctca agttgcccca gctggcctcg gattcctccc    15840
acctccacct cctgggtagc tgggactaca gcacgccatg cttcagcccc ctttgtgatc    15900
attcaaagcc gtttggttcc ctgcaccctc tcacatttac tgcaattcct atagaatcca    15960
aattctttta acctggtgtt gtaggtcatc tacaatcccg atccaagcag cctgtccctt    16020
ctcccacacc actgtcctcc acatgcatgt cccacaccaa cccacgccat ccgctggttc    16080
taaatacacc tgaagcacca caaggcccca cgtctggctg cctgctctgt gcttctctca    16140
tcattcctca aggcccgggg aaagtcctgc cacctccctg aagccaagtg cctacccgct    16200
tctccactct aggctgctct cttacgctgt gtgtccccag ctggatggca gctcctcagg    16260
gcaaggaaca atttctcttc tttctcagtg caacttccaa aacacagcag aggagcgtgc    16320
actgggggca aaggctggca cagcaaacac agcagcacag ggctgctgga ggggtggagg    16380
ggaccggagg ggacagtgac ctgcctgctt cataatacat ggctgggagc cccaccttt    16440
gcctatggaa gccatgtgct ttgagcttga ttttctcggg tgtagagtgt ctacgccacc    16500
```

```
cacactttct cacccggtcc aatgcacggg cacgggcagg ggcagggcca gaatctgttg    16560
ctgtagaaca cagcagagct gcctgcagta ctgtggacgt caccaaactg gcagcttcac    16620
tgaaggtgac cctggcctgt gtgggcactc agctgatgcc cttctcttcc ctcctaagcc    16680
ccattagctt taggtcttca ccacctgcac tgagagaaag attaatggtg agcaccagag    16740
taaaatctag cacagaaggc agggtttcag taaaaaacca aaagcatggc agattagagc    16800
tcaagggccc acaggtgggc aggacagtag aggaactggg cagcccaggg tggcaggatg    16860
gggtggacag gagtggacag gagagagtag ccaggaggag ggacgtggct gcaccaccag    16920
tccacgtggg cggctggaga cctggcagga ggccaggaga gactgtgcct cctccagcct    16980
ggctgtcttg gccaagttct gatggcagcc aggaggactg tgagaaagaa aacaagacaa    17040
actttgctac ctctggctgg tcaggggaag tttgtgttgg aaaagaagaa gccacagatt    17100
ccactgttcc gctgccttct cccctcacac cctgggacgg cccagcacct tctagtccac    17160
tcctccctgc cctctgccac tccctcact accccagtgc cccctccctc cttgcccagg    17220
tcctccaggg agccaagcct gagagtctag ggaggcccac aagaggaaat gatgttcgga    17280
aagagcagca tcactttatt ttttgagatg gagtttccct tttgtcaccc aggctggagt    17340
gcaatggtgc aatcttggct cactgcaacc tctgcctcca gggttcaagt gattctcctg    17400
cctcagcctc ccgagtagca gggattacag gcgcccacca ccacgcctgg ctaattttt    17460 tgtattttg gtagacgg ggtttcgcca tgttggccag gctgatctcg aactcctggc    17520
ctcaagtgat ccgcccgcat cggcctccca tagtgctggg attacaagcg tgagccaccg    17580
tgcccagccg agcagcatca ctttaaatgg tatctctgtc tcacatttgt gcctgcacct    17640
ctatacaagg caggaaggga gcagaagaca ctctgctagc attggctggg ctggagactc    17700
aggaaaggga gcctggggct gtggggtga agctggccta tttgtctccc ccagtggaag    17760
gatgaagaca ggagcacctg cagggctcca tttgctgggc ttcctactgg gggactgcac    17820
cccttgtccc atttaacctt tttgataatt tcccatttga tgttcacaaa aaccttgcga    17880
aataagtgtt atttaaaata cccccatttc acagatgagg agatggaagt tcagaaaggt    17940
ttgaagagcc gcccaaagcc aagaggttag ctgggacttg aacccacgtc atcttcattc    18000
tgaagccagt gttttttgtt tgtttgtttt tccaaggca ttagccccct tcaggggacc    18060
ctgtcctatc ccttcctctc tccacagctc cctcagcccc tctttcctcc cactcccatt    18120
ctgagtgtca ctagcaagtc aagagcaaga ctagatggca gccactagct gcacgtggcc    18180
aaccacatca ttacaattaa ttaaaattaa agctccaaat cttggtggt taaacttgct    18240 ccatgtggcc agtggctacc gtatcggaca gcacagacag gaaacatttc catcctcctg    18300
ctggtctgaa cttaaagggc ggtcaggagg tagagggaat gggagagacc agcccaaggg    18360
gcccagggac agagctgcct ttgtgaggag atgaggtttg ggaagtgagt ttgggtgagg    18420
ggagcagggg tgtctgaggc ctgggggagg agagggcagc ttgctggact gcaggcacc    18480 tccctccgat actgatactc ccgcaatact agtgagcaat taattggctg gggcggggca    18540
ggggccagag caggagggag gccaacgcaa tggaggagaa gccaccaccc tctcagcaga    18600
tggcagggct ccggttctcc tggcctcctt tcatcctttg aggacccggg agcctgcctg    18660
gccctcctcg acctgcccag agctggctgc tgcttcctgc tcgctcatcc agcccagggc    18720
cagcagatgg gctacgggc caccaccttc ccaattagcc ttcttagcct cttgctcacc    18780
cttgaggtct gggttaccag ccatggggag gggctgtgag tggcctgtga gtaaccaagg    18840
```

```
cccagctttg acagaggtca tcagcccagg cccctcccct ggctgagccc tggctcccag    18900
cacccccccc caccccgcc accatgccgt cccagaggc cccagaagc gacaggtcag      18960
ggagttggtt ttgggaatgt ggtgcccat ttctgagaag gagaaggttc cccaggtgat    19020
ggaacacgta ataggtatgt ggctggcctg gtacttgggg agtggtggga gggggagcct   19080
ggggatggg ggcagaactc atatttgaag gaggaaagtg gaggtggagt gatgggtcc    19140
taaggaagga gcagatcagg ggctgtgaat gggacctcat tggggttggg tggtggggc    19200
tggagcgggc acccaagtgt ggaagaaaaa gctgaaacac ccacgactgc gagtggaggg   19260
cagatggaga gacaggccaa gccacggtag gcaggagagt taaggagcca ggcagctggg   19320
tcccgtggca agagtggccg ccccagagtg ggtggccgtg gggcagagcg cctggttccg   19380
ggttaggcaa tgaggagccg gggccaggcc tgtcaggtgg caggatcgtt agagcccgt    19440
ggccatgggt accccacact gcagccactg ctgctgctga gtaggcagat gcaccgggct   19500
gattaccacg ctcctcccgg ccacaccaac ttccccgggg gcacccaccc cctccacctc   19560
tcctcctctc cccacagtga ctcctgccca gggaatgtcc agctctggca taaaggaccc   19620
aggtgtcctc gagctgccat cagtcaggag gccgtgcagc ccgagatggg ctcgtctcgg   19680
gcaccctgga tggggcgtgt gggtgggcac gggatgatgg cactgctgct ggctggtctc   19740
ctcctgccag gtaggaggct gggggccctg gaacaggag ggaggcggga gggagactcc    19800
gggagaggac ccagcgaagg ggacgggcag gggctctgga atctgccttt tgagtctggg   19860
ggttgctcct cactgtatgg tcgcctcagg taagtttctt aaacttcctg agccccagtt   19920
tctgaaattc tgaagtgggg ttaatgacac ctacctctag tctgtgtgtc tcaaattaaa   19980
taatgtatgt gatatgtact ttggaaattc tagaggttta tataaatggt ggtggtgatt   20040
tttattatgg gagcactaca agataatgat tggacattta atagtaataa tatcattttt   20100
agagcctttt tatatgctag actctgtttt aagcacattt ggattatata ttagaacttt   20160
tattttatt ttttttgtga gatggagtcc cactctgtct ccaaggctgg agtgcagtgg    20220
cgtaatctcg gctcactgca acttccacct ctcaggttca agcgactctc atgcctcagc   20280
ctctagagta gctgggacaa caggtgccca tcaccacacc tggctaattt tctttttttt   20340
gtatttttag tagaaacagg gttttaccat tttggtcaag ctggtcttga actcctgact   20400
caagtgatcc gctcgcctcg gcctcccaag gtgctgggat tacaggcatg agccaccaca   20460
cccggcctat attagcactt ttgatcatta caagaacggt atgaaaagag atttgctatt   20520
tccactctac agatgaggac actgaggctc ggagaggtta ggaaactagc tcaaaatcat   20580
gcattagaag gcagcaaagc caagatttca accccaggcc aggcaacccc tggacctgtg   20640
ttgttgacca ccgggtactt atagcccttg aggaatttct gcgaccttcc catggtctag   20700
tgggtggttg gtgtctgagg gaatagcgaa agagagaggc aatgcatggt ggattcgtgc   20760
agaggactga agggaattgg cacagctggg gttcggcgtg gaggtgcatg cagagaattt   20820
ctttctgagg agagaacagg gacatcacag aggatggcag tctggttgtt ggtggaggga   20880
tcaggatgag tggcagtaat aattcataat atataatgct ttacactttc taaaacatct   20940
ggccgcacat gatagcttgt gcctgtaatc ccaacacttc aggaggccaa ggcaggtgaa   21000
tcgcctgagg tcaggagttc aagaccagcc tggccaagat ggtgaaaccc cctctctact   21060
aaaaatacaa aaaattagct gggtgtggtg gcgggcacct gtggtcccag ctacttggga   21120
ggctgaggca ggagaatcgc ttgcaccaag gaggcagagg ttacagtgag ctgagaccgt   21180
gttattgcac tttagcctgg gcaacaagaa actccatctc acaaaaaaaa aaaaaaaaa    21240
```

```
aaaaaagaag aaaaaacttc caggtggatg atctcatttca gttttcttca tagtaatgct    21300
gtgggaaggc agggaaaatt tggcccctct gaatgtataa actaaagctc agagaggttc    21360
agtaacttgc tagtatgtgg ctctgtttgt aacacgtggg acctggaggg gctagggaag    21420
gcagaaggaa cgcaggtgaa agagtcatgg aggaaccatg gggtaagttg ggcctggggt    21480
tttgagcaaa ggaaaggaaa gataaggaaa gatgtggctc cacatccctg agggaagtca    21540
aggcagcaga agtcagatga ggggctggac agaggcaggt gtgctcagag agggaagctg    21600
attgtggcca ggagcctcgg aggttcgtgg ggtttcgtcc tggttccctg ggctgggcca    21660
gcgagagcag ggctggctca gggtgcggtg tcctgacaca ctggtaccag caggttctga    21720
agcaacaggt agtgacccca catcctggcc cccacccagc tttactggca tggccagtgc    21780
tgagatagga aatagggttt ccattcctga ccccagcctg ggctctcacg aagaagctgg    21840
tgaccaaatc ttagtcctcg agtgcccttt cctttatttc agccctctg ccccagctt     21900
tgtcttttcc cagtgtctcc ttctatatgt gtctccactt ctcagccctc cattgttttg    21960
cctttttgtct tcttccctct ggtcccactg tctggcccag gattttccc ctaagaattt    22020
acgcctggac tcctcagagc ctcagtttcc ccaattctct gtctcttcag ggtcctttct    22080
tttagaccta tttgttcctg ccccttctcc attccctctt cttttttaaaa aaattttaa    22140
ttaaaaaaca aaatacagat ggggtctatg ttgcccaggc tggtcttgaa ctctggggcg    22200
catgcaatcc tcccacctca gcctcccaaa gtgctgggat taccggcgtg agccactgtg    22260
cccagccccc tcttatattc aatgtattcc tttgaggtca ctcactttgg cacgtaattt    22320
tctatttttc tggttggtgt ttgcccaccc ttcccaaaca agaaatgcc tttattcggc     22380
cacctcaata tccttttagag acaatagcca gttcttcctc ctttctccat ccctaaactc    22440
tccctgcgct ctgcttggga gaaacccgag aggccgatta ctgagataag gcagaaaggt    22500
gagggaggaa gccaagcctc tttggcccct actaaccact gctttcctcc acagggacct    22560
tggctaagag cattggcacc ttctcagacc cctgtaagga cccacgcgt atcacctccc    22620
ctaacgaccc ctgcctcact gggaagggtg actccagcgg cttcagtagc tacagtggct    22680
ccagcagttc tggcagctcc atttccagtg ccagaagctc tggtggtggc tccagtggta    22740
gctccagcgg atccagcatt gcccagggtg gttctgcagg atcttttaag ccaggaacgg    22800
ggtattccca ggtcagctac tcctccggat ctggctctag tctacaaggt gcatccggtt    22860
cctcccagct ggggagcagc agctctcact cgggaagcag cggctctcac tcggaagca    22920
gcagctctca ttcgagcagc agcagcagct ttcagttcag cagcagcagc ttccaagtag    22980
ggaatggctc tgctctgcca accaatgaca actcttaccg cggaatacta aacccttccc    23040
agcctggaca aagctcttcc tcttcccaaa cctctggggt atccagcagt ggccaaagcg    23100
tcagctccaa ccagcgtccc tgtagttcgg acatccccga ctctccctgc agtgagggc    23160
ccatcgtctc gcactctggc ccctacatcc ccagctccca ctctgtgtca ggggtcaga    23220
ggcctgtggt ggtggtggtg gaccagcacg gttctggtgc cctggagtg gttcaaggtc    23280
ccccctgtag caatggtggc cttccaggca agccctgtcc cccaatcacc tctgtagaca    23340
aatcctatgg tggctacgag gtggtgggtg gctcctctga cagttatctg gttccaggca    23400
tgacctacag taagggtaaa atctatcctg tgggctactt caccaaagag aaccctgtga    23460
aaggctctcc aggggtccct tcctttgcag ctgggcccc catctctgag gcaaatact     23520
tctccagcaa cccccatcatc cccagccagt cggcagcttc ctcggccatt gcgttccagc    23580
```

```
cagtggggac tggtggggtc cagctctgtg gaggcggctc cacgggctcc aagggaccct    23640
gctctccctc cagttctcga gtccccagca gttctagcat ttccagcagc tccggttcac    23700
cctaccatcc ctgcggcagt gcttcccaga gccctgctc cccaccaggc accggctcct     23760
tcagcagcag ctccagttcc caatcgagtg gcaaaatcat ccttcagcct tgtggcagca    23820
agtccagctc ttctggtcac ccttgcatgt ctgtctcctc cttgacactg actggggcc     23880 ccgatggctc tccccatcct gatccctccg ctggtgccaa gccctgtggc tccagcagtg    23940
ctggaaagat ccctgccgc tccatccggg atatcctagc ccaagtgaag cctctggggc     24000
cccagctagc tgaccctgaa gttttcctac cccaaggaga gttactcgac agtccataag    24060
tcaactgttg tgtgtgtgca tgccttgggc acaaacaagc acatacacta tatcccatat    24120
gggagaaggc cagtgcccag cataggggtt agctcagttt ccctccttcc caaagagtg     24180 gttctgcttt ctctactacc ctaaggttgc agactctctc ttatcacccc ttcctccttc    24240
ctcttctcaa aatggtagat tcaaagctcc tctcttgatt ctctcctact gtttaaattc    24300
ccattccacc acagtgcccc tcagccagat caccaccct tacaattccc tctactgtgt     24360
tgaaatggtc cattgagtaa cacccccatc accttctcaa ctgggaaacc cctgaaatgc    24420
tctcagagca cctctgacgc ctgaagaagt tataccttcc tcttcccctt taccaaataa    24480
agcaaagtca aaccatcatc tggaaacagt ggccactttt cactgacctc tcttcgacat    24540
ctagtcaacc cacccaatat gccactgggc tttcgctccc aattccaccc caccctccat    24600
tacagagctc accacgccct cctagatcac cgtccccaac acacccattg cctctcaagg    24660
cccttatctc agccccttcc tgtggccatt tccctcagtg cccagatgat tccctgggtg    24720
agggagacac tggggcaccc tcagaggttg gagcaggctc cctgctgtcc ctggatcctg    24780
gacagatggc tcagtaaact gtggggacta ggtgcagact ttttgccttc ttggagtcct    24840
gggtctcctc tgagagtctg ggtggtgctc ttcctacgcc tctagaggtc tctgtgtccc    24900
tcattttcct tcaaaagcgg gctgtgtttc tcttctacct tccagctcct cccacagagg    24960
aggaagacaa taaatatttg ttgaactgaa agcagagatt gcctggcctc ccagatcctt    25020
ccgccatttc cctcctctct cattgctcca ggaaatccat tctcttccca ttcctcattc    25080 accgtgggggt ccccccttccc cttatttagg gccctcagtg ttttctctcc ctcccctccc    25140 ctccctccc cacccaaact ccttttcttc caccattagc attcctcacc ttctagatgc      25200
catcctctct gggagtcatg agtctcgatt tcctg                               25235
```

```
<210> SEQ ID NO 3
<211> LENGTH: 14483
<212> TYPE: DNA
<213> ORGANISM: Homo sapiens
<220> FEATURE:
<221> NAME/KEY: exon
<222> LOCATION: (1)...(174)
<220> FEATURE:
<221> NAME/KEY: exon
<222> LOCATION: (2121)...(2424)
<220> FEATURE:
<221> NAME/KEY: exon
<222> LOCATION: (5808)...(5971)
<220> FEATURE:
<221> NAME/KEY: exon
<222> LOCATION: (6070)...(6205)
<220> FEATURE:
<221> NAME/KEY: exon
<222> LOCATION: (6365)...(6475)
<220> FEATURE:
<221> NAME/KEY: exon
<222> LOCATION: (6715)...(6864)
```

```
<220> FEATURE:
<221> NAME/KEY: exon
<222> LOCATION: (8203)...(8313)
<220> FEATURE:
<221> NAME/KEY: exon
<222> LOCATION: (8420)...(8526)
<220> FEATURE:
<221> NAME/KEY: exon
<222> LOCATION: (11115)...(11227)
<220> FEATURE:
<221> NAME/KEY: exon
<222> LOCATION: (11430)...(11475)
<220> FEATURE:
<221> NAME/KEY: exon
<222> LOCATION: (11620)...(11756)
<220> FEATURE:
<221> NAME/KEY: exon
<222> LOCATION: (11850)...(12038)
<220> FEATURE:
<221> NAME/KEY: exon
<222> LOCATION: (12135)...(12236)
<220> FEATURE:
<221> NAME/KEY: exon
<222> LOCATION: (13510)...(13663)
<220> FEATURE:
<221> NAME/KEY: exon
<222> LOCATION: (13789)...(13960)
<220> FEATURE:
<221> NAME/KEY: exon
<222> LOCATION: (14207)...(14483)

<400> SEQUENCE: 3 gccccttca actctgccaa gaatggctcc cacctggctc tcagacattc ccctggtcca      60 accccaggc  catcaagatg tctcagagag gcggctagac acccagagac ctcaagtgac     120
catgtgggaa cgggatgttt ccagtgacag gcaggagcca gggcggagag gcaggtaggg     180
atccatccac gccgttttct caggcttgct tgctagtgac ccttcctcac tggaataaac     240
tccttaccct atttcggccc tagtttccag aacgtactca ttttatgta agcaattagt      300 tcctacagtg cataaataat aaagcagtgt gctaagtgct agggatgagg ataacaatag     360
tgaataagac aaatcctgac ttaaatttgt aattaataag gaatctaaaa tcctaagagg     420
ggagatagat tgaccaccag ctgatggtaa agcatggtat gaggcaagat gaagaagtgc     480
aaactagagg tagagaccca gcactgtggc agtgtgggtt cattctgatg gaagaaagcc     540
tttacagagg acatgctgtg ggagctggcc atgctgtcgt attatctgta acattctta      600 ttcttgtttc atgtgtcttt tcccagatgt actgggatat cattctgcca ttttgctcca    660
gaataggatt acattagaag aagcagcatg atgaagaagg aatactagac tgggtgtcag    720
gagacagaga ctctatttct agtttggcta ccagctagag gacatttggc aagtcactta    780
atttccctag cctacagatc gctgctacta aagaaaagaa agaaagagcg agccagatat    840
ggcggctcac acctataatc ctagcacttt gggagctgag gcaggaggat cacttgagcc    900
caggagttca tgaccagcgt gggcaacaaa gcgagactcc gtctccacag aaaataatta    960
gctggctgtg gtggcatgca tttgtagtcc tagctactca ggaggctaag gtggtaggac    1020
cccttgagct cagaagttga agactgcagt gacctatgat ccagccactg cattgaggcc    1080
tgggtgacac agtgatacc  tgtctctaaa aacgacaaca acaacaatct cttatagtcc    1140
tgggtctcag agagctgcct caggagccat gttccaagct ggattaaact tcacgtgaca    1200
ttggtagacg atttctctaa aggctggcac tgtgttattt atgtactgtt ctctcagact    1260
cctcataaag tatacctaac actcaataaa tgccttttt ttttttttt tttttgaga     1320 tggagtctca ctctgtcgcc caggctggag tgcactgggg agatcttggc tcactgcaag    1380
```

-continued

```
ctccgcctcc caggttgacg ccattctcct gcctcagcct cccaagcagc tgggactaca    1440
ggcacctgcc accacgccca gctagttttt tatattttta gtagagatgg ggtttcaccg    1500
tgttaaccag gatgatctcg atctcctgac ctcgtgatcc gcccgcctcg gcctcccaaa    1560
gtgctgggat tacaggcatg agccaccgcg cccagccaat aaatgccttt taactagcac    1620
ctggcctcac catattgata ctggaagctt acgacctctc tatgcccatt cctccctcaa    1680
acttcttgcc cttaaattag aattgagaag tccctgtgtg ttcttccaac ctttccactt    1740
aaaatgtgtg gcctaaaaat aaaaaaataa ataagacaaa aaaaccacca aaaaacaaaa    1800
agaatgtgtg gcctaatgat atacacattt gatgttgaat cctcctgtat gtagctctct    1860
ctagggagat catgttccac gatctcagcc agactttagg tcctgtgagt ccaggcactg    1920
gactcaacat gctcaatagg gctttgatga atgatgatga tgtcaatgca gacatcccca    1980
taccccagct tcagcacccc cttcacctcc ccacacggaa gcagagggt cctcttttcc      2040 ttctcctggc tatgttatg ccctcaacta tccttccagc actggagaca gtctccacct      2100
gcactaacct gtctttgaag gtcctggggg ctggaggggt cacaggccct gagccagcag    2160
gctgaggtga tcgttcggca gctgcaagag ctgcggcggc tggaggagga ggtccggctc    2220
ctgcgggaga cctcgctgca gcagaagatg aggctagagg cccaggccat ggagctagag    2280
gctctggcac gggcggagaa ggccggccga gctgaggctg agggcctgcg tgctgctttg    2340
gctggggctg aggttgtccg gaagaacttg gaagagggga ggcagcggga gctggaagag    2400
gttcagaggc tgcaccaaga gcaggtgaat gcagggtag aaaggattca aattcataac     2460
ggagagctgg gcagtagctt ccaagcaaag aacaggtatt gcagaaaaga ccctccatga    2520
gtagtgagta gtagagtgat gagaccttg gtgaaaataa acacacatgg gctagaaaga     2580
tggagaattt gggtactttt atcttaattc aggttgcact tttcccccaa gactcaggtg    2640
gcctcccacc acttgaagcc ctgcttccct ttctagtagg aaatagtttg cctccctact    2700
ttactccagg taccaattca tcaggggtat tgtggagggc agtgaggaag gtgggtataa    2760 ggggctatg gtggactggg agagagagat tattcagtcc tcaaactcag tacttactct      2820
gccatctcta agactcagtg accaaattag cctgagtcct gccttcgtgg atggaactga    2880
cagcctcgtg ggggatatac acatccacat ttaatttaat cataattaat tgcaatcagg    2940
aggaatgcct tgaaggagaa ggactagaaa gcactaactt agtctggggt tcagggaagg    3000
ccactgtaac cagttgacat gtcaaggaaa gaaaccatag ccctgggcgc agtggctcac    3060
gcctgtaatc ccagcatttt gggaggccga agcaggcaga tcacaaggtc aggagttcaa    3120
gaccagcctg gccaacatgg cgaaaccctg tctctactaa aaataaaaaa attcaccagg    3180
catggtggtg cgcacctgta atcccagcta cttgggaggc cgaggcagga gaatcacttg    3240
aacctgggca gtggaggttg cagtgagccg agactgtgcc attgcactcc agcctgggcg    3300
acagagcaag actctgtctc aaaaaataaa ataaaaagg aactgggaga aaacaaggga     3360
gaattccttt ataaccttgt agtgggcaag gcctttctac ctgtgagtca aaatccaaaa    3420
tctagaagcc ataaggaaa aaattgatcc attgacttta taacatgaac attaggaata     3480 gccaaaaga aaaaaaaag ctatatttat agctcagatc acaagaaaag ggtaatatcc      3540
ctaatataaa atgtgtgcct agaaattggt aagggaaaga ccagcaatcc aatcagaaaa    3600
tggacaaagg agatttatga agaaacttga gaacaagaa gctaggccag gcacagtggc     3660
tcatgcctgt aatcccagca ctttgggagg ccgaggtggg cggatcactt gaggccagga    3720
gttaaagacc aacctggcca acatgaagaa ctctacaaaa aaatacaaaa attagccggg    3780
```

```
tatagtcgtg ggcgcctgta atccccagc ttcttgggag gctgaggcag gagaattgct   3840
tgaacctggg agacagaggt tacagtgagc tgacatcaca ctccagcctg ggcagcagag   3900
cgagactaaa aaaacaacaa gctaccgttt gtgctgaata ggagttggcc agtgaagagg   3960
cgtgtgaagt ccagtggtag ctggaagaca cttggtggga caacaggtga aggcggggac   4020
aggaggccag aaggctgggg cacagagatg agggggcactg agtgtgctgc agagcccagg   4080
acccagggca caaggctttg gccacttcag aacttgctac tttcccataa gagcaatgag   4140
caggctgggc acagtggctc atacctgtaa tcctagcact ttgggaggcc aaggtggaag   4200
gatcatttga gcccaggagt ttgagaccag cctgggcaac aaagcgagac ccccatctct   4260
attttatgga agaaattagg gctgggcatg gttgctcaca tgtgtaatcc tagcactttg   4320
ggaagctgag gcgggtggat cacttgaggt caggagttcg agaccagcct ggccaacatg   4380
gtaaaaccctc atctctacta aaaatacaaa aattagctgg gcgtggtggc tcatgcctgt   4440
aatctcagct actcgggagg gtgaggcggg agggtgaggc aggagaatcg cttgaacctg   4500
ggaggcagcg tttgcagtga gctgagatcg tgccattgca ctccagtcta ggcaacaaag   4560
tgaaactcca tctccaaaaa aacaaacaaa aaaaaattgt tttttcaagt aataagcaac   4620
cgttgaaagg ttgtttttt ttttttttga gatggagtct cgctctgtcg cccaggctgg   4680
agtgcagtgg cgcgatcttg gctcactgca agctccgcct cccgggttca tgtcattctt   4740
ccgagtagct gggactacag gcgcccgcca ccacgcccag ctaattttttt gtatttaat   4800
agagacgggg tttcaccgtg ttagccagga tgatctcaat ctcctgacct tgtgatccac   4860
ccacctcggc ctcccaaagt gctggaatta caggaatgag ccactgcgcc cggcctgttg   4920
aaaggtttta agcagggaaa taacatgatt agatttgtat tttatgtcta aaaaatttg    4980
tcatttatgt ccccaaaatt aattttattg ttgtatggag acagggctag aggaggcaga   5040
ccaggaagca gggtgggcac tttgccctcc tttccagtcc atcccatgac tcttggtggc   5100
tctgacaccc ctgcaacact ttgaggtgcc atgagcaaaa gacacaaaat tcctccttc    5160
ctggagcttt ccttccagtg tggtccgaca gatagtaaca catacacata agcaagatat   5220
ggtcagtgct aagtgctcag gaggacgtga acagctgatg gggcagagta gggtggggag   5280
ggacagtatt agagggccca gtgaagccac cctgaggagg ggctatcgcc tgggtctgt    5340
ggagcaagga ggggccgctg tctggttctc agcagactcc ccgtggccgg agcggggagc   5400
agtgggagag cctccagggt gagctcagga ggtaggcaga ggccgggtcc cctggcctgc   5460
aggtgtggag agacacctgg gttttgttgt gaatgctgtg agaagccact gagggtttgt   5520
aaagactagt taggagatgg tcgctgttgc ccaggcaaaa gatgagggtt ggtggcagtg   5580
gagacggaga cagagaggtg aagatatgtt ttgggggaga tcggacaaga actcctgatg   5640
ggttgtgggg cagctgcgga gagtgagttg ccagctctcc atttgctgtg cacagttggc   5700
tgattggttg ggtcattctc taaggtcaca gaaagtggga gtgaagggaa caaggaaggc   5760
ctccatgtgg ggtcgagcct ctgctgagcc ccctcttctt tccgcagctg tcctctttga   5820
cacaggctca cgaggaggct cttccagtt tgaccagcaa ggctgagggc ttggagaagt    5880
ctctgagtag tctggaaacc agaagagcag gggaagccaa ggagctggcc gaggctcaga   5940
gggaggccga gctgcttcgg aagcagctga ggtaggtggg cggacgccga cgggagccca   6000
gcaattagtg atgtggtgga tctgcagggc gccccactga tggctgtccc attcccaccc   6060
caaccctagc aagacccagg aagacttgga ggctcaggtg accctggttg agaatctaag   6120
```

-continued

| | |
|---|---|
| aaaatatgtt ggggaacaag tcccttctga ggtccacagc cagacatggg aactggagcg | 6180 |
| acagaagctt ctggacacca tgcaggtgag ggtgcaggaa tgtatctgtg tgcagactta | 6240 |
| gggatcaggt tggaggcaa gcgtggccct tggaggagcg tgtagagcac agcctccggg | 6300 |
| agagaaggtg gtacctaagg cggcatggag gccctacaga ggggctgctt tcctctgccc | 6360 |
| gcagcacttg caggaggacc gggacagcct gcatgccacc gcggagctgc tgcaggtgcg | 6420 |
| ggtgcagagc ctcacacaca tcctcgccct gcaggaggag gagctgacca ggaaggtaca | 6480 |
| gcccaacccc cagaccctc accctcagcc gcatcctgca tctactgtcc cctgcctccc | 6540 |
| tccctgtggg caggaggggt caatgtgccc cagaacctgc ttagatctcc ttcctgtgaa | 6600 |
| ctcctcttgc tgtagctcat gttgcccagg caggacagag gagaaacaaa gatgccacct | 6660 |
| ccttcctctc ctccccagg agcccacact tttctcccac tccttctccc tcaggttcaa | 6720 |
| ccttcagatt ccctggagcc tgagtttacc aggaagtgcc agtccctgct gaaccgctgg | 6780 |
| cgggagaagg tgtttgccct catggtgcag ctaaaggccc aggagctgga acacagtgac | 6840 |
| tctgttaagc agctgaaggg acaggtcact gcactctctt ttctcccggt attccctccc | 6900 |
| agcaccttgc tccttccatg aaggtggcat ccattcaacc agtgtttatt gagtggttgc | 6960 |
| cacatgctgg gcacacagcc ctgaacaaaa ctaaaatgtg gagcttgcat tctagaacag | 7020 |
| agacacagaa cacgcaagta aacagataat gttgggtaat tatatgtgcg atagaaagat | 7080 |
| tgaagccggg tgcagtggct cacacctata atgcgatcac tttggtctcc aactcctgac | 7140 |
| ctcaggtgat tcacctgcct cagcctccca aagtgatggg attacaggtg tgagccaccg | 7200 |
| tgcccagtca agtaatgcca acagtttggg agaccgaggc aggtggatca ctggaggtca | 7260 |
| ggagttcgag accagcctgg gcaacatgtg aaatcccgtc tctactaaaa atacaaaaaa | 7320 |
| ttagccgggc atagtggctc attcctgtag tcccagctac tctggaggat gaggtgggag | 7380 |
| gatcacctga ggctgggagg tcgaggcgag gccacagtga actgtgatcc catcactgca | 7440 |
| ctctagcctg ggtgacaaag cgagatcttt tctcaaaaaa aaagaaagta gtaagaaaaa | 7500 |
| ttcaaaagat aatgtgacgg agagactgtg gggtgagtca gcctcaggta ggatgctcag | 7560 |
| agacagcctc tctgaggagg tgacagcatc tgaggagagt ggcatggtca gttggtgggt | 7620 |
| cttgtgggt gtgtcaaggg ctattcccat cttcgagtgg gcacatggaa tgtgaacat | 7680 |
| ggaacactgg gctcagattc catcctcaga acctaagctt ctgtctccct gcgtggcatt | 7740 |
| cattcttttt cttttctttt cttttttttt tttttttga gaaggagtct tgttcttgtc | 7800 |
| acccaggctg gagtgcagtg gcctgatctc agctcactgc aacctcgcc tcccaggttc | 7860 |
| aagtgattct cctgcctcag cctcccgagt agctgggatt acaggcacat gccatcacgc | 7920 |
| tcagctaatt tttgtatttt tagtagagac aggctttcac catgttggcc aggctgatct | 7980 |
| tgaaccctg acctcaagtg atccatctgc ctcggcctcc caaagtgctg ggattacagg | 8040 |
| tgtgagccac cgtgctgcga cccaccccg tcgcccgccc tccctccccc cagccctgc | 8100 |
| atggcattct tacagagatc tctgcacctg ccactttgct tccagtgccc ccctcatctt | 8160 |
| ttagctctag agggccctgc ccagctctct ctcctccccc aggtggcctc actccaggaa | 8220 |
| aaagtgacat cccagagcca ggagcaggcc atcctgcagc gatccctgca ggacaaagcc | 8280 |
| gcagaggtgg agtggagcg tatggtgcc aaggttggtg tcagcctact agagactcgg | 8340 |
| ggagggcaag ggagcccctg ttccggggct gcagccagga cttagggagg gaccctgtcc | 8400 |
| tttgctgcat cctccccagg gcctgcagtt ggagctgagc cgtgctcagg aggccaggcg | 8460 |
| tcggtggcag cagcagacag cctcagccga ggagcagctg aggcttgtgg tcaatgctgt | 8520 |

```
cagcaggtat cagggatgga ggggtgggtg gagtagtgtt tctgccacct caggttcctg      8580
ggcaccttgt tgctgaggat cctcaggcaa gaggggctgg aaagtggcca ctggaggcta      8640
cagggctggg cagatttagc tctatcaatg ttcctgtgtt cgtttctttt cctggggaag      8700 cccttctgc attcatacct gattgcttgt tatgaatttc ccgttgcatg tttggctgga       8760
ggtgaggcct tgcttcctcc tgcagttcag tctagtaatg gcttgagcta atagagcac       8820 ccgggaggat cttcacttgc agtattgttc aaggatggag agtgtagaca cttcatcttc      8880 ctttttttt ctaaaatttt acgggcaatc cgtttcactg agaaaaatt tagtctattt         8940 atttatttat tttgagacaa agtctcgctc tgtcacccag gctggagtgc aatggcacaa      9000
tcttggctca ctgcaacctc acctccctgg ttcaagtgat tctcctgcct cagcctcccg      9060
agtagctgga ttacaggcat cctccaccag tgtcctccac tacgcccggc taattttgc       9120 attttagta gggacggggt ttcaccatgt tggccaggct ggtcttgaac tcctgacctc       9180
aggtgatcca cccacctcag cctcccaaag tgctggaatt ataggtgtga gccactgcac      9240
ctggcctagt ctatttattt aaagctgtat acttacttgc ttattatata cttaacttgc      9300
ttactattcc atctaaaatg taagccagtt agtttccttc taaatcaatt gccagccttt      9360
gtctctccta ccaacttcct agttgtttca ttacctacaa ttgttgtatg accttcagaa      9420
aaacctctaa gaaaacagca aagcttcttt gtgctggtga tgacttcccc tcagccttag      9480
acactgaggt acccaaggca agtagttctt tttttttttt tttgagacag agtctcgcac      9540
tgtcacccag gctggagtgc aatggcacga tctcagctca ctgcaacctc tgcctcccgg      9600
gttcacacga ttttcctgcc tcagcctcct gagtagctgg gattacaggt gcacaccacc      9660
acacccggct acttttttgt attttagta gagacagggt ttcactgtgt tggccaggct      9720
ggtctcaaac ttctgacctc gtgatccgcc cgcctcggcc tcccaaagtg ctgggattac      9780
aggcttgagc caccgtgccc ggccggcagg tagttcttag cacagtctct ggcttgtaaa      9840
tgtttattgt tatcgtgagg ctcttcttga tgggttaatt tagataaaga taattttgg       9900 tttagcgaaa ttaagatgca ggatgagtcc ttgcccacca cttccttctc ttgggtttgt      9960
accttaggga ctaatttagc tttaaaaatt atgaaaaatt tcaaacttgc acggaattaa      10020
actagttata atgacctacc acccaggttc aatccatcgc gggtgccccc tacctccagg      10080
agaacagaaa gatgcactgt ggacagggtt tgactttggt accaggtgat cacagaaatg      10140
gtctgtgtaa tgatgcatt gccgaaagtc ctccaggctt aaagcagtcc aaactctgat       10200
tgttgctggg tttattagat tgtctctagg taattggaga ctttaataag agctgtggta      10260
ggtgttggaa gcatctactg gaacaatttc cagatcaaag tgaactttgc tgtgctgctg      10320
gggatgcagc tgcaagcctt catcatcatg tgtttttctg tgggtgcaga cctggactct      10380
cctgaggaaa cccagcccg gccccagaca ctccttggcc tcctcctggg gcctgtttaa       10440
gctgctcagt tttcatgagc caggttggtc ctacttctgg cacagccagc tggtaaagca      10500
tgtggacctg cccgtcattg gtgctagatc gacactcctg ggcttggaga ggataacttt      10560
gttttctttt gttttttttga gatggagtct cgctctgtca cccagtcttg agggcagggg      10620
tgcgatcttg gctcactgga acctccacct cctaggttca gtgattctc gtgcctcagc        10680 ctctggagta gctgggatta caggcatgag ccaccatgcc cggctaattt ttgtgttttt      10740
aagtagagag agtttcacca tgttggccag gctagtctcc aattcctgac ttcaggtgat      10800
ccgcccgcct cggcctccca aagtgctggg attacaggca ggagccactg cccctgacca      10860
```

-continued

```
gagaggataa ctttactctt tgatacacga tagtgagcaa aacacagttg tgagaaataa    10920
gcttaacagg ttgcttaaaa agatagtcat ttaatgcatt cttggggcaa gggtccttta    10980
gataattgac ggaagctgtg cgttctgtac ttgtataatg ggacaggatt agagggagtt    11040
gtctatacaa ggcacagcaa gtcctttggg aatgagggga ggcatggagg atcagtgact    11100
tgtgccctct ccagctctca gatctggctc gagaccacca tggctaaggt ggaaggggct    11160
gccgcccagc ttcccagcct caacaaccga ctcagctatg ctgtccgcaa ggtccacacc    11220
attcggggtg cgtaggacaa ctgcgagcca cgtcctgccc ccaccccacc agctcggact    11280
ttcttcttcc tgacccagct ctctctgatc ccacatccat tcaccttcct cctttcacca    11340
gtccttgcat ctcttttttcc cttactccct gtccccactt tctcccatgc aaacttcatc    11400 tcttttctc cctgctttt cccctccagg cctgattgct cgaaagcttg cccttgctca    11460
gctgcgccag gagaggtgaa gtttgtgcac tttgaggtgg atgggctttt agggcattgg    11520
ctgctgggac ccccaaaacc atgaggactg aggtgggatg gggctttgg gatcaggcag    11580 ctgggttatt tctcctgact cttcttcttc cccgtcccag ctgtcccccta ccaccaccgg    11640 tcacagatgt gagccttgag ttgcagcagc tgcgggaaga acggaaccgc ctggatgcag    11700
aactgcagct gagtgcccgc ctcatccagc aggaggtggg ccgggctcgg gagcaaggta    11760
cacctggttg ccagagggtg gagaggatga ggaaaaaccc agtgtctagg gtgctgggag    11820
aggcctgacc cagcacccc tcccttttagg ggaggcagag cggcagcagc tgagcaaggt    11880
ggcccagcag ctggagcagg agctgcagca gacccaggag tccctggcta gcttggggct    11940
gcagctggag gtagcacgcc agggccagca ggagagcaca gaggaggctg ccagtctgcg    12000
gcaggagctg acccagcagc aggaactcta cgggcaaggt gtcgagaggg aaatgggtgc    12060
ttcccttgga gggtggggtg ggaactgcga atcaaagctc ctgctgatat gccccgtctg    12120
cactttcacc ccagccctgc aagaaaaggt ggctgaagtg gaaactcggc tgcgggagca    12180
actctcagac acagagagga ggctgaacga ggctcggagg gagcatgcca aggccggtga    12240
gccttgccag ggtggatagg gccttccagg aagaaggaag tgttaagaca taaggttatt    12300
attttcccct caaagtgtgt tcaaagcttc attacaggaa gtaatgaagg tatccaggag    12360
tagcacagat gaattatcac atcgtgaaca cacccatgta gccagcacca gattaagaaa    12420
cagcatatgg ccggtcgcgg tggcttatgc ctgtaatcca agcactttgg gaggccgagg    12480
tgggtgtatc acctgaggtc aggagtttga ggccagcctg gacaacatgg cgaaaccctg    12540
tctcgactaa aaatacaaaa attagctagg cctggtggtg ggcacctgta ccccaagctt    12600
acttgtgagg ctgatgtggg aagactacat gaacccggga ggtcgaggct gcagtgagcc    12660
aagattgtgc cactgcactc aagcctgggt gatagagaaa gaccatgtgt caaaaaaga    12720 attgtgtaat gaatgtatct tctctaacta aatatagcag ttaacatttg ccacatttgg    12780
tctcttatct atatacacac atatttgtac atcttttgaa tcactttaag ttgtaatcat    12840
ttaatgtttt gttgttgttg ttgtttgaga cagagtcttc ctctgtcacc agctggagtg    12900
cagtggcatg atcttggctc actgtgacct ctgcctcccg ggttcaagcc attctcctgg    12960
ctcagcctcc caagtagctg ggattacagg cgcccaccac catgcccagc tagtttttgt    13020
atttgcagta gagacgggat tacaccgtgt tggccaggat ggtctcgagc tcctgacctc    13080
gtgatccgcc cgctttggca tcccaaagtg ctgggattat aggcgtgagc caccacgcct    13140
aagtaagttg taaacataag ttgttcagcc gcatctccca aagccagtaa attctcctat    13200
atagctgcaa tcatcacact ttaagacagt gaacactaat tgcacaaaat ctaacccagt    13260
```

-continued

```
tcatgttcag atttcccctg aggaactcca ggatggttca gggatgagga agatacttag   13320
gttcagattc ccaggctcct agagcatcag cccacccctc caactgtaca aagagacag    13380 atccacagag cagaacagcc tccccaagcc acagagttgg tgacccagcg tttgttcctg   13440
tcttcatggt gcctggctgc ctctggcctg actcacacct gcctcctctg tgccttggcc   13500
tctctgtagt ggtctccttg cgccagattc agcgcagagc cgcccaggaa aaggagcgga   13560
gccaggaact caggcgtctg caggaggagg cccggaagga ggaggggcag cgactggccc   13620
ggcgcttgca ggagctagag agggataaga acctcatgct ggtaggagac aggagggcag   13680
acaggcagac actagggccc atcctgggct ggttcctggg ctagaggtgt ggaaagagga   13740
tggtgaggga ggctctatcc gggctaggtt taaccctctc cttcccaggc caccttgcag   13800
caggaaggtc tcctctcccg ttacaagcag cagcgactgt tgacagttct tccttccta   13860 ctggataaga agaaatctgt ggtgtccagc cccaggcctc cagagtgttc agcatctgca   13920
cctgtagcag cagcagtgcc caccagggag tccataaaag gtcttgggcc aagcacaaag   13980
ggacaaggga caaatgcgcg cacttcagga atctcctctt cagactctgg catgatgagt   14040
gttgttctct gcggtccttc gaggccctta gcctctttta gcgatgccca gcttggacca   14100
aagagcctcc tctctcccat tcctcatttc ctgtgccagc cctgtttcct ctgtaaccac   14160
gagcaccttc ccttgtctgg tgctcatctg ctgtcttcct tcccagggtc cctctctgtc   14220
ctgctcgatg acctgcagga cctgagtgaa gccatttcca aagaggaagc tgtttgtcaa   14280
ggagacaacc ttgacagatg ctccagctcc aatccccaga tgagcagcta agcagctgac   14340
agttggaggg aaagccagcc tgggggctgg gaggatcctg gagaagtggg tggggacaga   14400
ccagcccttc cccatcctgg ggttgccctg ggggatacca gctgagtctg aattctgctc   14460
taaataaaga cgactacaga agg                                           14483
```

<210> SEQ ID NO 4
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 4 gaaacacccca cgactgcga                                               19

<210> SEQ ID NO 5
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 5
aggaggagac cagccagcag                                               20

<210> SEQ ID NO 6
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 6
tcctcgagct gccatcagtc                                               20

<210> SEQ ID NO 7
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 7
ggcatgagag tcgcttgaac c                                    21

<210> SEQ ID NO 8
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 8
cgagaggccg attactgaga t                                    21

<210> SEQ ID NO 9
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 9
gactagagcc agatccggag                                       20

<210> SEQ ID NO 10
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 10
gggtggttct gcaggatctt                                       20

<210> SEQ ID NO 11
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 11
agagtgcgag acgatggg                                         18

<210> SEQ ID NO 12
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 12
cagtggccaa agcgtcagc                                        19

<210> SEQ ID NO 13
<211> LENGTH: 18
<212> TYPE: DNA
<213> ORGANISM: Artificial Sequence
<220> FEATURE:
<223> OTHER INFORMATION: Artificially synthesized primer sequence

```
<400> SEQUENCE: 13
agccgcctcc acagagct                                                        18

<210> SEQ ID NO 14
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 14
aaatacttct ccagcaaccc c                                                    21

<210> SEQ ID NO 15
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 15
ggaaaacttc agggtcagct ag                                                   22

<210> SEQ ID NO 16
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 16
agatcccctg ccgctcca                                                        18

<210> SEQ ID NO 17
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 17
acttcttcag gcgtcagagg tgc                                                  23

<210> SEQ ID NO 18
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 18
tggaggagtg taacgaaggt ttctg                                                25

<210> SEQ ID NO 19
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 19
tctggcagcc acccagga                                                        18

<210> SEQ ID NO 20
```

```
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 20
gcaggactga tgcaaaca                                                18

<210> SEQ ID NO 21
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 21
ctccctatca tgacccagag                                              20

<210> SEQ ID NO 22
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 22
gaaatggctt tctggacaca ttgg                                         24

<210> SEQ ID NO 23
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 23
ctcggtcctc tgcgggtg                                                18

<210> SEQ ID NO 24
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 24
ctacatgtgg tccgaatg                                                18

<210> SEQ ID NO 25
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 25
acgagagctc atcacctg                                                18

<210> SEQ ID NO 26
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 26
```

-continued caaggccatc agtgaatccc t                     21

<210> SEQ ID NO 27
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 27
tgtgcttccc ctttctacct ta                    22

<210> SEQ ID NO 28
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 28
cctcccactt tcaagctcg                        19

<210> SEQ ID NO 29
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 29
gaggaagggt cactagcaag c                     21

<210> SEQ ID NO 30
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 30
ccctcaacta tccttccagc a                     21

<210> SEQ ID NO 31
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 31
ttggaagcta ctgcccagc                        19

<210> SEQ ID NO 32
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 32
cagaaagtgg gagtgaaggg a                     21

<210> SEQ ID NO 33
<211> LENGTH: 19
<212> TYPE: DNA

```
<213> ORGANISM: Artificial Sequence
<220> FEATURE:
<223> OTHER INFORMATION: Artificially synthesized primer sequence

<400> SEQUENCE: 33
atgggacagc catcagtgg                                              19

<210> SEQ ID NO 34
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 34
ccagcaatta gtgatgtggt gg                                          22

<210> SEQ ID NO 35
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 35
tctacacgct cctccaaggg                                             20

<210> SEQ ID NO 36
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 36
cgggagagaa ggtggtacct aa                                          22

<210> SEQ ID NO 37
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 37
aacatgagct acagcaagag gagtt                                       25

<210> SEQ ID NO 38
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 38
gaggagaaac aaagatgcca cc                                          22

<210> SEQ ID NO 39
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 39
gatgccacct tcatggaagg                                             20
```

<210> SEQ ID NO 40
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 40
acctgccact ttgcttccag                                        20

<210> SEQ ID NO 41
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 41
atgcagcaaa ggacagggtc                                        20

<210> SEQ ID NO 42
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 42
gctgcagcca ggacttagg                                         19

<210> SEQ ID NO 43
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 43
aacaaggtgc ccaggaacc                                         19

<210> SEQ ID NO 44
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 44
atgggacagg attagaggga gtt                                    23

<210> SEQ ID NO 45
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 45
ggatgtggga tcagagagag ct                                     22

<210> SEQ ID NO 46
<211> LENGTH: 21
<212> TYPE: DNA
<213> ORGANISM: Artificial Sequence
<220> FEATURE:

<223> OTHER INFORMATION: Artificially synthesized primer sequence

<400> SEQUENCE: 46
ccttactccc tgtccccact t                                          21

<210> SEQ ID NO 47
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 47
cctcagtcct catggttttg g                                          21

<210> SEQ ID NO 48
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 48
cccaaaacca tgaggactga                                            20

<210> SEQ ID NO 49
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 49
ctctccaccc tctggcaac                                             19

<210> SEQ ID NO 50
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 50
agaggatgag gaaaaaccca gtg                                        23

<210> SEQ ID NO 51
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 51
ggcatatcag caggagcttt g                                          21

<210> SEQ ID NO 52
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 52
gggtgggaac tgcgaatc                                              18

<210> SEQ ID NO 53
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 53
tgaagctttg aacacacttt gag                                          23

<210> SEQ ID NO 54
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 54
tgttcctgtc ttcatggtgc c                                            21

<210> SEQ ID NO 55
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 55
tctttccaca cctctagccc ag                                           22

<210> SEQ ID NO 56
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 56
tgggctagag gtgtggaaag a                                            21

<210> SEQ ID NO 57
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 57
tcatcatgcc agagtctgaa gag                                          23

<210> SEQ ID NO 58
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 58
ccagccctgt ttcctctgt                                               19

<210> SEQ ID NO 59
<211> LENGTH: 19
<212> TYPE: DNA
<213> ORGANISM: Artificial Sequence
<220> FEATURE:
<223> OTHER INFORMATION: Artificially synthesized primer sequence
<210> SEQ ID NO 60
<211> LENGTH: 1725
<212> TYPE: DNA
<213> ORGANISM: Homo sapiens
<220> FEATURE:
<221> NAME/KEY: CDS
<222> LOCATION: (15)...(1601)

<400> SEQUENCE: 60

```
ccgtgcagtc cgag atg ggc tcg tct cgg gca ccc tgg atg ggg cgt gtg        50
              Met Gly Ser Ser Arg Ala Pro Trp Met Gly Arg Val
                1               5                  10 ggt ggg cac ggg atg atg gca ctg ctg ctg gct ggc ctc ctc ctg cca        98
Gly Gly His Gly Met Met Ala Leu Leu Leu Ala Gly Leu Leu Leu Pro
         15                  20                  25 ggg acc ttg gct aag agc att ggc acc ttc tca gac ccc tgt aag gac       146
Gly Thr Leu Ala Lys Ser Ile Gly Thr Phe Ser Asp Pro Cys Lys Asp
 30                  35                  40 ccc acg cgt atc acc tcc cct aac gac ccc tgc ctc act ggg aag ggt       194
Pro Thr Arg Ile Thr Ser Pro Asn Asp Pro Cys Leu Thr Gly Lys Gly
 45                  50                  55                  60 gac tcc agc ggc ttc agt agc tac agt ggc tcc agc agt tct ggc agc       242
Asp Ser Ser Gly Phe Ser Ser Tyr Ser Gly Ser Ser Ser Ser Gly Ser
                 65                  70                  75 tcc att tcc agt gcc aga agc tct ggt ggt ggc tcc agt ggt agc tcc       290
Ser Ile Ser Ser Ala Arg Ser Ser Gly Gly Gly Ser Ser Gly Ser Ser
             80                  85                  90 agc gga tcc agc att gcc cag ggt ggt tct gca gga tct ttt aag cca       338
Ser Gly Ser Ser Ile Ala Gln Gly Gly Ser Ala Gly Ser Phe Lys Pro
         95                  100                 105 gga acg ggg tat tcc cag gtc agc tac tcc tcc gga tct ggc tct agt       386
Gly Thr Gly Tyr Ser Gln Val Ser Tyr Ser Ser Gly Ser Gly Ser Ser
 110                 115                 120 cta caa ggt gca tcc ggt tcc tcc cag ctg ggg agc agc agc tct cac       434
Leu Gln Gly Ala Ser Gly Ser Ser Gln Leu Gly Ser Ser Ser Ser His
125                 130                 135                 140 tcg gga arc agc ggc tct cac tcg gga agc ygc ags tct cat tcg agc       482
Ser Gly Xaa Ser Gly Ser His Ser Gly Ser Xaa Xaa Ser His Ser Ser
                 145                 150                 155 agc agc agc agc ttt cag ttc agc agc agc ttc caa gta ggg aat           530
Ser Ser Ser Ser Phe Gln Phe Ser Ser Ser Phe Gln Val Gly Asn
             160                 165                 170 ggc tct gct ctg cca acc aat gac aac tct tac cgc gga ata cta aac       578
Gly Ser Ala Leu Pro Thr Asn Asp Asn Ser Tyr Arg Gly Ile Leu Asn
         175                 180                 185 cct tcc cag cct gga caa agc tct tcc tct tcc caa acc tyt ggg gta       626
Pro Ser Gln Pro Gly Gln Ser Ser Ser Ser Ser Gln Thr Xaa Gly Val
 190                 195                 200 tcc agc agt ggc caa agc gtc agc tcc aac cag cgt ccc tgt agt tcg       674
Ser Ser Ser Gly Gln Ser Val Ser Ser Asn Gln Arg Pro Cys Ser Ser
205                 210                 215                 220 gac atc ccc gac tct ccc tgc agt gga ggg ccc atc gtc tcg cac tct       722
Asp Ile Pro Asp Ser Pro Cys Ser Gly Gly Pro Ile Val Ser His Ser
                 225                 230                 235 ggc ccc tac atc ccc agc tcc cac tct gtg tca ggg ggt cag agg cct       770
Gly Pro Tyr Ile Pro Ser Ser His Ser Val Ser Gly Gly Gln Arg Pro
             240                 245                 250
```

```
gtg gtg gtg gtg gtg gac cag cac ggt tct ggt gcc cct gga gtg gtt      818
Val Val Val Val Val Asp Gln His Gly Ser Gly Ala Pro Gly Val Val
                255                 260                 265 caa ggt ccc ccc tgt agc aat ggt ggc ctt cca ggc aag wcc tgt ccc      866
Gln Gly Pro Pro Cys Ser Asn Gly Gly Leu Pro Gly Lys Xaa Cys Pro
    270                 275                 280 cca atc acc tct gta gac aaa tcc tat ggt ggc tac gag gtg gtg ggt      914
Pro Ile Thr Ser Val Asp Lys Ser Tyr Gly Gly Tyr Glu Val Val Gly
285                 290                 295                 300 ggc tcc tct gac agt tat ctg gtt cca ggc atg acc tac agt aag ggt      962
Gly Ser Ser Asp Ser Tyr Leu Val Pro Gly Met Thr Tyr Ser Lys Gly
                305                 310                 315 aaa atc tat cct gtg ggc tac ttc acc aaa gag aac cct gtg aaa ggc     1010
Lys Ile Tyr Pro Val Gly Tyr Phe Thr Lys Glu Asn Pro Val Lys Gly
                320                 325                 330 tct cca ggg gtc cct tcc ttt gca gct ggg ccc ccc atc tct gag ggc     1058
Ser Pro Gly Val Pro Ser Phe Ala Ala Gly Pro Pro Ile Ser Glu Gly
                335                 340                 345 aaa tac ttc tcc agc aac ccc atc atc ccc agc cag tcg gca gct tcc     1106
Lys Tyr Phe Ser Ser Asn Pro Ile Ile Pro Ser Gln Ser Ala Ala Ser
350                 355                 360 tcg gcc att gcg ttc cag cca gtg ggg act ggt ggg gtc cag ctc tgt     1154
Ser Ala Ile Ala Phe Gln Pro Val Gly Thr Gly Gly Val Gln Leu Cys
365                 370                 375                 380 gga ggc ggc tcc acg ggc tcc aag gga ccc tgc tct ccc tcc agt tct     1202
Gly Gly Gly Ser Thr Gly Ser Lys Gly Pro Cys Ser Pro Ser Ser Ser
                385                 390                 395 cga gtc ccc agc rgt tct agc att tcc agc agc kcc gkt tya ccc tac     1250
Arg Val Pro Ser Xaa Ser Ser Ile Ser Ser Ser Xaa Xaa Xaa Pro Tyr
                400                 405                 410 cat ccc tgc ggc agt gct tcc cag agc ccc tgc tcc cca cca ggc acc     1298
His Pro Cys Gly Ser Ala Ser Gln Ser Pro Cys Ser Pro Pro Gly Thr
                415                 420                 425 ggc tcc ttc agc agc agc tcc agt tcc caa tcg agt ggc aaa atc atc     1346
Gly Ser Phe Ser Ser Ser Ser Ser Ser Gln Ser Ser Gly Lys Ile Ile
                430                 435                 440 ctt cag cct tgt ggc agc aag tcc arc tct tct ggt cac cct tgc atg     1394
Leu Gln Pro Cys Gly Ser Lys Ser Xaa Ser Ser Gly His Pro Cys Met
445                 450                 455                 460 tct gtc tcc tcc ttg aca ctg act ggg ggc ccc gat ggc tct ccc cat     1442
Ser Val Ser Ser Leu Thr Leu Thr Gly Gly Pro Asp Gly Ser Pro His
                465                 470                 475 cct gat ccc tcc gct ggt gcc aag ccc tgt ggc tcc agc agt gct gga     1490
Pro Asp Pro Ser Ala Gly Ala Lys Pro Cys Gly Ser Ser Ser Ala Gly
                480                 485                 490 aag atc ccc tgc cgc tcc atc cgg gat atc cta gcc caa gtg aag cct     1538
Lys Ile Pro Cys Arg Ser Ile Arg Asp Ile Leu Ala Gln Val Lys Pro
                495                 500                 505 ctg ggg ccc cag cta gct gac cct gaa gtt ttc cta ccc caa gga gag     1586
Leu Gly Pro Gln Leu Ala Asp Pro Glu Val Phe Leu Pro Gln Gly Glu
    510                 515                 520 tta ctc rac agt cca taagtcaact gttgtgtgtg tgcatgcctt gggcacaaac     1641
Leu Leu Xaa Ser Pro
525 aagcacatac actatatccc atatgggaga aggccagtgc ccaggcatag ggttagctca    1701 gtttccctcc ttcccaaaag agtg                                          1725

<210> SEQ ID NO 61
<211> LENGTH: 529
```

```
<212> TYPE: PRT
<213> ORGANISM: Homo sapiens
<220> FEATURE:
<221> NAME/KEY: VARIANT
<222> LOCATION: 143
<223> OTHER INFORMATION: Xaa = Ser or Asn
<220> FEATURE:
<221> NAME/KEY: VARIANT
<222> LOCATION: 151
<223> OTHER INFORMATION: Xaa = Ser or Cys
<220> FEATURE:
<221> NAME/KEY: VARIANT
<222> LOCATION: 152
<223> OTHER INFORMATION: Xaa = Ser or Arg
<220> FEATURE:
<221> NAME/KEY: VARIANT
<222> LOCATION: 202
<223> OTHER INFORMATION: Xaa = Ser or Phe
<220> FEATURE:
<221> NAME/KEY: VARIANT
<222> LOCATION: 282
<223> OTHER INFORMATION: Xaa = Pro or Thr
<220> FEATURE:
<221> NAME/KEY: VARIANT
<222> LOCATION: 401
<223> OTHER INFORMATION: Xaa = Ser or Gly
<220> FEATURE:
<221> NAME/KEY: VARIANT
<222> LOCATION: 408
<223> OTHER INFORMATION: Xaa = Ala or Ser
<220> FEATURE:
<221> NAME/KEY: VARIANT
<222> LOCATION: 409
<223> OTHER INFORMATION: Xaa = Gly or Val
<220> FEATURE:
<221> NAME/KEY: VARIANT
<222> LOCATION: 410
<223> OTHER INFORMATION: Xaa = Ser or Leu
<220> FEATURE:
<221> NAME/KEY: VARIANT
<222> LOCATION: 453
<223> OTHER INFORMATION: Xaa = Ser or Asn
<220> FEATURE:
<221> NAME/KEY: VARIANT
<222> LOCATION: 527
<223> OTHER INFORMATION: Xaa = Asp or Asn

<400> SEQUENCE: 61

Met Gly Ser Ser Arg Ala Pro Trp Met Gly Arg Val Gly Gly His Gly
 1               5                  10                  15

Met Met Ala Leu Leu Leu Ala Gly Leu Leu Pro Gly Thr Leu Ala
            20                  25                  30

Lys Ser Ile Gly Thr Phe Ser Asp Pro Cys Lys Asp Pro Thr Arg Ile
        35                  40                  45

Thr Ser Pro Asn Asp Pro Cys Leu Thr Gly Lys Gly Asp Ser Ser Gly
 50                  55                  60

Phe Ser Ser Tyr Ser Gly Ser Ser Ser Gly Ser Ser Ile Ser Ser
65                  70                  75                  80

Ala Arg Ser Ser Gly Gly Ser Ser Gly Ser Ser Gly Ser Ser
                85                  90                  95

Ile Ala Gln Gly Gly Ser Ala Gly Ser Phe Lys Pro Gly Thr Gly Tyr
            100                 105                 110

Ser Gln Val Ser Tyr Ser Ser Gly Ser Gly Ser Ser Leu Gln Gly Ala
        115                 120                 125

Ser Gly Ser Ser Gln Leu Gly Ser Ser Ser His Ser Gly Xaa Ser
    130                 135                 140

Gly Ser His Ser Gly Ser Xaa Xaa Ser His Ser Ser Ser Ser Ser
145                 150                 155                 160
```

```
Phe Gln Phe Ser Ser Ser Ser Phe Gln Val Gly Asn Gly Ser Ala Leu
                165                 170                 175

Pro Thr Asn Asp Asn Ser Tyr Arg Gly Ile Leu Asn Pro Ser Gln Pro
            180                 185                 190

Gly Gln Ser Ser Ser Ser Gln Thr Xaa Gly Val Ser Ser Ser Gly
        195                 200                 205

Gln Ser Val Ser Ser Asn Gln Arg Pro Cys Ser Ser Asp Ile Pro Asp
    210                 215                 220

Ser Pro Cys Ser Gly Gly Pro Ile Val Ser His Ser Gly Pro Tyr Ile
225                 230                 235                 240

Pro Ser Ser His Ser Val Ser Gly Gly Gln Arg Pro Val Val Val Val
                245                 250                 255

Val Asp Gln His Gly Ser Gly Ala Pro Gly Val Val Gln Gly Pro Pro
                260                 265                 270

Cys Ser Asn Gly Gly Leu Pro Gly Lys Xaa Cys Pro Pro Ile Thr Ser
                275                 280                 285

Val Asp Lys Ser Tyr Gly Gly Tyr Glu Val Val Gly Gly Ser Ser Asp
    290                 295                 300

Ser Tyr Leu Val Pro Gly Met Thr Tyr Ser Lys Gly Lys Ile Tyr Pro
305                 310                 315                 320

Val Gly Tyr Phe Thr Lys Glu Asn Pro Val Lys Gly Ser Pro Gly Val
                325                 330                 335

Pro Ser Phe Ala Ala Gly Pro Pro Ile Ser Glu Gly Lys Tyr Phe Ser
                340                 345                 350

Ser Asn Pro Ile Ile Pro Ser Gln Ser Ala Ala Ser Ser Ala Ile Ala
                355                 360                 365

Phe Gln Pro Val Gly Thr Gly Gly Val Gln Leu Cys Gly Gly Gly Ser
                370                 375                 380

Thr Gly Ser Lys Gly Pro Cys Ser Pro Ser Ser Ser Arg Val Pro Ser
385                 390                 395                 400

Xaa Ser Ser Ile Ser Ser Ser Xaa Xaa Xaa Pro Tyr His Pro Cys Gly
                405                 410                 415

Ser Ala Ser Gln Ser Pro Cys Ser Pro Pro Gly Thr Gly Ser Phe Ser
                420                 425                 430

Ser Ser Ser Ser Ser Gln Ser Ser Gly Lys Ile Ile Leu Gln Pro Cys
                435                 440                 445

Gly Ser Lys Ser Xaa Ser Ser Gly His Pro Cys Met Ser Val Ser Ser
450                 455                 460

Leu Thr Leu Thr Gly Gly Pro Asp Gly Ser Pro His Pro Asp Pro Ser
465                 470                 475                 480

Ala Gly Ala Lys Pro Cys Gly Ser Ser Ala Gly Lys Ile Pro Cys
                485                 490                 495

Arg Ser Ile Arg Asp Ile Leu Ala Gln Val Lys Pro Leu Gly Pro Gln
                500                 505                 510

Leu Ala Asp Pro Glu Val Phe Leu Pro Gln Gly Glu Leu Leu Xaa Ser
                515                 520                 525

Pro

<210> SEQ ID NO 62
<211> LENGTH: 2474
<212> TYPE: DNA
<213> ORGANISM: Homo sapiens
<220> FEATURE:
<221> NAME/KEY: CDS
<222> LOCATION: (23)...(2290)
```

<400> SEQUENCE: 62

```
cgcccttca actctgccaa ga atg gct ccc acc tgg ctc tca gac att ccc         52
                        Met Ala Pro Thr Trp Leu Ser Asp Ile Pro
                        1               5                   10 ctg gtc caa ccc cca ggc cat caa gat gtc tca gag agg cgg cta gac        100
Leu Val Gln Pro Pro Gly His Gln Asp Val Ser Glu Arg Arg Leu Asp
                15                  20                  25 acc cag aga cct caa gtg acc atg tgg gaa cgg gat gtt tcc agt gac        148
Thr Gln Arg Pro Gln Val Thr Met Trp Glu Arg Asp Val Ser Ser Asp
            30                  35                  40 agg cag gag cca ggg cgg aga ggc agg tcc tgg ggg ctg gag ggg tca        196
Arg Gln Glu Pro Gly Arg Arg Gly Arg Ser Trp Gly Leu Glu Gly Ser
        45                  50                  55 cag gcc ctg agc cag cag gct gag gtg atc gtt cgg cag ctg caa gag        244
Gln Ala Leu Ser Gln Gln Ala Glu Val Ile Val Arg Gln Leu Gln Glu
    60                  65                  70 ctg crg tgg ctg gag gag gag gtc tgg ctc ctg cgg gag acc tcg ctg        292
Leu Xaa Trp Leu Glu Glu Glu Val Trp Leu Leu Arg Glu Thr Ser Leu
75                  80                  85                  90 cag cag aag atg agg cta gag gcc cag gcc atg gag cta gag gct ctg        340
Gln Gln Lys Met Arg Leu Glu Ala Gln Ala Met Glu Leu Glu Ala Leu
                95                  100                 105 gca cgg gcg gag aag gcc ggc cga gct gag gct gag ggc ctg cgt gct        388
Ala Arg Ala Glu Lys Ala Gly Arg Ala Glu Ala Glu Gly Leu Arg Ala
            110                 115                 120 gct ttg gct ggg gct gag gtt gtc cgg aag aac ttg gaa gag ggg ags        436
Ala Leu Ala Gly Ala Glu Val Val Arg Lys Asn Leu Glu Glu Gly Xaa
        125                 130                 135 cag cgg gag ctg gaa gag gtt cag agg ctg cac caa gag cag ctg tcc        484
Gln Arg Glu Leu Glu Glu Val Gln Arg Leu His Gln Glu Gln Leu Ser
    140                 145                 150 tct ttg aca cag gct cac gag gag gct ctt tcc agt ttg acc agc aag        532
Ser Leu Thr Gln Ala His Glu Glu Ala Leu Ser Ser Leu Thr Ser Lys
155                 160                 165                 170 gct gag ggc ttg gag aag tct ctg agt agt ctg gaa acc aga aga gca        580
Ala Glu Gly Leu Glu Lys Ser Leu Ser Ser Leu Glu Thr Arg Arg Ala
                175                 180                 185 ggg gaa gcc aag gag ctg gcc gag gct cag agg gag gcc gag ctg ctt        628
Gly Glu Ala Lys Glu Leu Ala Glu Ala Gln Arg Glu Ala Glu Leu Leu
            190                 195                 200 cgg aag cag ctg agc aag acc cag gaa gac ttg gag gct cag gtg acc        676
Arg Lys Gln Leu Ser Lys Thr Gln Glu Asp Leu Glu Ala Gln Val Thr
        205                 210                 215 ctg gtt gag aat cta aga aaa tat gtt ggg gaa caa gtc cct tct gag        724
Leu Val Glu Asn Leu Arg Lys Tyr Val Gly Glu Gln Val Pro Ser Glu
    220                 225                 230 gtc cac agc cag aca tgg gaa ctg gag cga cag aag ctt ctg gam acc        772
Val His Ser Gln Thr Trp Glu Leu Glu Arg Gln Lys Leu Leu Xaa Thr
235                 240                 245                 250 atg cag cac ttg cag gag gac cgg gac agc ctg cat gcc acc gcg gag        820
Met Gln His Leu Gln Glu Asp Arg Asp Ser Leu His Ala Thr Ala Glu
                255                 260                 265 ctg ctg cag gtg cgg gtg cag agc ctc aca cac atc ctc gcc ctg cag        868
Leu Leu Gln Val Arg Val Gln Ser Leu Thr His Ile Leu Ala Leu Gln
            270                 275                 280 gag gag gag ctg acc agg aag gtt caa cct tca gat tcc ctg gag cct        916
Glu Glu Glu Leu Thr Arg Lys Val Gln Pro Ser Asp Ser Leu Glu Pro
        285                 290                 295
```

```
                                                          -continued gag ttt acc agg aag tgc cag tcc ctg ctg aac cgc tgg cgg gag aag     964
Glu Phe Thr Arg Lys Cys Gln Ser Leu Leu Asn Arg Trp Arg Glu Lys
300                 305                 310 gtg ttt gcc ctc atg gtg cag cta aag gcc cag gag ctg gaa cac agt    1012
Val Phe Ala Leu Met Val Gln Leu Lys Ala Gln Glu Leu Glu His Ser
315                 320                 325                 330 gac tct gtt aag cag ctg aag gga cag gtg gcc tca ctc cag gaa aaa    1060
Asp Ser Val Lys Gln Leu Lys Gly Gln Val Ala Ser Leu Gln Glu Lys
                335                 340                 345 gtg aca tcc cag agc cag gag cag gcc atc ctg cag cga tcc ctg cag    1108
Val Thr Ser Gln Ser Gln Glu Gln Ala Ile Leu Gln Arg Ser Leu Gln
            350                 355                 360 gac aaa gcc gca gag gtg gag gtg gag cgt atg ggt gcc aag ggc ctg    1156
Asp Lys Ala Ala Glu Val Glu Val Glu Arg Met Gly Ala Lys Gly Leu
        365                 370                 375 cag ttg gag ctg agc cgt gct cag gag gcc agg cgt ygg tgg cag cag    1204
Gln Leu Glu Leu Ser Arg Ala Gln Glu Ala Arg Arg Xaa Trp Gln Gln
380                 385                 390 cag aca gcc tca gcc gag gag cag ttg agg ctt gtg gtc aat gct gtc    1252
Gln Thr Ala Ser Ala Glu Glu Gln Leu Arg Leu Val Val Asn Ala Val
395                 400                 405                 410 agc agc tct cag atc tgg ctc gag acc acc atg gct aag gtg gaa ggg    1300
Ser Ser Ser Gln Ile Trp Leu Glu Thr Thr Met Ala Lys Val Glu Gly
                415                 420                 425 gct gcc gcc cag ctt ccc agc ctc aac aac cga ctc agc tat gct gtc    1348
Ala Ala Ala Gln Leu Pro Ser Leu Asn Asn Arg Leu Ser Tyr Ala Val
            430                 435                 440 cgc aag gtc cac acc att cgg ggc ctg att gct cga aag ctt gcc ctt    1396
Arg Lys Val His Thr Ile Arg Gly Leu Ile Ala Arg Lys Leu Ala Leu
        445                 450                 455 gct cag ctg cgc cag gag agc tgt ccc cta cca cca ccg gtc aca gat    1444
Ala Gln Leu Arg Gln Glu Ser Cys Pro Leu Pro Pro Pro Val Thr Asp
460                 465                 470 gtg agc ctt gag ttg cag cag ctg cgg gaa gaa cgg aac cgc ctg gat    1492
Val Ser Leu Glu Leu Gln Gln Leu Arg Glu Glu Arg Asn Arg Leu Asp
475                 480                 485                 490 gca gaa ctg cag ctg agt gcc cgc ctc atc cag cag gag gtg ggc cgg    1540
Ala Glu Leu Gln Leu Ser Ala Arg Leu Ile Gln Gln Glu Val Gly Arg
                495                 500                 505 gct cgg gag caa ggg gag gca gag cgg cag cag ctg agc aag gtg gcc    1588
Ala Arg Glu Gln Gly Glu Ala Glu Arg Gln Gln Leu Ser Lys Val Ala
            510                 515                 520 cag cag ctg gag cag gag ctg cag cag acc cag gag tcc ctg gct agc    1636
Gln Gln Leu Glu Gln Glu Leu Gln Gln Thr Gln Glu Ser Leu Ala Ser
        525                 530                 535 ttg ggg ctg cag ctg gag gta gca cgc cag tgc cag cag gag agc aca    1684
Leu Gly Leu Gln Leu Glu Val Ala Arg Gln Cys Gln Gln Glu Ser Thr
540                 545                 550 gag gag gct gcc agt ctg cgg cag gag ctg acc cag cag cag gaa ctc    1732
Glu Glu Ala Ala Ser Leu Arg Gln Glu Leu Thr Gln Gln Gln Glu Leu
555                 560                 565                 570 tac ggg caa gcc ctg caa gaa aag gtg gct gaa gtg gaa act cgg ctg    1780
Tyr Gly Gln Ala Leu Gln Glu Lys Val Ala Glu Val Glu Thr Arg Leu
                575                 580                 585 cgg gag caa ctc tca gac aca gag agg agg ctg aac gag gct crg agg    1828
Arg Glu Gln Leu Ser Asp Thr Glu Arg Arg Leu Asn Glu Ala Xaa Arg
            590                 595                 600 gag cat gcc aag gcc gtg gtc tcc ttr cgc cak att cag cgc aga gcc    1876
Glu His Ala Lys Ala Val Val Ser Xaa Arg Xaa Ile Gln Arg Arg Ala
        605                 610                 615
```

```
gcc cag gaa awg gag cgg agc cag gaa ctc agg ygt ctg cag gag gag      1924
Ala Gln Glu Xaa Glu Arg Ser Gln Glu Leu Arg Xaa Leu Gln Glu Glu
            620                 625                 630 gcc cgg aag gag gag ggg cag cga ctg gcc cgg cgc ttg cag gag cta      1972
Ala Arg Lys Glu Glu Gly Gln Arg Leu Ala Arg Arg Leu Gln Glu Leu
635                 640                 645                 650 gag agg gat aag aac ctc atg ctg gcc acc ttg cag cag gaa ggt ctc      2020
Glu Arg Asp Lys Asn Leu Met Leu Ala Thr Leu Gln Gln Glu Gly Leu
                655                 660                 665 ctc tcc cgt tac aag cag cag cga ctg ttg aca gtt ctt cct tcc cta      2068
Leu Ser Arg Tyr Lys Gln Gln Arg Leu Leu Thr Val Leu Pro Ser Leu
            670                 675                 680 ctg gat aag aag aaa tct gtg gtg tcc agc ccc agg cct cca gag tgt      2116
Leu Asp Lys Lys Lys Ser Val Val Ser Ser Pro Arg Pro Pro Glu Cys
        685                 690                 695 tca gca tct gca cct gta gca gca gca gtg ccc acc agg gag tcc ata      2164
Ser Ala Ser Ala Pro Val Ala Ala Ala Val Pro Thr Arg Glu Ser Ile
700                 705                 710 aaa ggg tcc ctc tct gtc ctg ctc gat gac ctg cag gac ctg agt gaa      2212
Lys Gly Ser Leu Ser Val Leu Leu Asp Asp Leu Gln Asp Leu Ser Glu
715                 720                 725                 730 gcc att tcc aaa gag gaa gct gtt tgt caa gga gac aac ctt gac aga      2260
Ala Ile Ser Lys Glu Glu Ala Val Cys Gln Gly Asp Asn Leu Asp Arg
                735                 740                 745 tgc tcc agc tsc aat ccc cag atg agc agc taagcagctg acagttggag        2310
Cys Ser Ser Xaa Asn Pro Gln Met Ser Ser
            750                 755 ggaaagccag cctgggggct gggaggatcc tggagaagtg ggtggggaca gaccagccct    2370
tccccatcct ggggttgccc tgggggatac cagctgagtc tgaattctgc tctaaataaa    2430
gacgactaca gaaggaaaaa aaaaaaaaaa aaaaaaaaaa aaaa                     2474

<210> SEQ ID NO 63
<211> LENGTH: 756
<212> TYPE: PRT
<213> ORGANISM: Homo sapiens
<220> FEATURE:
<221> NAME/KEY: VARIANT
<222> LOCATION: 76
<223> OTHER INFORMATION: Xaa = Arg or Gln
<220> FEATURE:
<221> NAME/KEY: VARIANT
<222> LOCATION: 138
<223> OTHER INFORMATION: Xaa = Arg or Ser
<220> FEATURE:
<221> NAME/KEY: VARIANT
<222> LOCATION: 249
<223> OTHER INFORMATION: Xaa = Glu or Asp
<220> FEATURE:
<221> NAME/KEY: VARIANT
<222> LOCATION: 391
<223> OTHER INFORMATION: Xaa = Trp or Arg
<220> FEATURE:
<221> NAME/KEY: VARIANT
<222> LOCATION: 601
<223> OTHER INFORMATION: Xaa = Arg or Gln
<220> FEATURE:
<221> NAME/KEY: VARIANT
<222> LOCATION: 611
<223> OTHER INFORMATION: Xaa = Leu or Ile
<220> FEATURE:
<221> NAME/KEY: VARIANT
<222> LOCATION: 613
<223> OTHER INFORMATION: Xaa = Gln or Tyr
<220> FEATURE:
<221> NAME/KEY: VARIANT
<222> LOCATION: 622
```

<223> OTHER INFORMATION: Xaa = Lys or Met
<220> FEATURE:
<221> NAME/KEY: VARIANT
<222> LOCATION: 630
<223> OTHER INFORMATION: Xaa = Arg or Cys
<220> FEATURE:
<221> NAME/KEY: VARIANT
<222> LOCATION: 750
<223> OTHER INFORMATION: Xaa = Cys or Ser

<400> SEQUENCE: 63

```
Met Ala Pro Thr Trp Leu Ser Asp Ile Pro Leu Val Gln Pro Pro Gly
  1               5                  10                  15

His Gln Asp Val Ser Glu Arg Arg Leu Asp Thr Gln Arg Pro Gln Val
             20                  25                  30

Thr Met Trp Glu Arg Asp Val Ser Ser Asp Arg Gln Glu Pro Gly Arg
         35                  40                  45

Arg Gly Arg Ser Trp Gly Leu Glu Gly Ser Gln Ala Leu Ser Gln Gln
     50                  55                  60

Ala Glu Val Ile Val Arg Gln Leu Gln Glu Leu Xaa Trp Leu Glu Glu
 65                  70                  75                  80

Glu Val Trp Leu Leu Arg Glu Thr Ser Leu Gln Gln Lys Met Arg Leu
                 85                  90                  95

Glu Ala Gln Ala Met Glu Leu Glu Ala Leu Ala Arg Ala Glu Lys Ala
            100                 105                 110

Gly Arg Ala Glu Ala Glu Gly Leu Arg Ala Ala Leu Ala Gly Ala Glu
        115                 120                 125

Val Val Arg Lys Asn Leu Glu Glu Gly Xaa Gln Arg Glu Leu Glu Glu
130                 135                 140

Val Gln Arg Leu His Gln Glu Gln Leu Ser Ser Leu Thr Gln Ala His
145                 150                 155                 160

Glu Glu Ala Leu Ser Ser Leu Thr Ser Lys Ala Glu Gly Leu Glu Lys
                165                 170                 175

Ser Leu Ser Ser Leu Glu Thr Arg Arg Ala Gly Glu Ala Lys Glu Leu
            180                 185                 190

Ala Glu Ala Gln Arg Glu Ala Glu Leu Leu Arg Lys Gln Leu Ser Lys
        195                 200                 205

Thr Gln Glu Asp Leu Glu Ala Gln Val Thr Leu Val Glu Asn Leu Arg
210                 215                 220

Lys Tyr Val Gly Glu Gln Val Pro Ser Glu Val His Ser Gln Thr Trp
225                 230                 235                 240

Glu Leu Glu Arg Gln Lys Leu Leu Xaa Thr Met Gln His Leu Gln Glu
                245                 250                 255

Asp Arg Asp Ser Leu His Ala Thr Ala Glu Leu Leu Gln Val Arg Val
            260                 265                 270

Gln Ser Leu Thr His Ile Leu Ala Leu Gln Glu Glu Leu Thr Arg
        275                 280                 285

Lys Val Gln Pro Ser Asp Ser Leu Glu Pro Glu Phe Thr Arg Lys Cys
    290                 295                 300

Gln Ser Leu Leu Asn Arg Trp Arg Glu Lys Val Phe Ala Leu Met Val
305                 310                 315                 320

Gln Leu Lys Ala Gln Glu Leu Glu His Ser Asp Ser Val Lys Gln Leu
                325                 330                 335

Lys Gly Gln Val Ala Ser Leu Gln Glu Lys Val Thr Ser Gln Ser Gln
            340                 345                 350

Glu Gln Ala Ile Leu Gln Arg Ser Leu Gln Asp Lys Ala Ala Glu Val
```

```
                355                 360                 365
Glu Val Glu Arg Met Gly Ala Lys Gly Leu Gln Leu Glu Leu Ser Arg
    370                 375                 380
Ala Gln Glu Ala Arg Arg Xaa Trp Gln Gln Thr Ala Ser Ala Glu
385                 390                 395                 400
Glu Gln Leu Arg Leu Val Val Asn Ala Val Ser Ser Gln Ile Trp
                405                 410                 415
Leu Glu Thr Thr Met Ala Lys Val Glu Ala Ala Ala Gln Leu Pro
                420                 425                 430
Ser Leu Asn Asn Arg Leu Ser Tyr Ala Val Arg Lys Val His Thr Ile
                435                 440                 445
Arg Gly Leu Ile Ala Arg Lys Leu Ala Leu Ala Gln Leu Arg Gln Glu
    450                 455                 460
Ser Cys Pro Leu Pro Pro Val Thr Asp Val Ser Leu Glu Leu Gln
465                 470                 475                 480
Gln Leu Arg Glu Glu Arg Asn Arg Leu Asp Ala Glu Leu Gln Leu Ser
                485                 490                 495
Ala Arg Leu Ile Gln Gln Glu Val Gly Arg Ala Arg Glu Gln Gly Glu
                500                 505                 510
Ala Glu Arg Gln Gln Leu Ser Lys Val Ala Gln Gln Leu Glu Gln Glu
                515                 520                 525
Leu Gln Gln Thr Gln Glu Ser Leu Ala Ser Leu Gly Leu Gln Leu Glu
    530                 535                 540
Val Ala Arg Gln Cys Gln Gln Glu Ser Thr Glu Glu Ala Ala Ser Leu
545                 550                 555                 560
Arg Gln Glu Leu Thr Gln Gln Glu Leu Tyr Gly Gln Ala Leu Gln
                565                 570                 575
Glu Lys Val Ala Glu Val Glu Thr Arg Leu Arg Glu Gln Leu Ser Asp
                580                 585                 590
Thr Glu Arg Arg Leu Asn Glu Ala Xaa Arg Glu His Ala Lys Ala Val
                595                 600                 605
Val Ser Xaa Arg Xaa Ile Gln Arg Arg Ala Ala Gln Glu Xaa Glu Arg
    610                 615                 620
Ser Gln Glu Leu Arg Xaa Leu Gln Glu Glu Ala Arg Lys Glu Glu Gly
625                 630                 635                 640
Gln Arg Leu Ala Arg Arg Leu Gln Glu Leu Glu Arg Asp Lys Asn Leu
                645                 650                 655
Met Leu Ala Thr Leu Gln Gln Glu Gly Leu Leu Ser Arg Tyr Lys Gln
                660                 665                 670
Gln Arg Leu Leu Thr Val Leu Pro Ser Leu Leu Asp Lys Lys Ser
    675                 680                 685
Val Val Ser Ser Pro Arg Pro Pro Glu Cys Ser Ala Ser Ala Pro Val
690                 695                 700
Ala Ala Ala Val Pro Thr Arg Glu Ser Ile Lys Gly Ser Leu Ser Val
705                 710                 715                 720
Leu Leu Asp Asp Leu Gln Asp Leu Ser Glu Ala Ile Ser Lys Glu Glu
                725                 730                 735
Ala Val Cys Gln Gly Asp Asn Leu Asp Arg Cys Ser Ser Xaa Asn Pro
                740                 745                 750
Gln Met Ser Ser
            755
```

US 6,933,118 B2

METHOD OF TESTING FOR PSORIASIS VULGARIS

This application is a continuation-in-part of PCT/JP00/08624, filed Dec. 6, 2000, which claims the benefit of priority to Japanese Patent Application No. 11/346867, filed Dec. 6, 1999.

TECHNICAL FIELD

The present invention relates to a method of testing for psoriasis vulgaris and DNA molecules used therefore.

BACKGROUND

Psoriasis vulgaris (MIM 177900) is a skin disease characterized by inflammatory cell infiltration and hyperproliferation of epidermal cells.

A genetic factor is thought to be deeply involved in the onset of this disease. Investigation into the existing region of the causative gene responsible for the disease is in progress. For example, the sequence of a DNA of 2,229,817 bp, predicted to contain a sensitive gene of psoriasis, has been determined (The MHC sequencing consortium, Nature 400:921–923, 1999). The present inventors narrowed the scope of the existing region of the causative gene of psoriasis vulgaris by microsatellite analyses (Oka et al., Hum. Mol. Genet. 8:2165–2170, 1999) and found three known genes from the genomic sequence of HLA class I [i.e., POU5F1 (OTF3: octamer transcription factor 3), TCF19 (SC1: cell growth regulated gene), and MHC S]; as well as four novel genes within the region [i.e., HCR (helix coiled-coil rod homologue), SPR1 (skin specific proline rich gene 1), SEEK1 (specific expressed gene in epidermal keratinocytes 1), and STG (skin specific telomeric gene) (AB029331, AB031480, AB031479, and AB031481, respectively)] (Oka et al., Hum. Mol. Genet. 8:2165–2170, 1999) (FIG. 1).

Psoriasis vulgaris is known to show a strong positive association with HLA-Cw6/7 among these genes (Tiilikainen et al., Br. J. Dermatol., 102, 179–184, 1980; Bhalerao et al., Hum. Mol. Genet. 7:1537–1545, 1998). However, it remains to be seen whether the HLA genes themselves are responsible for the onset of psoriasis or whether some other non-HLA genes linked to the HLA genes are responsible.

Recently, a significant association between psoriasis and dimorphisms (Ser410Leu substitution) at cDNA position +1243 of the MHC S gene (the product of which are also called "corneodesmosin") were reported in Caucasian populations (Tazi-Ahnini et al., Hum. Mol. Genet. 8:1135–1140, 1999; Allen et al., The Lancet 353:1589–1590, 1999). However, according to these papers, Tazi-Ahnini et al. reported a significant increase of the allele of Leu at position +1243, while Allen et al. reported an increase of another allele (Ser). Thus, the accuracy of these reports has been questioned.

The present inventors previously observed that psoriasis in a Japanese population was significantly associated with HLA-Cw6/7, as in the case of Caucasian (Ozawa et al., J. Am. Acad. Dermatol. 4:205–230, 1981; Asahina et al., J. Invest. Dermatol. 97:254–258, 1991); however, they also reported that no genetic polymorphism of the MHC S gene, significantly associated with psoriasis vulgaris, could be found (Ishihara et al., Tissue Antigens 48:182–186, 1996).

Thus, genes responsible for psoriasis vulgaris have not yet been identified. Additionally, only few reports on genetic polymorphisms that may be used as the target of testing for psoriasis vulgaris have been published.

SUMMARY

The present invention provides novel genetic polymorphisms that relate to psoriasis vulgaris. Moreover, the present invention provides a method of testing for psoriasis vulgaris by detecting these polymorphisms, and DNA molecules used for the test.

By analyzing the sequences of the MHC S gene, SEEK1 gene, and HCR gene of Japanese psoriasis patients and those of healthy individuals in detail, the present inventors discovered polymorphisms existing within the entire genes thereof and analyzed the relationship between the polymorphisms and psoriasis. As a result, the present inventors demonstrated that some of the analyzed polymorphisms significantly correlated to psoriasis in Japanese patients. Moreover, the present inventors discovered that psoriasis vulgaris could be tested by assaying for these genetic polymorphisms in psoriasis patients based on these correlations.

Thus, the present invention relates to a method of testing for psoriasis vulgaris by detecting the genetic polymorphisms in subjects, and DNA molecules used for the test. More specifically, the present invention provides:

(1) a primer DNA for detecting psoriasis vulgaris in a patient selected from the group of:

(a) a primer DNA that hybridizes to a DNA comprising the nucleotide sequence of SEQ ID NO:1 or the complementary strand thereof and which is designed so that the 4040th nucleotide of SEQ ID NO:1 or the corresponding nucleotide on the complementary strand thereof is positioned between the primers;

(b) a primer DNA that hybridizes to a DNA comprising the nucleotide sequence of SEQ ID NO:2 or the complementary strand thereof and which is designed so that the 6413th nucleotide of SEQ ID NO:2 or the corresponding nucleotide on the complementary strand thereof is positioned between the primers;

(c) a primer DNA that hybridizes to a DNA comprising the nucleotide sequence of SEQ ID NO:2 or the complementary strand thereof, and which is designed so that the 14378th nucleotide of SEQ ID NO:2 or the corresponding nucleotide on the complementary strand thereof is positioned between the primers; and (d) a primer DNA that hybridizes to a DNA comprising the nucleotide sequence of SEQ ID NO:3 or the complementary strand thereof and which is designed so that the 6196th nucleotide of SEQ ID NO:3 or the corresponding nucleotide on the complementary strand thereof is positioned between the primers;

(2) a reagent for testing for psoriasis vulgaris including the primer DNA of (1);

(3) a method of testing for psoriasis vulgaris, which detects a nucleotide polymorphism selected from the group of:

(a) a polymorphism involving the 4040th nucleotide of SEQ ID NO:1 or a corresponding nucleotide on a complementary strand thereof, (b) a polymorphism involving the 6413th nucleotide of SEQ ID NO:2 or a corresponding nucleotide on a complementary strand thereof, (c) a polymorphism involving the 14378th nucleotide of SEQ ID NO:2 or a corresponding nucleotide on a complementary strand thereof; and (d) a polymorphism involving the 6196th nucleotide of SEQ ID NO:3 or a corresponding nucleotide on a complementary strand thereof, (4) the method of testing for psoriasis vulgaris according to (3), comprising the steps of:

(a) preparing a DNA sample from a subject;

(b) amplifying the DNA derived from the subject using the primer DNA of (1); and (c) determining the nucleotide sequence of the amplified DNA;

(5) the method of testing for psoriasis vulgaris according to (3), comprising the steps of:

(a) preparing a DNA sample from a subject;

(b) amplifying the DNA derived from the subject using the DNA of (1) as a primer;

(c) dissociating the amplified DNA into single strand DNA;

(d) separating the dissociated single strand DNA on a nondenaturing gel; and (e) determining the polymorphism of the subject based on the mobility of the separated single strand DNA on the gel;

(6) a DNA for testing for psoriasis vulgaris selected from the group of:

(a) a part or a whole of a DNA consisting of the nucleotide sequence of SEQ ID NO:1 or the sequence of SEQ ID NO:1 wherein the 4040th nucleotide has been substituted with another nucleotide, wherein said DNA comprises the 4040th nucleotide of the nucleotide sequence of SEQ ID NO:1;

(b) a part or a whole of a DNA consisting of the nucleotide sequence of SEQ ID NO:2 or the sequence of SEQ ID NO:2 wherein the 6413th nucleotide has been substituted with another nucleotide, wherein said DNA comprises the 6413th nucleotide of the nucleotide sequence of SEQ ID NO:2;

(c) a part or a whole of a DNA consisting of the nucleotide sequence of SEQ ID NO:2 or the sequence of SEQ ID NO:2 wherein the 14378th nucleotide has been substituted with another nucleotide, wherein said DNA comprises the 14378th nucleotide of the nucleotide sequence of SEQ ID NO:2; and (d) a part or a whole of a DNA consisting of the nucleotide sequence of SEQ ID NO:3 or the sequence of SEQ ID NO:3 wherein the 6196th nucleotide has been substituted with another nucleotide, wherein said DNA comprises the 6196th nucleotide of the nucleotide sequence of SEQ ID NO:3; and (7) an oligonucleotide that hybridizes to a region of the DNA according to (6), said region comprising a polymorphic site selected from the group of:

(a) the 4040th nucleotide of the DNA consisting of the nucleotide sequence of SEQ ID NO:1 or the sequence of SEQ ID NO:1 wherein the 4040th nucleotide has been substituted with another nucleotide;

(b) the 6413th nucleotide of the DNA consisting of the nucleotide sequence of SEQ ID NO:2 or the sequence of SEQ ID NO:2 wherein the 6413th nucleotide has been substituted with another nucleotide;

(c) the 14378th nucleotide of the DNA consisting of the nucleotide sequence of SEQ ID NO:2 or the sequence of SEQ ID NO:2 wherein the 14378th nucleotide has been substituted with another nucleotide; and (d) the 6196th nucleotide of the DNA consisting of the nucleotide sequence of SEQ ID NO:3 or the sequence of SEQ ID NO:3 wherein the 6196th nucleotide has been substituted with another nucleotide.

The present invention provides a method of testing for psoriasis vulgaris wherein the genetic polymorphisms are detected, and DNA molecules used for the test. The term "testing for psoriasis vulgaris" herein encompasses not only the testing of a subject expressing the symptom of psoriasis vulgaris, but also to testing whether an asymptomatic subject is susceptible to psoriasis vulgaris.

Polymorphisms of the MHC S gene, SEEK1 gene, and HCR gene are detected in the test for psoriasis vulgaris of this invention. The polymorphism used as the target in the detection is not limited, so long as it is detected with significantly high frequency in psoriasis patients as compared to healthy individuals. For example, the 4040th nucleotide of the genomic DNA sequence of SEQ ID NO:1 (i.e., the 1236th nucleotide of the cDNA in FIG. 2) is a preferable polymorphic site for the MHC S gene, the 6413th and 14378th nucleotide of the genomic DNA sequence of SEQ ID NO:2 are the preferred polymorphic sites for the SEEK1 gene, and the 6196th nucleotide of the genomic DNA sequence of SEQ ID NO:3 (i.e., the 769th nucleotide of the cDNA in FIG. 3) is the preferred polymorphic site for the HCR gene. The nucleotide and amino acid sequences of the MHC S cDNA are shown in FIG. 2, and those of the HCR cDNA are shown in FIG. 3.

According to an embodiment of the test method of the present invention, the nucleotide sequence of the gene region containing these target sites of a subject are directly determined. More specifically, the method comprises the steps of: (a) preparing a DNA sample from a subject, (b) amplifying the DNA derived from the subject using the primer DNA, and (c) determining the nucleotide sequence of the amplified DNA.

According to the method, first, a DNA sample is prepared from a subject. A genomic DNA sample can be prepared, for example, from peripheral blood leukocyte collected from a subject using a QIAmpDNA blood kit (QIAGEN). Next, primers are designed so that the target polymorphic sites are amplified, and polymerase chain reaction (PCR) is performed with these primers using the prepared DNA sample as a template. Then, the nucleotide sequence of the obtained PCR product is determined. One of the primer pair used for the above-mentioned PCR is preferably utilized as a sequencing primer in the nucleotide sequencing. As a result of nucleotide sequencing, when the type of the polymorphism detected for a subject corresponds with the type associated with psoriasis vulgaris, the subject is determined to be at a risk of psoriasis vulgaris.

The primer DNAs that can be used in the test method for MHC S gene are not limited, so long as they hybridize to the DNA consisting of the nucleotide sequence of SEQ ID NO:1 or the complementary strand thereof, and wherein said primer pairs are designed so that the target nucleotide site of the DNA is positioned between these primers. The primer DNAs used in the test for SEEK1 gene are not limited, so long as they hybridize to the DNA consisting of the nucleotide sequence of SEQ ID NO:2 or the complementary strand thereof and are designed so that the target nucleotide site of the DNA is positioned between primer pairs. The primer DNAs used in the test for HCR gene are not limited, so long as they hybridizes to the DNA consisting of the nucleotide sequence of SEQ ID NO:3 or the complementary strand thereof, and are designed so that the target nucleotide site of the DNA is positioned between primer pairs. The primer DNAs used in the test of the present invention are generally 15-mer to 100-mer, preferably 15-mer to 40-mer, and more preferably 20-mer to 30-mer. The hybridization of these primer DNAs to the template DNA can be performed under appropriate condition, such as those described in Examples.

The test method of the present invention may be conducted following various methods, apart from directly determining the nucleotide sequence of the DNA derived from the subject. For example, according to an embodiment of the invention, the method comprises the steps of: (a) preparing a DNA sample from a subject, (b) amplifying the DNA derived from the subject using above-mentioned primer pair DNAs of this invention, (c) dissociating the amplified DNA into single stranded DNAs, (d) separating the dissociated single stranded DNAs on a non-denaturing gel, and (e) comparing the mobility of the separated single stranded DNAs on the gel with those of healthy controls.

The above method may, for example, utilize the PCR-SSCP (single-strand conformation polymorphism) method ("Cloning and polymerase chain reaction-single-strand conformation polymorphism analysis of anonymous Alu repeats on chromosome 11." Genomics 12(1):139–146, 1992; "Detection of p53 gene mutations in human brain tumors by single-strand conformation polymorphism analysis of polymerase chain reaction products." Oncogene 6(8):1313–1318, 1991; "Multiple fluorescence-based PCR-SSCP analysis with postlabeling." PCR Methods Appl. 4(5):275–282, 1995). This method is particularly preferable for screening many DNA samples, since it has advantages such as: comparative simplicity of operation; small amount of required test sample; and so on. The principle of the method is as follows. A single stranded DNA dissociated from a double-stranded DNA fragment forms a unique higher conformation, depending on respective nucleotide sequence. After electrophoresis on a polyacrylamide gel without a denaturant, complementary single-stranded DNAs having the same chain length of the dissociated DNA strand shift to different positions in accordance with the difference of the respective higher conformations. The conformation of a single-stranded DNA changes even by a substitution of one base, which change results in a different mobility on polyacrylamide gel electrophoresis. Accordingly, the presence of a mutation in a DNA fragment due to even a single point mutation, deletion, insertion, and such can be detected by detecting the changes in the mobility.

More specifically, a region containing a target site of the MHC S gene, SEEK1 gene, or MCR gene is first amplified by PCR or the like. Preferably, a length of about 100 to 600 bp is amplified. PCR can be performed, for example, under the conditions described in Example 1. The synthesized DNA fragments can be labeled by amplifying the fragments by PCR using primers which are labeled with isotopes, such as $^{32}P$; fluorescent dyes; biotin; and so on, or by adding into the PCR solution substrate nucleotides which are labeled with isotopes, such as $^{32}P$; fluorescent dyes; biotin; and so on. Alternatively, the labeling of the DNA fragments can be carried out by adding after PCR substrate nucleotides labeled with isotopes, such as $^{32}P$; fluorescent dyes; biotin; and so on, to the synthesized DNA fragment using the Klenow enzyme and such. Then, the obtained labeled DNA fragments are denatured by heating and the like, to be subjected to electrophoresis on a polyacrylamide gel without a denaturant, such as urea. The condition for separating DNA fragments in the electrophoresis can be improved by adding appropriate amounts (about 5 to 10%) of glycerol to the polyacrylamide gel. Further, although the condition for electrophoresis varies depending on the character of respective DNA fragments, it is usually carried out at room temperature (20 to 25° C.). In the event a preferable separation is not achieved at this temperature, a temperature to achieve the optimum mobility may be selected from temperatures between 4 to 30° C. After the electrophoresis, the mobility of the DNA fragments is detected by autoradiography with X-ray films, scanner for detecting fluorescence, and the like, to analyze the result. When a band with different mobility is detected, the presence of a mutation can be confirmed by directly excising the band from the gel, amplifying it again by PCR, and directly sequencing the amplified fragment. Further, without using labeled DNAs, the bands can be also detected by staining the gel after electrophoresis with ethidium bromide, silver, and such.

Another embodiment of the test method of this invention comprises the steps of; (a) preparing a DNA sample from a subject, (b) cleaving the DNA, (d) separating the DNA fragments depending on their length, (e) hybridizing the separated DNA fragment to a detectably labeled probe DNA of this invention, and (f) comparing the length of the detected DNA fragment with that of healthy controls. Moreover, after preparing the DNA sample of (a), a step may be included which consists of amplifying the DNA derived from the subject using the primer DNA of this invention.

The above method may, for example, utilize the Restriction Fragment Length Polymorphism/RFLP, the PCR-RFLP method, and the like. Restriction enzymes are generally used as enzymes to cleave DNAs. Specifically, when a polymorphic site exists in the recognition site of a restriction enzyme, or when insertion(s) or deletion(s) of nucleotide(s) exists in a DNA fragment generated by a restriction enzyme treatment, the fragments generated after the restriction enzyme treatment differ in terms of size from those of healthy individuals. The portion containing the polymorphic site is amplified by PCR, and then, is treated with respective restriction enzymes to detect the polymorphic site as a difference in the mobility of bands by electrophoresis. Alternatively, a polymorphic site on the chromosomal DNA can be detected by treating the chromosomal DNA with these restriction enzymes, subjecting the fragments to electrophoresis, and then, carrying out Southern blotting with a probe DNA. The restriction enzymes to be used can be appropriately selected in accordance with respective polymorphic sites. The Southern blotting can be conducted not only on the genomic DNA but also on cDNAs directly digested with restriction enzymes, wherein the cDNAs are synthesized by a reverse transcriptase from RNAs prepared from subjects. Alternatively, after amplifying a part or whole of the MHC S gene by PCR using the cDNA as a template, the cDNAs can be digested with restriction enzymes, and the difference of mobility can be examined.

Another embodiment of the test method of the present invention comprises the steps of: (a) preparing a DNA sample from a subject, (b) amplifying the DNA using a primer of this invention, (c) separating the amplified DNA on a gel comprising DNA denaturant with a gradually increasing concentration, and (d) comparing the mobility of the separated DNA on the gel with that of healthy controls.

The denaturant gradient gel electrophoresis method (DGGE method) can be exemplified as one of such methods. A region containing a target site of the MHC S gene, SEEK1 gene, or HCR gene is amplified by PCR and the like with a primer of the present invention and such; electrophoresed on a polyacrylamide gel with gradient concentration of denaturant, such as urea; and the result is compared with that of a healthy individual. A polymorphism can be identified by detecting the difference in mobility of the DNA fragments, since the mobility speed of a fragment with mutations slows down to an extreme degree due to the separation into single-stranded DNAs at the part of the gel where the concentration of the denaturant is lower.

In addition to the above-mentioned methods, the Allele Specific Oligonucleotide (ASO) hybridization method can be also used. An oligonucleotide having a nucleotide sequence, wherein a polymorphism is predicted to exist, is prepared, and is subjected to hybridization with a DNA sample. The efficiency of hybridization is reduced due to the existence of a polymorphic nucleotide that is different from the oligonucleotide in the sample DNA used for hybridization. The decrease of the hybridization efficiency can be detected by the Southern blotting method; methods which utilize specific fluorescent reagents that have a characteristic to quench by intercalation into the gap of the hybrid; and the like.

Furthermore, the detection may be also conducted by the ribonuclease A mismatch truncation method. Specifically, a region containing a target site of the MHC S gene, SEEK1 gene, or HCR gene is amplified by PCR and the like, and the amplified products are hybridized with labeled RNAs, wherein the RNAs are prepared from a healthy-type cDNA and such to be incorporated into a plasmid vector and the like. A polymorphism can be detected by autoradiography and the like, after cleaving with ribonuclease A sites of the hybrid that form a single-stranded conformation due to the existence of a nucleotide which is different from the healthy-type.

The present invention also provides DNAs including the polymorphisms of the MHC S gene, SEEK1 gene, and HCR gene, which are useful in the testing of psoriasis vulgaris.

The DNAs of the invention include DNAs comprising a nucleotide sequence that includes the 4040th nucleotide of the MHC S gene (a DNA consisting of the nucleotide sequence of SEQ ID NO:1 or the sequence of SEQ ID NO:1 wherein the 4040th nucleotide has been substituted with another nucleotide); DNAs comprising a nucleotide sequence that includes the 6413th nucleotide of the SEEK1 gene (a DNA consisting of the nucleotide sequence of SEQ ID NO:2 or the sequence of SEQ ID NO:2 wherein the 6413th nucleotide has been substituted with another nucleotide); DNAs comprising a nucleotide sequence that includes the 14378th nucleotide of the SEEK1 gene (a DNA consisting of the nucleotide sequence of SEQ ID NO:2 or the sequence of SEQ ID NO:2 wherein the 14378th nucleotide has been substituted with another nucleotide), and DNAs comprising a nucleotide sequence that includes the 6196th nucleotide of HCR gene (a DNA consisting of the nucleotide sequence of SEQ ID NO:3 or the sequence of SEQ ID NO:3 wherein the 6196th nucleotide has been substituted with another nucleotide).

Although the length of a DNA of the invention is not limited so long as it contains the above-mentioned polymorphic sites, it is preferably from 10 to 200 bp, more preferably from 15 to 100 bp, and still more preferably from 15 to 30 bp.

A DNA of the present invention can be obtained by treating genomic DNA from a subject with a restriction enzyme or by conducting polymerase chain reaction with above-mentioned primer DNAs of the invention using the genomic DNA as a template. The DNA can be used as the sample for the detection of above-mentioned polymorphisms in the test for psoriasis vulgaris (the sample for genetic diagnosis). Furthermore, it can be used on a DNA chip (a basal plate bound with oligonucleotides) used in the test for psoriasis vulgaris.

The present invention also provides oligonucleotides that hybridize to a region containing the polymorphic site of above-mentioned DNA of this invention. Such an oligonucleotide preferably hybridizes specifically to a region containing the polymorphic site of above-mentioned DNA of this invention. Herein, the term "specifically" means that the oligonucleotide hybridizes to a region containing the polymorphic site of above-mentioned DNA of this invention but does not hybridizes to other regions. Such hybridization conditions can be suitably selected by one skilled in the art, and include, for example, low-stringent conditions exemplified as follows. Low-stringent conditions in washing after hybridization include, for example, 42° C., 5×SSC, and 0.1% SDS, and preferably, 50° C., 2×SSC, and 0.1% SDS. High-stringent conditions are more preferable and include, for example, 65° C., 0.1×SSC, and 0.1% SDS. DNAs with high homologies are expected to be efficiently obtained by elevating the temperature and diminishing the salt concentration from the condition comprising, typically, low temperature and high salt concentration. However, several factors, such as temperature and salt concentration, can also influence the stringency of hybridization and one skilled in the art can suitably select the factors to accomplish a similar stringency. Although the length of the oligonucleotide of this invention is not limited, so long as it hybridizes to a DNA region containing above-mentioned polymorphic site, it is preferably from 10 to 200 nucleotides, more preferably from 15 to 100 nucleotides, and still more preferably from 15 to 30 nucleotides. Oligonucleotides of the present invention may be used for purifying the above-described DNA of the invention and for preparing DNA chips to be used to test for psoriasis vulgaris.

DESCRIPTION OF DRAWINGS

FIG. 1 depicts a schematic illustration showing the novel four genes—HCR, SPR1, SEEK1, and STG genes—adjacent to MHC S gene in the HLA class I region. All of these genes are expressed in epidermal keratinocytes. "Cent" and "Tel" indicate centromere and telomere, respectively.

FIG. 2 depicts the nucleotide sequence and amino acid sequence of the MHC S gene (SEQ ID NOs:60 and 61, respectively) (corneodesmosomes). The boxes indicate 12 polymorphic sites. K, R, S, W, and Y in the sequence indicate the nucleotide polymorphisms represented in IUB code. Deletion is observed at underlined site "AAG" of +461 to 463. Underlined amino acid sequences in the region of 65 to 175 and 370 to 450 are expected to form glycine loops.

FIG. 3 depicts the nucleotide sequence and amino acid sequence of the MRC gene (SEQ ID NOs:62 and 63, respectively). R, Y, W, K, and M in the sequence indicate the nucleotide polymorphisms represented in RIB code. The underlined sequence i expected to form a leucine zipper.

DETAILED DESCRIPTION

The present invention will be described in detail below with reference to Examples, but is not be construed as being limited thereto.

EXAMPLE 1

Detection of Polymorphisms in the MHC S Gene of Japanese Psoriasis Patients

To clarify the relationship between psoriasis in Japanese patients and the MHC S gene, the present inventors analyzed genomic sequences of the MHC S gene from eighty Japanese patients with psoriasis and 100 healthy individuals.

Thirty-nine HLA homozygous B cell lines provided by the 10th International Histocompatibility Workshop; 10IHW) were used. Genomic DNAs were isolated from peripheral blood leukocytes and B cell lines using QIAmpDNA blood kit (QIAGEN).

All of DNA samples were amplified across the seven target regions in the MHC S locus by PCRs using the following primer sets and amplification conditions (Table 1):

mix (40 μM each), primers (0.5 μM of each) and genomic DNA (20 μg). Following assembly, the al cycling was performed with an initial denaturation at 94° C. for 1 mm followed by 30 shuttle cycles of denaturation at 94° C. for 30 sec and primer annealing and extension at specified temperatures described above for 1 mm. All reactions were performed in a 96-well plate on GENEAMP®PCR system 9700 thermocycler (PE Biosystems).

TABLE 1

| Primer name | Primer sequence Forward (F) | Reverse (R) | Annealing temperature | Product |
|---|---|---|---|---|
| S1_00 | GAAACACCCACGACTGCGA | AGGAGGAGACCAGCCAGCAG | 63 | 8E+05—8E+05 |
| S1_01 | TCCTCGAGCTGCCATCAGTC | GGCATGAGAGTCGCTTGAACC | 64 | 8E+05—8E+05 |
| S1_08a | CGAGAGGCCGATTACTGAGAT | GACTAGAGCCAGATCCGGAG | 60 | 8E+05—8E+05 |
| S2_01a | GGGTGGTTCTGCAGGATCTT | AGAGTGCGAGACGATGGG | 60 | 8E+05—8E+05 |
| S2_02a | CAGTGGCCAAAGCGTCAGC | AGCCGCCTCCACAGAGCT | 64 | 8E+05—8E+05 |
| S2_03 | AAATACTTCTCCAGCAACCCC | GGAAAACTTCAGGGTCAGCTAG | 60 | 8E+05—8E+05 |
| S2_04 | AGATCCCCTGCCGCTCCA | ACTTCTTCAGGCGTCAGAGGTGC | 66 | 8E+05—8E+05 |

(i)  5'-GAAACACCCACGACTGCGA-3' (SEQ ID NO:4)
and

5'-AGGAGGAGACCAGCCAGCAG-3' (SEQ ID NO:5)
(63° C., 512 bp);

(ii) 5'-TCCTCGAGCTGCCATCAGTC-3' (SEQ ID NO:6)
and

5'-GGCATGAGAGTCGCTTGAACC-3' (SEQ ID NO:7)
(64° C., 650 bp);

(iii) 5'-CGAGAGGCCGATTACTGAGAT-3' (SEQ ID NO:8)
and

5'-GACTAGAGCCAGATCCGGAG-3' (SEQ ID NO:9)
(60° C., 376 bp);

(iv) 5'-GGGTGGTTCTGCAGGATCTT-3' (SEQ ID NO:10)
and

5'-AGAGTGCGAGACGATGGG-3' (SEQ ID NO:11)
(60° C., 412 bp);

(v) 5'-CAGTGGCCAAAGCGTCAGC-3' (SEQ ID NO:12)
and

5'-AGCCGCCTCCACAGAGCT-3' (SEQ ID NO:13)
(64° C., 533 bp);

(vi) 5'-AAATACTTCTCCAGCAACCCC-3' (SEQ ID NO:14)
and

5'-GGAAAACTTCAGGGTCAGCTAG-3' (SEQ ID NO:15)
(60° C., 514 bp); and (vii) 5'-AGATCCCCTGCCGCTCCA-3' (SEQ ID NO:16)
and 5'-ACTTCTTCAGGCGTCAGAGGTGC-3' (SEQ ID NO:17)
(66° C., 504 bp).

PCR was performed in 20 μl of reaction mixture containing 0.5 units of AMPLITAQ® recombinant DNA polymerase suited to PCR reactions (PE Biosystems), 1× GENE-AMP® buffer PCR reaction buffer (PE Biosystems), dNTP 5 μl of the PCR product was incubated with 2.5 units of exonuclease I (EXO) and 0.5 units of shrimp alkaline phosphatase (SAP) (Amersham) at 37° C. for 15 min followed by 80° C. for 15 mm to inactivate the EXO/SAP. Then, an aliquot containing about $10^{11}$ copies of the PCR fragment was mixed in a solution of 20 μl containing 1 μl of BIGDYE TERMINATOR® ready reaction mix sequencing reagent (PE Biosystems), 3.5 μl of 5× sequencing buffer (PE Biosystems), and 3.2 μM of unilateral primer of the primer set shown in Table 1. Excess dye-terminators were removed using gel. The filtrated sequencing products were automatically loaded onto an ABI PRISM® 3700_DNA analyzer (PE Biosystems) and the sequence thereof was determined.

By sequencing the entire genomic of the MHC S gene for Japanese psoriasis patients and healthy controls, 22 dimorphic sites in total, within two coding exons, were found as shown in Table 2. Twelve of the 22 sites were predicted to result in amino acid alteration, and three of these sites at cDNA positions +619, +1240, and +1243 were previously reported as polymorphisms. There was a deletion site at nucleotide position +461 to 3 which corresponds to Ser at amino acid position 150, and it was found that the deletion does not alter any amino acids in the following region. Similar amino acid substitutions were found in two domains (the 65 to 175 and 370 to 450 amino acid regions) which form glycine loops that are predicted to be involved in putative adhesion properties of the corneodesmosin (Guerrin et al., J. Biol. Chem. 273:22640–22647, 1998; Steinert et al., Int. J. Biol. Macromol. 13:130–139, 1991).

TABLE 2

Genetic polymorphisms in the coding region of the MHC S gene

| Nucleotide position | DMA polymorphism | | Amino acid position | Amino acid substitution | |
|---|---|---|---|---|---|
| 137 † | C | T | 41 | Pro | Pro |
| 206 † | C | T | 64 | Gly | Gly |
| 442 | G | A | 143 | Ser | Asn |
| 461-3 | AAG | del AAG | 150 | Ser | del Ser |

TABLE 2-continued

Genetic polymorphisms in the coding region of the MHC S gene

| Nucleotide position | DMA polymorphism | | Amino acid position | Amino acid substitution | |
| --- | --- | --- | --- | --- | --- |
| 465 | A | T | 151 | Ser | Cys |
| 470 | C | G | 152 | Ser | Arg |
| 614 † | A | G | 200 | Gln | Gln |
| 619 † | C | T | 202 | Ser | Phe |
| 683 | C | T | 223 | Pro | Pro |
| 722 | T | C | 236 | Ser | Ser |
| 767 † | G | A | 251 | Arg | Arg |
| 858 | C | A | 282 | Pro | Thr |
| 971 † | T | C | 319 | Tyr | Tyr |
| 1118 † | G | A | 368 | Ala | Ala |
| 1215 | A | G | 401 | Ser | Gly |
| 1236 | G | T | 408 | Ala | Ser |
| 1240 † | G | T | 409 | Gly | Val |
| 1243 † | C | T | 410 | Ser | Leu |
| 1331 | G | C | 439 | Ser | Ser |
| 1358 | T | C | 448 | Cys | Cys |
| 1372 | G | A | 453 | Ser | Asn |
| 1593 | G | A | 527 | Asp | Asn |

†: Polymorphisms previously reported by Ishihara et al.

sons by Bonferroni correction (Pc; corrected probability). A level of Pc<0.05 was accepted as statistically significant. Odds ratio of the risk to psoriasis vulgaris was calculated from the 2×2 contingency table. Odds ratio of homozygotes was calculated by comparing their risk with that for individuals having different alleles.

As a result, none of the alleles at the twelve positions, including the +1243 position of cDNA, showed either a positive or negative association with the disease when evaluated by simple P value test. This result coincides with previous results of the present inventors. However, the frequency of homozygotes at one of these alleles, position +1236 (position 825706 in the genomic region of FIG. 1, and position 4040 in the genomic DNA of SEQ ID NO:1), was significantly higher in psoriasis patients as compared with healthy individuals (Table 3). Specifically, the homozygous odds ratio ($OR_{HOM}$) of the allele (Ser) at +1236 was significantly higher compared to that of other alleles ($OR_{HOM}$= 5.14, $P_c$=0.00034). Interestingly, there was no individual homozygous for another allele (Ala) at position +1236, within 80 psoriasis patients, as compared with 3 out of 100 healthy individuals (3%).

TABLE 3

Association analyses of MHC S gene polymorphisms in Japanese psoriasis patients

| Nucleotide position | Allele (amino acid) | Allelic frequencies | | Homozygous frequencies | | $OR_{HOM}$* (95% CI) | Pc |
| --- | --- | --- | --- | --- | --- | --- | --- |
| | | Patients | Healthy | Patients | Healthy | | |
| 442 | G (Ser) | 0.87 | 0.85 | 0.74 | 0.72 | 1.13 (0.68–2.20) | >0.05 |
| | A (Asn) | 0.13 | 0.15 | 0 | 0.03 | | |
| 461-3 | AAG (Ser) | 0.76 | 0.77 | 0.6 | 0.6 | | |
| | del AAG (del Ser) | 0.24 | 0.23 | 0.09 | 0.07 | 1.31 (0.44–3.91) | >0.05 |
| 465 | A (Ser) | 0.98 | 0.98 | 0.96 | 0.95 | 1.32 (0.31–5.68) | >0.05 |
| | T (Cys) | 0.02 | 0.02 | 0 | 0 | | |
| 470 | C (Ser) | 0.98 | 0.98 | 0.96 | 0.95 | | |
| | G (Arg) | 0.02 | 0.02 | 0 | 0 | | |
| 619 | C (Ser) | 0.39 | 0.23 | 0.16 | 0.04 | 4.66 (1.46–14.9) | >0.05 |
| | T (Phe) | 0.61 | 0.77 | 0.38 | 0.59 | | |
| 858 | C (Pro) | 0.99 | 0.99 | 0.97 | 0.98 | | |
| | A (Thr) | 0.01 | 0.01 | 0 | 0 | | |
| 1215 | A (Ser) | 0.97 | 1 | 0.94 | 1 | | |
| | G (Gly) | 0.03 | 0 | 0 | 0 | | |
| 1236 | G (Ala) | 0.06 | 0.22 | 0 | 0.03 | | |
| | T (Ser) | 0.94 | 0.78 | 0.89 | 0.59 | 5.14 (2.30–11.4) | 3E–04 |
| 1240 | G (Gly) | 0.91 | 0.94 | 0.85 | 0.89 | | |
| | T (Val) | 0.09 | 0.06 | 0.03 | 0.01 | 2.52 (0.22–28.3) | >0.05 |
| 1243 | C (Ser) | 0.63 | 0.62 | 0.42 | 0.40 | 1.09 (0.59–1.98) | >0.05 |
| | T (Leu) | 0.37 | 0.38 | 0.15 | 0.15 | | |
| 1372 | G (Ser) | 0.85 | 0.88 | 0.76 | 0.98 | | |
| | A (Asn) | 0.15 | 0.12 | 0.06 | 0.01 | 6.55 (0.75–57.3) | >0.05 |
| 1539 | G (Asp) | 0.84 | 0.82 | 0.71 | 0.69 | 1.15 (0.60–2.21) | >0.05 |
| | A (Asn) | 0.16 | 0.18 | 0.04 | 0.03 | | |

$OR_{HOM}$*:ORHOM*: Homozygote Odd Ratios and 95% confidence intervals (CI) were calculated for alleles whose homozygote frequencies had been increased.
Pc: Bonferroni correction applied for each test.

Next, association analyses were conducted for all polymorphic sites in the MHC S gene. Statistical analyses were performed based on the determined sequence information. Allele frequencies were determined by direct counting. The statistically significant differentiation of allele distribution between patients and healthy individuals was tested by the chi-square ($\chi^2$) method and Fisher's exact probability test (P value test). The P value was corrected for multiple compari- Next, 39 B cell lines derived from Caucasian populations which are homozygous for HLA were analyzed. Genome DNA was isolated from each of the cell lines using QIAGEN Genomic-tip system (QIAGEN). As a result, the same allele (Ser) at position +1236 was found (Table 4). Twelve cell lines had this allele concurrently with HLA-Cw6/7, and the linkage disequilibrium between this allele and HLA-Cw6/7 seemed to be stronger than that between any alleles at position +1246 and HLA-Cw6/7. Among these 12 cell lines, COX and VAVY cell lines, which carried an ancestral haplotype (AH8.1) associated with psoriasis (Jenisch et al., Tissue Antigens 53:135–146, 1999), had the same allele (Ser) at position +1236.

TABLE 4

+1236 and +1243 polymorphisms of the MHC S gene in HLA homozygous B cell lines

| B cell line | HLA antigens | | | MHC S gene | | Ethnic origin |
|---|---|---|---|---|---|---|
| | A | C | B | 1236 | 1243 | |
| 9005 HOM2 | 3 | 1 | 27 | G | C | Canadian |
| 9092 BM92 | 25 | 1 | 51 | G | C | Italian |
| 9067 BTB | 2 | 1 | 27 | G | C | Scandinavian |
| 9037 SWEIG007 | 29 | 2 | 61 | T | C | North American Caucasoid |
| 9025 DEU | 31 | 4 | 35 | T | C | Dutch |
| 9068 BM9 | 2 | 4 | 35 | T | T | Italian |
| 9104 DHIF | 31 | 5 | 38 | T | C | English |
| 9019 DUCAF | 30 | 5 | 18 | G | C | French |
| 9036 SPO010 | 2 | 5 | 44 | G | C | Italian |
| 9039 JVM | 2 | 5 | 18 | G | C | Dutch |
| 9020 QBL | 26 | 5 | 18 | G | C | Dutch |
| 9047 PLH | 3 | 6 | 47 | T | C | Scandinavian |
| 9048 LBUF | 30 | 6 | 13 | T | C | English Caucasoid |
| 9052 DBB | 2 | 6 | 57 | T | C | Amish |
| 9014 MGAR | 26 | 7 | 8 | T | T | North American Hispanic |
| 9013 SCHU | 3 | 7 | 7 | T | T | French |
| 9033 BM14 | 3 | 7 | 7 | T | T | Italian |
| 9022 COX † | 1 | 7 | 8 | T | T | South African Caucasoid |
| 9023 VAVY † | 1 | 7 | 8 | T | T | French |
| 9040 BM15 | 1 | 7 | 49 | T | C | Italian |
| 9065 HHKB | 3 | 7 | 7 | T | T | Dutch |
| 9034 SAVC | 3 | 7 | 7 | T | T | French |
| 9082 HO104 | 3 | 7 | 7 | T | T | French |
| 9061 31227ABO | 2 | 7 | 18 | G | C | Italian |
| 9029 WT51 | 23 | 8 | 65 | T | T | Italian Aosta |
| 9060 CB6B | 1 | 9 | 62 | T | T | Australian Caucasoid |
| 9091 MLF | 2 | 9 | 62 | T | C | English |
| 9032 BSM | 2 | 9 | 62 | T | C | Dutch |
| 9069 MADURA | 2 | 10 | 60 | T | C | Danish |
| 9059 SLE005 | 2 | 10 | 60 | T | C | North American Caucasoid |
| 9050 MOU | 29 | — | 44 | T | C | Danish |
| 9051 PITOUT | 29 | — | 44 | T | C | South African Caucasoid |
| 9057 TEM | 26 | — | 38 | G | C | Jewish |
| 9062 WDV | 2 | — | 38 | G | C | Dutch |
| 9003 KAS116 | 24 | — | 51 | G | C | Yugoslavian |
| 9070 LUY | 2 | — | 51 | T | T | Dutch |
| 9011 E4181324 | 1 | — | 52 | T | T | Australian Caucasoid |
| 9026 YAR | 26 | — | 38 | G | C | Ashkenasi Jewish |
| 9106 MANIKA | 3 | — | 50 | T | C | South African Caucasoid |

†: Cell lines carrying an ancestral haplotype (AH8.1) associated with psoriasis.

EXAMPLE 2

Detection of Polymorphism in SEEK1 Gene of Japanese Psoriasis Patients

The present inventors newly analyzed genomic sequences of the SEEK1 gene of 80 Japanese psoriasis patients and 100 healthy individuals to identify the relationship between the SEEK1 gene and Japanese psoriasis. Genomic DNA was isolated from the peripheral blood leukocyte using QIAmp-DNA blood kit (QIAGEN).

All of the DNA samples were amplified across the five target regions in the SEEK1 locus by PCRs using the following primer sets and amplification conditions (Table 5):

(i)
5'-TGGAGGAGTGTAACGAAGGTTTCTG-3'     (SEQ ID NO:18)
and
5'-TCTGGCAGCCACCCAGGA-3'            (SEQ ID NO:19)
(65°C., 470 bp);

(ii)
5'-GCAGGACTGATGCAAACA-3'            (SEQ ID NO:20)
and
5'-CTCCCTATCATGACCCAGAG-3'          (SEQ ID NO:21)
(55° C., 529 bp);

(iii)
5'-GAAATGGCTTTCTGGACACATTGG-3'      (SEQ ID NO:22)
and
5'-CTCGGTCCTCTGCGGGTG-3'            (SEQ ID NO:23)
(65° C., 586 bp);

(iv)
5'-CTACATGTGGTCCGAATG-3'            (SEQ ID NO:24)
and
5'-ACGAGAGCTCATCACCTG-3'            (SEQ ID NO:25)
(52° C., 529 bp); and (v)
5'-CAAGGCCATCAGTGAATCCCT-3'         (SEQ ID NO:26)
and
5'-TGTGCTTCCCCTTTCTACCTTA-3'        (SEQ ID NO:27)
(63° C., 143 bp).

PCR was performed in 20 μl of reaction mixture containing 0.5 units of AMPLITAQ® recombinant DNA polymerase suited to PCR reactions (PE Biosystems), 1× GENE-AMP® buffer PCR reaction buffer (PE Biosystems), dNTP mix (40 μM each), primers (0.5 μM of each), and genomic DNA (20 μg). Following assembly, thermal cycling was performed with an initial denaturation at 94° C. for 1 mm followed y 30 shuttle cycles of denaturation at 94° C. for 30 sec and primer annealing and extension for 1 mm at specified temperatures described above. All reactions were performed in a 96- ell plate on a GENEAMP® PCR system 9700 thermocycler (PE Biosystems).

TABLE 5

| Primer name | Primer sequence | | Annealing temperature | Product |
|---|---|---|---|---|
| | Forward (F) | Reverse (R) | | |
| 1_05 | TGGAGGAGTGTAACGAAGGTTTCTG | TCTGGCAGCCACCCAGGA | 65 | 801924–802393 |
| 1_06 | GCAGGACTGATCGGAACA | CTCCCTATCATGACCCAGAG | 55 | 802299–802827 |

TABLE 5-continued

| Primer name | Primer sequence | | Annealing temperature | Product |
|---|---|---|---|---|
| | Forward (F) | Reverse (R) | | |
| 1_08 | GAAATGGCTTTCTGGACACATTGG | CTCGGTCCTCTGCGGGTG | 65 | 803235–803820 |
| 3_17 | CTACATGTGGTCCGAATG | ACGAGAGCTCATCACCTG | 52 | 808104–808632 |
| 5_2a | CAAGGCCATCAGTGAATCCCT | TGTGCTTCCCCTTTCTACCTTA | 63 | 816031–816173 |

5 μl of the PCR product was incubated with 2.5 units of exonuclease I (EXO) and 0.5 units of shrimp alkaline phosphatase (SAP) (Amersham) at 37° C. for 15 mm followed by 80° C. for 15 mm to inactivate the EXO/SAP. Then, an aliquot containing about $10^{11}$ copies of the PCR fragment was mixed in a solution of 20 ∥l containing 1 μl of BIGDYE TERMINATOR® ready reaction mix sequencing reagent (PE Biosystems), 3.5 ∥l of 5× sequencing buffer (PE Biosystems), and 3.2 μM of unilateral primer of the primer set shown in Table Excess dye-terminators were removed by gel. The filtrated sequencing products were automatically loaded onto an ABI PRISM® 3700_DNA analyzer (PE Biosystems) and the sequence as determined.

TABLE 6

| SEEK1 exon | Nucleotide position | Sequencing primer | DNA polymorphism | |
|---|---|---|---|---|
| 8 | 802129 | 1_05R | G | del G |
| | 802205 | 1_06R | G | A |
| 7 | 803337 | 1_08F | G | A |
| | 803352 | 1_08F | G | ins G |
| | 803364 | 1_08R | T | C |
| | 803394 | 1_08R | G | T |
| 6a | 803617 | 1_08R | C | T |
| | 803676 | 1_08R | G | A |
| 6b | 803617 | 1_08R | C | T |
| 4 | 808327 | 3_17F | A | G |
| | 808422 | 3_17F | C | A |
| | 808428 | 3_17F | T | C |
| | 808452 | 3_17F | C | T |
| | 808453 | 3_17F | G | A |
| | 808524 | 3_17F | C | T |
| 2a | 816288 | 5_2aF | C | T |
| | 816370 | 5_2aF | C | T |
| | 816390 | 5_2aF | C | T |
| | 816393 | 5_2aF | T | C |
| 2b | 816288 | 5_2aF | C | T |

By the entire genomic sequencing of the SEEK1 gene of Japanese psoriasis patients and healthy controls, 20 dimorphic sites in total within a single exon were found as shown in Table 6.

Next, association analyses were conducted for all polymorphic sites in the SEEK1 gene. Statistical analyses were performed based on the determined sequence information. Allele frequencies were determined by direct counting. The statistically significant differentiation of allele distribution between patients and healthy individuals was tested by the chi-square ($\chi^2$) method and Fisher's exact probability test (P value test). The P value was corrected for multiple comparisons by Bonferroni correction (Pc; corrected probability). A level of Pc<0.05 was accepted as statistically significant. Odds ratio of the risk to psoriasis vulgaris was calculated from the 2×2 contingency table. Odds ratio of homozygotes was calculated by comparing their risk with that for individuals having different alleles. SNP polymorphisms displaying statistically significant differentiation are represented by "*".

As a result, the frequency of homozygotes for alleles at position 808428 and 816393 in the genomic DNA region of FIG. 1 (position 6413 and 14378 in the genomic DNA sequence of SEQ ID NO:2) was significantly increased in psoriasis patients as compared with healthy individuals (Table 7).

TABLE 7

Association analyses of SEEK1 gene polymorphisms in Japanese

| Nucleotide position | Allele | Allelic frequencies | | Homozygous frequencies | | $OR_{HOM}$* (95% CI) | Pc |
|---|---|---|---|---|---|---|---|
| | | Patients | Healthy | Patients | Healthy | | |
| 802129 | G | 0.84 | 0.87 | 0.76 | 0.76 | 1.04 (0.52–2.08) | >0.05 |
| | del G | 0.16 | 0.13 | 0.08 | 0.01 | 7.87 (0.93–66.8) | >0.05 |
| 802205 | G | 0.83 | 0.87 | 0.75 | 0.76 | | |
| | A | 0.18 | 0.13 | 0.10 | 0.01 | 10.78 (1.32–88.1) | >0.05 |
| 803337 | G | 0.90 | 0.83 | 0.81 | 0.67 | 2.13 (1.06–4.30) | >0.05 |
| | A | 0.10 | 0.18 | 0.01 | 0.02 | | |
| 803352 | — | 0.78 | 0.84 | 0.65 | 0.70 | | |
| | ins G | 0.23 | 0.16 | 0.10 | 0.02 | 5.39 (1.11–26.1) | >0.05 |
| 803364 | T | 0.00 | 0.00 | 0.00 | 0.00 | | |
| | C | 1.00 | 1.00 | 1.00 | 1.00 | | |
| 803394 | G | 0.94 | 0.96 | 0.88 | 0.93 | | |
| | T | 0.06 | 0.04 | 0.00 | 0.00 | | |

TABLE 7-continued

Association analyses of SEEK1 gene polymorphisms in Japanese

| Nucleotide position | Allele | Allelic frequencies Patients | Allelic frequencies Healthy | Homozygous frequencies Patients | Homozygous frequencies Healthy | OR$_{HOM}$* (95% CI) | Pc |
|---|---|---|---|---|---|---|---|
| 803617 | C | 0.92 | 0.82 | 0.85 | 0.68 | 2.63 (1.25–5.54) | >0.05 |
|  | T | 0.08 | 0.18 | 0.00 | 0.03 |  |  |
| 803676 | G | 0.08 | 0.12 | 0.00 | 0.01 |  |  |
|  | A | 0.92 | 0.88 | 0.84 | 0.78 | 1.47 (0.69–3.15) | >0.05 |
| 808327 | A | 0.91 | 0.88 | 0.84 | 0.76 | 1.63 (0.77–3.45) | >0.05 |
|  | G | 0.09 | 0.12 | 0.01 | 0.00 |  |  |
| 808422 | C | 0.91 | 0.90 | 0.85 | 0.80 | 1.42 (0.65–3.12) | >0.05 |
|  | A | 0.09 | 0.11 | 0.03 | 0.01 | 2.54 (0.23–28.5) | >0.05 |
| 808428 | T | 0.56 | 0.37 | 0.31 | 0.12 | 3.33 (1.55–7.17) | 0.04 * |
|  | C | 0.44 | 0.63 | 0.20 | 0.38 |  |  |
| 808452 | C | 0.91 | 0.88 | 0.84 | 0.75 | 1.72 (0.81–3.63) | >0.05 |
|  | T | 0.09 | 0.13 | 0.01 | 0.00 |  |  |
| 808453 | G | 0.84 | 0.89 | 0.74 | 0.79 |  |  |
|  | A | 0.16 | 0.12 | 0.05 | 0.02 | 2.58 (0.46–14.5) | >0.05 |
| 808524 | C | 0.91 | 0.88 | 0.84 | 0.75 | 1.72 (0.81–3.63) | >0.05 |
|  | T | 0.09 | 0.13 | 0.01 | 0.00 |  |  |
| 816288 | C | 0.76 | 0.76 | 0.59 | 0.56 | 1.13 (0.62–2.06) | >0.05 |
|  | T | 0.24 | 0.24 | 0.08 | 0.04 | 1.89 (0.51–6.93) | >0.05 |
| 816370 | C | 0.99 | 0.97 | 0.98 | 0.95 | 2.10 (0.40–11.1) | >0.05 |
|  | T | 0.01 | 0.03 | 0.00 | 0.01 |  |  |
| 816390 | C | 0.84 | 0.74 | 0.69 | 0.55 | 1.80 (0.97–3.33) | >0.05 |
|  | T | 0.16 | 0.26 | 0.01 | 0.07 |  |  |
| 816393 | T | 0.66 | 0.48 | 0.44 | 0.17 | 3.84 (1.92–7.70) | 0.003 * |
|  | C | 0.34 | 0.52 | 0.13 | 0.20 |  |  |

OR$_{HOM}$*: Homozygote Odd Ratios and 95% confidence intervals (CI) were calculated for alleles whose homozygote frequencies had been increased.
Pc: Bonferroni correction applied for each test.

EXAMPLE 3

Detection of Polymorphism in HCR Gene of Japanese Psoriasis Patients

The present inventors newly analyzed the genomic sequences of the HCR gene of 80 Japanese psoriasis patients and 100 healthy individuals to identify the relationship between the HCR gene and Japanese psoriasis. Genomic DNA was isolated from peripheral blood leukocyte using QIAmpDNA blood kit (QIAGEN).

All of DNA samples were amplified across the 16 target regions in the HCR locus by PCRs using the following primer sets and amplification conditions (Table 8):

(i) 5'-CCTCCCACTTTCAAGCTCG-3' (SEQ ID NO:28)
and
5'-GAGGAAGGGTCACTAGCAAGC-3' (SEQ ID NO:29)
(65° C., 247 bp);

(ii) 5'-CCCTCAACTATCCTTCCAGCA-3' (SEQ ID NO:30)
and
5'-TTGGAAGCTACTGCCCAGC-3' (SEQ ID NO:31)
(60° C., 425 bp);

(iii) 5'-CAGAAAGTGGGAGTGAAGGGA-3' (SEQ ID NO:32)
and
5'-ATGGGACAGCCATCAGTGG-3' (SEQ ID NO:33)
(65° C., 324 bp);

(iv) 5'-CCAGCAATTAGTGATGTGGTGG-3' (SEQ ID NO:34)
and
5'-TCTACACGCTCCTCCAAGGG-3' (SEQ ID NO:35)
(66° C., 289 bp);

(v) 5'-CGGGAGAGAAGGTGGTACCTAA-3' (SEQ ID NO:36)
and
5'-AACATGAGCTACAGCAAGAGGAGT-3' (SEQ ID NO:37)
(62° C., 327 bp);

(vi) 5'-GAGGAGAAACAAAGATGCCACC-3' (SEQ ID NO:38)
and
5'-GATGCCACCTTCATGGAAGG-3' (SEQ ID NO:39)
(65° C., 294 bp);

(vii) 5'-ACCTGCCACTTTGCTTCCAG-3' (SEQ ID NO:40)
and
5'-ATGCAGCAAAGGACAGGGTC-3' (SEQ ID NO:41)
(65° C., 285 bp);

(viii) 5'-GCTGCAGCCAGGACTTAGG-3' (SEQ ID NO:42)
and
5'-AACAAGGTGCCCAGGAACC-3' (SEQ ID NO:43)
(62° C., 224 bp);

(ix) 5'-ATGGGACAGGATTAGAGGGAGTT-3' (SEQ ID NO:44)
and
5'-GGATGTGGGATCAGAGAGAGCT-3' (SEQ ID NO:45)
(62° C., 351 bp);

(x) 5'-CCTTACTCCCTGTCCCCACTT-3' (SEQ ID NO:46)
and

-continued (x) 5'-CCTCAGTCCTCATGGTTTTGG-3' (SEQ ID NO:47)
(62° C., 194 bp);

(xi) 5'-CCCAAAACCATGAGGACTGA-3' (SEQ ID NO:48)
and

5'-CTCTCCACCCTCTGGCAAC-3' (SEQ ID NO:49)
(56° C., 254 bp);

(xii) 5'-AGAGGATGAGGAAAAACCCAGTG-3' (SEQ ID NO:50)
and

5'-GGCATATCAGCAGGAGCTTTG-3' (SEQ ID NO:51)
(63° C., 332 bp);

(xiii) 5'-GGGTGGGAACTGCGAATC-3' (SEQ ID NO:52)
and

5'-TGAAGCTTTGAACACACTTTGAG-3' (SEQ ID NO:53)
(56° C., 256 bp);

(xiv) 5'-TGTTCCTGTCTTCATGGTGCC-3' (SEQ ID NO:54)
and

5'-TCTTTCCACACCTCTAGCCCAG-3' (SEQ ID NO:55)
(61° C., 305 bp);

(xv) 5'-TGGGCTAGAGGTGTGGAAAGA-3' (SEQ ID NO:56)
and

5'-TCATCATGCCAGAGTCTGAAGAG-3' (SEQ ID NO:57)
(60° C., 322 bp); and (xvi) 5'-CCAGCCCTGTTTCCTCTGT-3' (SEQ ID NO:58)
and 5'-GTCTGTCCCCACCCACTTC-3' (SEQ ID NO:59)
(61° C., 266 bp).

TABLE 8

| Primer name | Primer sequence | | Annealing temperature | Product |
|---|---|---|---|---|
| | Forward primer | Reverse primer | | |
| HCR_01F,R | CCTCCCACTTTCAAGCTCG | GAGGAAGGGTCACTAGCAAGC | 65 | 765142–785388 |
| HCR_02F,R | CCCTCAACTATCCTTCCAGCA | TTGGAAGCTACTGCCCAGC | 60 | 787221–787644 |
| HCR_03F,R | CAGAAAGTGGGAGTGAAGGGA | ATGGGACAGCCATCAGTGG | 65 | 790889–791212 |
| HCR_04F,R | CCAGCAATTAGTGATGTGGTGG | TCTACACGCTCCTCCAAGGG | 66 | 791158–791446 |
| HCR_05F,R | CGGGAGAGAAGGTGGTACCTAA | AACATGAGCTACAGCAAGAGGAGTT | 62 | 791457–791783 |
| HCR_06F,R | GAGGAGAAACAAAGATGCCACC | GATGCCACCTTCATGGAAGG | 65 | 791798–792091 |
| HCR_07F,R | ACCTGCCACTTTGCTTCCAG | ATGCAGCAAAGGACAGGGTC | 65 | 793286–793570 |
| HCR_08F,R | GCTGCAGCCAGGACTTAGG | AACAAGGTGCCCAGGAACC | 62 | 793528–793751 |
| HCR_09F,R | ATGGGACAGGATTAGAGGGAGTT | GGATGTGGGATCAGAGAGAGCT | 62 | 796178–796478 |
| HCR_10F,R | CCTTACTCCCTGTCCCCACTT | CCTCAGTCCTCATGGTTTTGG | 62 | 796520–796713 |
| HCR_11F,R | CCCAAAACCATGAGGACTGA | CTCTCCACCCTCTGGCAAC | 56 | 796692–796945 |
| HCR_12F,R | AGAGGATGAGGAAAAACCCAGTG | GGCATATCAGCAGGAGCTTTG | 63 | 796942–797273 |
| HCR_13F,R | GGGTGGGAACTGCGAATC | TGAAGCTTTGAACACACTTTGAG | 56 | 797236–797491 |
| HCR_14F,R | TGTTCCTGTCTTCATGGTGCC | TCTTTCCACACCTCTAGCCCAG | 61 | 798593–798897 |
| HCR_15F,R | TGGGCTAGAGGTGTGGAAAGA | TCATCATGCCAGAGTCTGAAGAG | 60 | 798877–799198 |
| HCR_16F,R | CCAGCCCTGTTTCCTCTGT | GTCTGTCCCCACCCACTTC | 61 | 799296–799561 |

PCR was performed in 20 μl of reaction mixture containing 0.5 units of AMPLITAQ® recombinant DNA polymerase suited to PCR reactions (PE Biosystems), 1× GENE-AMP® buffer PCR reaction buffer (PE Biosystems), dNTP mix (40 μM each), primers (0.5 μM of each), and genomic DNA (20 μg). Following assembly, thermal cycling was performed with an initial denaturation at 94° C. for 1 mm followed by 30 shuttle cycles of denaturation at 94° C. for 30 sec and primer annealing and extension for 1 mm at specified temperatures described above. All reactions were performed in a 96-well plate on a GENEAMP® PCR system 9700 thermocycler (PE Biosystems).

5 μl of the PCR product was incubated with 2.5 units of exonuclease I (EXO) and 0.5 units of shrimp alkaline phosphatase (SAP) (Amersham) at 37° C. for 15 min followed by 80° C. for 15 mm to inactivate the EXO/SAP. Then, an aliquot containing about $10^{11}$ copies of the PCR fragment was mixed in a solution of 20 μl containing 1 μl of BIGDYE TERMINATOR® ready reaction mix sequencing reagent (PE Biosystems), 3.5 μl of 5× sequencing buffer (PE Biosystems), and 3.2 μM of unilateral primer of the primer set shown in Table 8. Excess dye-terminators were removed by gel. The filtrated sequencing products were automatically loaded onto an ABI PRISM® 3700_DNA analyzer (PE Biosystems) and the sequence as determined.

By the entire genomic sequencing of the HCR gene of Japanese psoriasis patients and healthy controls, 12 dimorphic sites in total within exons were found as shown in Table 9. Eleven of the 12 sites were predicted to result in amino acid alteration.

TABLE 9

Genetic polymorphisms in the coding region of the HCR gene

| Nucleotide position | DMA polymorphism | Amino acid position | Amino acid substitution | |
|---|---|---|---|---|
| 249 | G | A | 76 | Arg Gln |
| 436 | G | C | 138 | Arg Ser |

TABLE 9-continued

Genetic polymorphisms in the coding region of the HCR gene

| Nucleotide position | DMA polymorphism | | Amino acid position | Amino acid substitution | |
|---|---|---|---|---|---|
| 715 | C | G | 231 | Val | Val |
| 769 | A | C | 249 | Glu | Asp |
| 1193 | T | C | 391 | Try | Arg |
| 1229 | T | C | 403 | Leu | Leu |
| 1824 | G | A | 601 | Arg | Gln |
| 1855 | G | A | 611 | Leu | Ile |
| 1861 | G | T | 613 | Gln | Tyr |
| 1887 | A | T | 622 | Lys | Met |
| 1910 | C | T | 630 | Arg | Cys |
| 2271 | G | C | 750 | Cys | Ser |

Next, association analyses were conducted for all polymorphic sites in the HCR gene. Statistical analyses were performed based on the determined sequence information. Allele frequencies were determined by direct counting. The statistically significant differentiation of allele distribution between patients and healthy individuals was tested by the chi-square ($\chi^2$) method and Fisher's exact probability test (P value test). The P value was corrected for multiple comparisons by Bonferroni correction (Pc; corrected probability). A level of Pc<0.05 was accepted as statistically significant. Odds ratio of the risk to psoriasis vulgaris was calculated from the 2×2 contingency table. Odds ratio of homozygotes was calculated by comparing their risk with that of individuals having different alleles. SNP polymorphisms displaying statistically significant differentiation are represented by "*".

As a result, the frequency of homozygotes at position 769 of the cDNA (position 791356 of the genomic region of FIG. 1, position 6196 of the nucleotide sequence of SEQ ID NO:3) was demonstrated to be significantly increased in patients compared with healthy individuals (Table 10).

TABLE 10

Genetic polymorphisms in the coding region of the HCR gene

| Nucleotide position | Allele (amino acid) | Allelic frequencies | | Homozygous frequencies | | $OR_{HOM}$* (95% CI) | Pc |
|---|---|---|---|---|---|---|---|
| | | Patients | Healthy | Patients | Healthy | | |
| 249 | G (Arg) | 0.82 | 0.88 | 0.72 | 0.75 | | |
| | A (Gln) | 0.18 | 0.13 | 0.08 | 0.00 | | |
| 436 | G (Arg) | 0.45 | 0.32 | 0.19 | 0.07 | 3.27 (0.88–12.1) | >0.05 |
| | C (Ser) | 0.55 | 0.68 | 0.28 | 0.42 | | |
| 769 | A (Glu) | 0.50 | 0.66 | 0.40 | 0.43 | | |
| | C (Asp) | 0.50 | 0.34 | 0.40 | 0.10 | 5.80 (2.77–12.1) | 0.000023 |
| 1193 | T (Try) | 0.23 | 0.34 | 0.04 | 0.09 | | |
| | C (Arg) | 0.77 | 0.66 | 0.58 | 0.42 | 1.98 (1.01–3.87) | >0.05 |
| 1824 | G (Arg) | 0.93 | 0.99 | 0.85 | 0.98 | | |
| | A (Gln) | 0.07 | 0.01 | 0.00 | 0.00 | | |
| 1855 | G (Leu) | 0.77 | 0.62 | 0.61 | 0.40 | 2.36 (1.27–4.37) | >0.05 |
| | A (Ile) | 0.23 | 0.38 | 0.07 | 0.16 | | |
| 1861 | G (Gln) | 0.90 | 0.82 | 0.80 | 0.67 | 1.97 (0.97–3.99) | >0.05 |
| | T (Tyr) | 0.10 | 0.18 | 0.00 | 0.02 | | |
| 1887 | A (Lys) | 0.93 | 0.87 | 0.87 | 0.80 | 1.67 (0.73–3.81) | >0.05 |
| | T (Met) | 0.07 | 0.13 | 0.00 | 0.05 | | |
| 1910 | C (Arg) | 0.92 | 0.89 | 0.87 | 0.77 | 1.91 (0.84–4.32) | >0.05 |
| | T (Cys) | 0.08 | 0.11 | 0.03 | 0.00 | | |
| 2271 | G (Cys) | 0.05 | 0.02 | 0.00 | 0.00 | | |
| | C (Ser) | 0.95 | 0.98 | 0.91 | 0.95 | | |

$OR_{HOM}$*: Homozygote Odd Ratios and 95% confidence intervals (CI) were calculated for alleles whose homozygote frequencies had been increased.
Pc: Bonferroni correction applied for each test.

INDUSTRIAL APPLICABILITY

The present invention provides genetic polymorphisms that exist in significantly high frequency in psoriasis vulgaris patients as compared with healthy individuals. Moreover, the present invention provides a test method for psoriasis vulgaris utilizing such genetic polymorphisms, and DNA molecules to be used for the test. The present invention enables one to readily test for psoriasis vulgaris.

What is claimed is:

1. A method of determining the risk of psoriasis vulgaris in a subject, the method comprising the step of detecting, in a sample prepared from the subject, a nucleotide polymorphism selected from the group of:
   (a) a polymorphism involving the 6413th nucleotide of SEQ ID NO:2 or a corresponding nucleotide on a complementary strand thereof; and
   (b) a polymorphism involving the 14378th nucleotide of SEQ ID NO:2 or a corresponding nucleotide on a complementary strand thereof;
   wherein when a polymorphism is detected that is associated with psoriasis vulgaris, the subject is determined to be at risk of psoriasis vulgaris.

2. The method according to claim 1, wherein the detecting step:
   (a) providing a DNA sample from a subject,
   (b) amplifying the DNA using primers selected from the group consisting of:
      (i) a first primer that hybridizes to a DNA consisting of the nucleotide sequence f SEQ ID NO:2 and a second primer that hybridizes to a DNA consisting of the nucleotide sequence of the complement of SEQ NO:2, wherein the primers are designed so that the 6413th nucleotide of SEQ ID NO:2 or the corresponding nucleotide on the complementary strand thereof is positioned between the respective sites to which the primers hybridize on SEQ ID NO:2 and the complement thereof; and
      (ii) a first primer that hybridizes to a DNA consisting of the nucleotide sequence of SEQ ID NO:2 and a second primer that hybridizes to a DNA consisting of the nucleotide sequence of the complement of SEQ ID NO:2, wherein the primers are designed so that the 14378th nucleotide of SEQ ID NO:2 or the corresponding nucleotide on the complementary strand thereof is positioned between the respective sites to which the primers hybridize on SEQ ID NO:2 and the complement thereof, and
   (c) determining the nucleotide sequence of the amplified DNA.

3. The method according to claim 1, wherein the detecting step comprises:
   (a) providing a DNA sample from a subject;
   (b) amplifying the DNA using primers selected from the group consisting of:
      (i) a first primer that hybridizes to a DNA consisting of the nucleotide sequence of SEQ ID NO:2 and a second primer that hybridizes to a DNA consisting of the nucleotide sequence of the complement of SEQ ID NO:2, wherein the primers are designed so that the 6413th nucleotide of SEQ ID NO:2 or the corresponding nucleotide on the complementary strand thereof is positioned between the respective sites to which the primers hybridize on SEQ ID NO:2; and
      (ii) a first primer that hybridizes to a DNA consisting of the nucleotide sequence of SEQ ID NO:2 and a second primer that hybridizes to a DNA consisting of the nucleotide sequence of the complement of SEQ ID NO:2 and the complement thereof, wherein the primers are designed so that the 14378th nucleotide of SEQ ID NO:2 or the corresponding nucleotide on the complementary strand thereof is positioned between the respective sites to which the primers hybridize on SEQ ID NO:2 and the complement thereof, and
   (c) dissociating the amplified DNA into single stranded DNA;
   (d) separating the dissociated single stranded DNA on a nondenaturing gel; and
   (e) detecting the presence of a polymorphism in the subject based on the mobility of the separated single stranded DNA on the gel.

4. The method of claim 1, wherein the subject has no symptoms of psoriasis vulgaris.

5. The method of claim 1, wherein the polymorphism detected comprises a T at the 6413th nucleotide of SEQ ID NO:2 or an A at the corresponding position on the complementary strand thereof, and the presence of the polymorphism indicates that the subject has an increased risk of psoriasis vulgaris.

6. The method of claim 1, wherein the polymorphism detected comprises a T at the 14378th nucleotide of SEQ ID NO:2 or an A at the corresponding position on the complementary strand thereof, and the presence of the polymorphism indicates at the subject has an increased risk of psoriasis vulgaris.

7. The method of claim 1, wherein the polymorphism is detected by detecting hybridization of a probe having a sequence comprising a polymorphism involving the 6413th nucleotide of SEQ ID NO:2, or a corresponding nucleotide on a complementary strand thereof, under high stringency conditions of 65° C. in 2×SSC and 0.1% SDS.

8. The method of claim 7, wherein the probe is from 10 to 200 nucleotides in length.

9. The method of claim 7, wherein the probe is from 15 to 100 nucleotides in length.

10. The method of claim 7, wherein the probe is from 15 to 30 nucleotides in length.

11. The method of claim 1, wherein the polymorphism is detected by detecting hybridization of a probe having a sequence comprising a polymorphism involving the 14378th nucleotide of SEQ ID NO:2, or a corresponding nucleotide on a complementary strand thereof, under high stringency conditions of 65° C. in 2×SSC and 0.1% SDS.

12. The method of claim 11, wherein the probe is from 10 to 200 nucleotides in length.

13. The method of claim 11, wherein the probe is from 15 to 100 nucleotides in length.

14. The method of claim 11, wherein the probe is from 15 to 30 nucleotides in length.

15. The method of claim 7, wherein the polymorphism detected comprises a T at the 6413th nucleotide of SEQ ID NO:2 or an A at the corresponding position on the complementary strand thereof.

16. The method of claim 11, wherein the polymorphism detected comprises a T at the 14378th nucleotide of SEQ ID NO:2 or an A at the corresponding position on the complementary strand thereof.

* * * * *

UNITED STATES PATENT AND TRADEMARK OFFICE
CERTIFICATE OF CORRECTION

PATENT NO.   : 6,933,118 B2
DATED        : August 23, 2005
INVENTOR(S)  : Hidetoshi Inoko and Gen Tamiya It is certified that error appears in the above-identified patent and that said Letters Patent is hereby corrected as shown below:

<u>Title page,</u>
Item [56], References Cited, OTHER PUBLICATIONS,
"Shiina T. et al." reference, delete "fo" and insert -- of --.

<u>Column 99,</u>
Line 17, insert -- comprises -- following "step".
Line 22, delete "sequence f" and insert -- sequence of --.

Signed and Sealed this

Seventh Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,933,118 B2
APPLICATION NO. : 10/164230
DATED : August 23, 2005
INVENTOR(S) : Hidetoshi Inoko and Gen Tamiya It is certified that error appears in the above-identified patent and that said Letters Patent is hereby corrected as shown below:

<u>Title page,</u>
Item 75, Inventors,
Hidetoshi Inoko, delete "1583-1-101, Funako, Atsugi-Shi, Kanagawa 243-0034 (JP)" and insert -- Kanagawa (JP) --

<u>Page 2,</u>
Item [56], line 13, References cited, OTHER PUBLICATIONS
Delete "Geneback Accession No. AB031479" and insert -- Genebank Accession No. AB031479 --

<u>Column 100:</u>
In the 5th line of Claim 6, delete "polymorphism indicates at the" and insert -- polymorphism indicates that the --
In the 6th line of Claim 7, delete "65° C. in" and insert -- 65°C in --
In the 6th line of Claim 11, delete "65° C. in" and insert -- 65°C in --

Signed and Sealed this

Tenth Day of April, 2007

JON W. DUDAS
*Director of the United States Patent and Trademark Office*